US012731164B2

(12) United States Patent
Bradley et al.

(10) Patent No.: US 12,731,164 B2
(45) Date of Patent: Sep. 8, 2026

(54) PLATFORM AND METHOD FOR TOKENIZING CONTENT

(71) Applicant: Datavault AI Inc., Beaverton, OR (US)

(72) Inventors: Nathaniel T. Bradley, Tucson, AZ (US); Alfred Blair Blaikie, III, Tinton Falls, NJ (US); Joshua S. Paugh, Tucson, AZ (US)

(73) Assignee: Datavault AI Inc., Beaverton, OR (US)

( * ) Notice: Subject to any disclaimer, the term of this patent is extended or adjusted under 35 U.S.C. 154(b) by 0 days.

(21) Appl. No.: 17/941,872

(22) Filed: Sep. 9, 2022

(65) Prior Publication Data

US 2023/0075767 A1 Mar. 9, 2023

Related U.S. Application Data

(60) Provisional application No. 63/242,123, filed on Sep. 9, 2021.

(51) Int. Cl.

*G06Q 30/0201* (2023.01)
*G06Q 10/0637* (2023.01)

(Continued)

(52) U.S. Cl.

CPC ..... *G06Q 30/0206* (2013.01); *G06Q 10/0637* (2013.01); *G06Q 20/065* (2013.01); *G06Q 20/3672* (2013.01); *G06Q 20/382* (2013.01); *G06Q 20/38215* (2013.01); *G06Q 20/3827* (2013.01); *G06Q 20/389* (2013.01); *G06Q 30/0208* (2013.01); *G06Q 30/0214* (2013.01); *G06Q 30/0234* (2013.01); *G06Q 30/0241* (2013.01); *G06Q 30/0645* (2013.01); *G06Q 40/04* (2013.01); *G06Q 50/02* (2013.01); *G16B 30/00* (2019.02); *G16H 10/40* (2018.01);

(Continued)

(58) Field of Classification Search

None

See application file for complete search history.

(56) References Cited

U.S. PATENT DOCUMENTS

| | | |
|---|---|---|
| 7,860,763 B1 | 12/2010 | Quinn |
| 8,204,805 B2 | 6/2012 | Eftekhari |

(Continued)

FOREIGN PATENT DOCUMENTS

| | | | |
|---|---|---|---|
| CN | 108537664 A | 9/2018 | |
| WO | WO-2017145004 A1 * | 8/2017 | ......... G06F 16/1834 |

(Continued)

OTHER PUBLICATIONS

The American Law Institute. "ALI-ELI Principles for a Data Economy." (Apr. 28, 2021). Retrieved online Jul. 18, 2023. https://www.ali.org/media/filer_public/ff/7c/ff7c5006-058e-4254-885d-b5d5725fd8be/date-economy-td2.pdf (Year: 2021).*

(Continued)

*Primary Examiner* — James A Reagan

(74) *Attorney, Agent, or Firm* — Goodhue, Coleman & Owens, P.C.

(57) ABSTRACT

A system, method, device, and platform for managing content utilizing tokens from a data platform. Providing an incentive for a user to generate content. The content is received from the user. The content is tokenized into one or more tokens. The tokenized content is distributed. The tokenized content is monetized based on a smart contract.

20 Claims, 25 Drawing Sheets

(51) Int. Cl.

| | |
|---|---|
| ***G06Q 20/06*** | (2012.01) |
| ***G06Q 20/36*** | (2012.01) |
| ***G06Q 20/38*** | (2012.01) |
| ***G06Q 30/0208*** | (2023.01) |
| ***G06Q 30/0214*** | (2023.01) |
| ***G06Q 30/0234*** | (2023.01) |
| ***G06Q 30/0241*** | (2023.01) |
| ***G06Q 30/0645*** | (2023.01) |
| ***G06Q 40/04*** | (2012.01) |
| ***G06Q 40/10*** | (2023.01) |
| ***G06Q 50/02*** | (2024.01) |
| ***G16B 30/00*** | (2019.01) |
| ***G16H 10/40*** | (2018.01) |
| ***G16H 50/30*** | (2018.01) |
| ***H04L 9/00*** | (2022.01) |
| ***H04L 9/32*** | (2006.01) |

(52) U.S. Cl.

CPC ........... *G16H 50/30* (2018.01); *H04L 9/3213* (2013.01); *H04L 9/50* (2022.05); *G06Q 40/10* (2013.01); *G06Q 2220/00* (2013.01)

(56) References Cited

U.S. PATENT DOCUMENTS 8,838,492 B1 9/2014 Baker
9,760,953 B1 9/2017 Wang
9,870,588 B1 1/2018 Genov
10,114,969 B1 10/2018 Chaney et al.
10,163,129 B1 12/2018 Agarwal et al.
10,255,641 B1 4/2019 Goldman
10,318,979 B2 6/2019 Frank et al.
10,341,105 B2 7/2019 Innes et al.
10,346,826 B2 7/2019 Boudville
10,482,174 B1 11/2019 Goodsitt
10,628,894 B1 4/2020 Ioannou
10,685,407 B1 6/2020 Cabrera
10,867,355 B1 12/2020 Wang
10,943,309 B1 3/2021 Morin
10,984,413 B2 * 4/2021 Armstrong ......... G06Q 20/3823
11,074,241 B2 * 7/2021 Kain ...................... G16H 40/20
11,121,877 B2 * 9/2021 Guillama ............... G16H 10/60
11,165,560 B2 * 11/2021 Guillama ............ G06F 16/1834
11,269,665 B1 3/2022 Podgorny
11,290,261 B2 * 3/2022 Reid ........................ G06F 21/32
11,301,582 B2 * 4/2022 Lee ..................... G06F 21/6254
11,321,652 B1 * 5/2022 Mahmood ........ G06Q 10/06316
11,645,417 B2 * 5/2023 Lee ..................... G06F 3/04847 726/2
11,658,805 B2 * 5/2023 Guillama ............ G06F 16/2365 713/168
2004/0128253 A1 7/2004 Jim
2007/0250700 A1 10/2007 Sidhu et al.
2007/0288312 A1 12/2007 Wang
2009/0157534 A1 6/2009 Arsiwala
2010/0076876 A1 3/2010 Brady
2010/0179860 A1 7/2010 Noel
2011/0208621 A1 8/2011 Feierstein
2012/0323718 A1 12/2012 Shkedi
2013/0132300 A1 5/2013 Margolis
2014/0164251 A1 6/2014 Loh
2014/0214636 A1 7/2014 Rajsky
2014/0344015 A1 11/2014 Puértolas-Montañés et al.
2015/0379563 A1 * 12/2015 Franosch ........... G06Q 30/0247 705/14.46
2016/0104153 A1 4/2016 Anderson
2016/0140668 A1 5/2016 Maguire
2016/0307063 A1 * 10/2016 Bright .................. G06V 30/153
2016/0342977 A1 11/2016 Lam
2017/0011460 A1 1/2017 Molinari
2017/0091843 A1 * 3/2017 Zeigler .............. G06Q 30/0601
2017/0111345 A1 4/2017 Heiman
2017/0126644 A1 5/2017 Ullrich et al.
2017/0134161 A1 5/2017 Goeringer et al.
2017/0169363 A1 6/2017 Salmasi et al.
2017/0206523 A1 7/2017 Goeringer et al.
2017/0214522 A1 7/2017 Code et al.
2017/0220540 A1 8/2017 Wang
2017/0221029 A1 8/2017 Lund et al.
2017/0230109 A1 8/2017 Kawai
2017/0243143 A1 8/2017 Engstrom
2017/0295023 A1 10/2017 Madhavan et al.
2017/0301026 A1 10/2017 Bensemana
2017/0301031 A1 10/2017 Naqvi
2017/0330174 A1 11/2017 DeMarinis et al.
2017/0337534 A1 11/2017 Goeringer et al.
2017/0346833 A1 11/2017 Zhang
2017/0372278 A1 12/2017 Frolov et al.
2018/0040073 A1 2/2018 Ghosh
2018/0101771 A1 4/2018 Schwarm
2018/0121337 A1 5/2018 Unsal
2018/0144153 A1 5/2018 Pead
2018/0144340 A1 5/2018 Kinnaird et al.
2018/0218456 A1 8/2018 Kolb
2018/0225693 A1 8/2018 Postrel
2018/0232526 A1 * 8/2018 Reid ................... G06F 21/6218
2018/0232775 A1 8/2018 Kim et al.
2018/0247302 A1 * 8/2018 Armstrong ......... G06Q 20/3827
2018/0262493 A1 9/2018 Andrade
2018/0264347 A1 * 9/2018 Tran ....................... G06V 40/28
2018/0276625 A1 * 9/2018 Saye ................. G06Q 20/3825
2018/0276626 A1 9/2018 Laiben
2018/0300693 A1 10/2018 Gopinath et al.
2018/0300772 A1 10/2018 Bushong, Jr.
2018/0314884 A1 11/2018 Lee
2018/0351949 A1 12/2018 Scott et al.
2018/0365686 A1 12/2018 Kondo
2019/0019208 A1 1/2019 Postrel
2019/0019218 A1 1/2019 Thompson et al.
2019/0026828 A1 1/2019 Preston et al.
2019/0043050 A1 2/2019 Smith et al.
2019/0050926 A1 2/2019 Cooper
2019/0052722 A1 2/2019 Gasking
2019/0058580 A1 2/2019 Tormasov et al.
2019/0066063 A1 2/2019 Jessamine
2019/0066205 A1 2/2019 Marks
2019/0066206 A1 2/2019 Marks
2019/0080402 A1 3/2019 Molinari et al.
2019/0080407 A1 3/2019 Molinari et al.
2019/0087844 A1 3/2019 Leekley
2019/0087893 A1 3/2019 Pellew
2019/0095439 A1 3/2019 Cai
2019/0102454 A1 4/2019 Sato et al.
2019/0102837 A1 4/2019 Smith et al.
2019/0114706 A1 4/2019 Bell et al.
2019/0121813 A1 4/2019 Galebach et al.
2019/0122243 A1 4/2019 Mizzone
2019/0122258 A1 4/2019 Bramberger et al.
2019/0130451 A1 5/2019 Logvinov
2019/0141048 A1 5/2019 Fallah et al.
2019/0147471 A1 5/2019 McKelvey et al.
2019/0149633 A1 5/2019 Evans et al.
2019/0155997 A1 5/2019 Vos et al.
2019/0156304 A1 5/2019 Hudson et al.
2019/0156363 A1 5/2019 Postrel
2019/0163700 A1 5/2019 Baumgardner et al.
2019/0164140 A1 5/2019 Pasupula
2019/0172067 A1 6/2019 Arora et al.
2019/0172153 A1 6/2019 Wyle
2019/0180266 A1 6/2019 Sidhu
2019/0180307 A1 6/2019 Cohen et al.
2019/0188411 A1 6/2019 Kroutik
2019/0205563 A1 7/2019 Gonzales
2019/0205932 A1 7/2019 Ericson
2019/0213633 A1 7/2019 Kokernak
2019/0236214 A1 8/2019 Kokernak
2019/0236286 A1 8/2019 Scriber et al.
2019/0236698 A1 8/2019 Postrel
2019/0244243 A1 8/2019 Goldberg et al.
2019/0342095 A1 11/2019 Simons
2019/0347442 A1 11/2019 Marlin
2019/0358515 A1 * 11/2019 Tran ...................... H04L 9/3236

(56) References Cited

U.S. PATENT DOCUMENTS

2020/0035341 A1* 1/2020 Kain ..................... G16H 10/20
2020/0058023 A1 2/2020 Travizano
2020/0074461 A1 3/2020 DeRosa-Grund
2020/0234268 A1 7/2020 Kohli
2020/0236091 A1 7/2020 Cooley
2020/0294033 A1* 9/2020 Wilson ............... G06Q 20/0658
2020/0374104 A1* 11/2020 Heath ................... H04L 9/3297
2020/0374125 A1* 11/2020 Guillama .............. H04L 9/0894
2020/0394723 A1 12/2020 Baker
2021/0081549 A1* 3/2021 Trenholm .............. G06N 20/00
2021/0150653 A1* 5/2021 Hjertstedt ............. G06F 40/166
2021/0192075 A1 6/2021 Sweeney
2021/0209245 A1* 7/2021 Lee ..................... G06F 3/04883
2021/0256510 A1* 8/2021 Armstrong .......... H04L 63/0471
2021/0271649 A1* 9/2021 Narayanaswami ... H04L 9/3239
2021/0377002 A1* 12/2021 Guillama ............ G06F 16/9024
2021/0385069 A1* 12/2021 Reid ..................... H04L 9/3239
2021/0390208 A1* 12/2021 Lee ....................... G06F 3/0488
2022/0012731 A1* 1/2022 DeRosa-Grund ... G06F 16/2365
2022/0050921 A1* 2/2022 LaFever .............. H04L 63/0407
2022/0075903 A1* 3/2022 Prasad .................. H04L 9/0825
2022/0140999 A1* 5/2022 Reid ..................... G06F 21/554
713/171
2022/0237565 A1* 7/2022 Dzierzanowski .... G06Q 10/103
2022/0245574 A1* 8/2022 Cella ....................... G06F 9/451
2022/0292547 A1* 9/2022 Peurifoy ................. H04L 51/52
2022/0309540 A1 9/2022 Blaikie, III
2022/0309541 A1 9/2022 Blaikie, III
2022/0335414 A1* 10/2022 Murray ............. G06Q 20/3674
2022/0374807 A1* 11/2022 Mahmood .............. G16H 10/40
2022/0406419 A1* 12/2022 Kruger ............... G06Q 20/3674
2023/0253100 A1* 8/2023 Caudill .................... G06N 3/09
705/3

FOREIGN PATENT DOCUMENTS

WO 2017190175 A1 11/2017
WO 2017197110 A1 11/2017
WO 2018007828 A2 1/2018
WO 2018058105 A1 3/2018
WO 2018209153 A1 11/2018
WO 2018211382 A1 11/2018
WO 2019051401 A1 3/2019
WO 2019083693 A1 5/2019
WO 2019094153 A1 5/2019
WO 2019099335 A1 5/2019
WO 2019113138 A1 6/2019
WO 2019121659 A1 6/2019
WO 2019133309 A1 7/2019
WO 2019152732 A1 8/2019
WO WO-2019198839 A1 * 10/2019 ............ G06Q 20/38
WO 2020097115 A1 5/2020
WO WO-2020132426 A1 * 6/2020 ............ G06F 16/48
WO 2020205642 A1 10/2020

OTHER PUBLICATIONS

W. Paul Vogt et al. "Selecting the Right Analyses for your Data Quantitative, Qualitative, and Mixed Methods." (2014). Retrieved online Jul. 18, 2023. https://doc.lagout.org/Others/Data%20Mining/Selecting%20the%20Right%20Analyses%20for%20Your%20Data_%20Quantitative%2C%20Qualitative%2C%20and%20Mixed%20Methods%20%5BVogt%2C%20Vogt%2C%20Gardner%20%26%20Haeffele%202014-07-02%5D.pdf (Year: 2014).*

Matthew Renze. "The Big Data Refinery." (Jul. 11, 2016). Retrieved online Jan. 19, 2024. https://matthewrenze.com/articles/the-big-data-refinery/ (Year: 2016).*

Jennifer Aue. "A guide to IBM's complete set of data & AI tools and services So you can be a fearless wielder of AI." (Oct. 14, 2020). Retrieved online Jan. 19, 2024. https://medium.com/design-ibm/a-guide-to-ibms-complete-set-of-data-ai-tools-and-services-29662433ad07 (Year: 2020).*

International Preliminary Report, PCT/US2019/059920, May 20, 2021, 8 pages.

International Search Report & Written Opinion, PCT/US2020/025495, Jul. 2, 2020, 15 pages.

International Search Report and Written Opinions, PCT/US2022/075985, Dec. 6, 2022, 12 Pages.

Saraji et al. "A blockchain-based carbon credit ecosystem." (2021 ). Jul. 1, 2021 (Jul. 1, 2021} Retrieved on Oct. 24, 2022 (Oct. 24, 2022) from . 12 pages.

* cited by examiner

2400

PLATFORM AND METHOD FOR TOKENIZING CONTENT

PRIORITY

This application claims priority to U.S. Provisional Patent Application No. 63/242,123 filed Sep. 9, 2021, respectively, which is hereby incorporated by reference in its entirety.

BACKGROUND

I. Field of the Disclosure

The illustrative embodiments relate to personal data management. More specifically, but not exclusively, the illustrative embodiments relate to a network, system, method, apparatus, and platform for data tokenization, physical asset tokenization, virtual asset tokenization, and monetization.

II. Description of the Art

The generation of various types of data including personal and commercial data has increased exponentially in recent years. Corporations and consumers create and store large volumes of unstructured data from multiple sources with no way of refining, valuing, and monetizing their data. Consumers' data is commonly generated and monetized from consumer web searches, profile data, social media profiles, and online surveys that generate revenue through advertisement delivery and brand to consumer marketing and outreach connectivity with no compensation to the actual owners of the data, the individual consumers/users, consumer groups, organizations, and data generators themselves.

SUMMARY OF THE DISCLOSURE

The illustrative embodiments provide a system, method, device, and platform for managing content utilizing tokens from a data platform. Providing an incentive for a user to generate content. The content is received from the user. The content is tokenized into one or more tokens. The tokenized content is distributed. The tokenized content is monetized based on a smart contract. Another embodiment provides a platform including a processor and a memory storing a set of instructions. The set of instructions are executed to perform the method herein described.

The illustrative embodiments provide a system, method, device, and data platform for tokenization of a precious physical, virtual, and data assets utilizing tokens. Information and asset price or variable cost or price ranges regarding the precious physical asset is determined. The precious physical asset is associated with one or more tokens. The one or more tokens represent ownership of the precious physical asset. Another embodiment provides a data platform including a processor and a memory storing a set of instructions. The set of instructions are executed to perform the method herein described.

For the purpose of clarity, precious physical assets may include 1) real-world or physical assets, 2) virtual, digital, and data assets, and/or a combination of both. Another embodiment provides a system for tokenizing and managing a precious physical asset utilizing one or more tokens. The system includes electronic devices executing a data application. The data application is configured to communicate information regarding the precious physical assets. The system also includes a data platform accessible by the electronic devices executing the data application through one or more networks. The data platform determines the market rate of the asset or may assign a potential value or a fixed price cost and may also help determine other relevant non-fixed pricing information regarding the precious physical asset, associates the precious physical asset with one or more tokens, communicates availability and smart contract assigned cost or access requirements of the one or more tokens associated with the precious physical asset, implements transactions for the one or more tokens, and distributes monies paid during the transactions for transfer of ownership or access to the one or more tokens associated with the precious physical asset, wherein the one or more tokens represent approved access, tracking ownership, or transfer of ownership of the precious physical asset.

The illustrative embodiments provide a system, method, device, and data platform for obtaining corporate data associated with one or more corporations. The corporate data is received by a data platform. The corporate data is segmented and tokenized into one or more tokens. The corporate data is valued. Potential monetization strategies are determined and options and recommendations for data value or token valuation are established, data value is calculated, marketed, and solicited for the improved monetization of corporate data. The monetization strategies are presented to one or more corporations, consumers, or other 3$^{rd}$ parties. Another embodiment provides a data platform including a processor and a memory storing a set of instructions. The set of instructions are executed to perform the method herein described.

The illustrative embodiments provide a system, method, device, and platform for managing carbon credits utilizing tokens. Carbon credits associated with a unit of carbon emissions are received. The carbon credits are tokenized to create tokens associated with each of the carbon credit types. The carbon credits are marketed to authorized parties. Transactions for the tokens associated with the carbon credits are performed. The transactions for the tokens are documented. Another embodiment provides a platform including a processor and a memory storing a set of instructions. The set of instructions are executed to perform the method herein described.

The illustrative embodiments provide a system, method, device, and data platform for managing DNA data utilizing tokens. DNA data associated with a user is obtained. The DNA data is stored in a DNA profile associated with the user by a data platform. The DNA data is tokenized into one or more tokens. The DNA data is monetized. Another embodiment provides a data platform including a processor and a memory storing a set of instructions. The set of instructions are executed to perform the method herein described.

The illustrative embodiments provide a system, method, device, and data platform for managing gaming data utilizing tokens. Gaming data associated with a player and one or more games are obtained. The gaming data is received by a data platform. The gaming data is inserted in a gaming profile. The gaming data is tokenized into one or more tokens. The gaming data is monetized based on preferences within the gaming profile. Another embodiment provides a data platform including a processor and a memory storing a set of instructions. The set of instructions are executed to perform the method herein described.

The illustrative embodiments provide a system, method, device, and platform for monetizing user data. One or more data elements associated with user data of a user are received from one of a number of sources. One or more tokens are created based on the user data. The user data is stored in a secure location. The user data is vended to one of a number of parties utilizing the one or more tokens. The user data is accessible from the secure location utilizing an indicator included in the one or more tokens. The user is compensated for vending the user data. Another embodiment provides a processor for executing a set of instructions and a memory storing a set of instructions configured to perform the method herein described.

Another embodiment provides a system for monetizing corporate and workplace user data. The system includes electronic devices executing a data application. The data application is configured to capture the user data associated with a user. The system also includes a data platform accessible by the electronic devices executing the data application through one or more networks. The data platform receives one or more data elements associated with the user data of the user from one of a plurality of sources, creates one or more tokens based on the user data, store the user data in a secure location, the user profile may deny access to the user data, or the user profile approves and vends access to user data and the data is exchanged to one of a plurality of parties utilizing the one or more tokens, and compensates the user for vending the user data, wherein the data is accessible from the secure location utilizing an indicator included in the one or more tokens.

Another embodiment provides a system for utilizing corporate and workplace user data. The system includes electronic devices executing a data application. The data application is configured to capture the user data associated with a user. The system also includes a data platform accessible by the electronic devices executing the data application through one or more networks. The data platform receives one or more data elements associated with the user data from the electronic devices, automatically confirms the one or more data elements are applicable to the user, adds the one or more data elements to a data set associated with the user, determines whether the data set is complete after adding the data element to the data set, and creates one or more tokens based on the data set of the user.

Another embodiment provides a data platform. The data platform may include a processor for executing a set of instructions and a memory for storing the set of instructions. The set of instructions may be executed to receive one or more data elements associated with the user data from one of a number of sources, automatically confirm the one or more data elements is applicable to the user, add the one or more data elements to a data set associated with the user, determine whether the data set is complete after adding the data element to the data-set, and create one or more tokens based on the data set of the user.

In other embodiments, one or more of the following may be implemented. Instructions are received from the user specifying how the data set is utilized and the user is compensated for sharing the tokens with one or more interested parties. Additional data elements may be requested in response to determining the data set is complete or incomplete utilizing questions, surveys, and a user profile associated with the user. The one or more data elements are authenticated as being associated with the user. The token is a blockchain crypto token and points to the data set for secure access by one or more interested parties. Distinct data sets are clustered into a data pool, the data pool is cross populated with distinct data sets, and the data pool is segmented to identify saturation, missing, incomplete, or nonrelevant data. A determination is made regarding the relevance of the data pool to one or more interested parties. Payments are received from one or more interested parties to access the data set utilizing the token. One or more users are compensated for granting access to their data sets. The interested parties represent advertisers, marketers, data brokers, consumer outreach, or businesses that desire access to the user data in the data set.

The illustrative embodiments provide a system, method, and platform for monetizing data. A selection is received from a user to monetize data associated with the user. The data associated with user is compiled. A security token is generated including the data. The data is monetized utilizing the security token in accordance with the selection.

In other embodiments, the data may include digital profiles and digital assets that are monetized for data and asset tracking purposes. Data validation may be performed through user opt-ins that are identified and confirmed by the user. Token based compensation for consumer data allows for the direct control and monetization of their data (e.g., web data, application data, profiles, personal measurements, readings, etc.). Compensation may be performed through digital currencies, hard currencies, charitable contributions, and tax deductions. The earnings for a user may also be donated. Users may be rewarded for additional data uploads, updates, additions, amendments, surveys/questionnaire fulfillment, and so forth. The tokens may be utilized to pay a vendor or third party for a product, service, system, or data, secure a digital asset, tracking the life of an asset, share a stake in an asset or company, participate in an initial coin offering, receive a reward, maintaining and managing a digital asset, make a charitable contribution, or receive a tax deduction.

In other embodiments, the data may include digital profiles that are monetized for access to specific consumer or corporate data points. Data validation may be performed through user opt-ins that are identified and confirmed by the user. Token based compensation for consumer data allows for the direct control and monetization of their data (e.g., web data, application data, profiles, personal measurements, readings, etc.). Compensation may be performed through digital currencies, hard currencies, charitable contributions, and tax deductions. The earnings for a user may also be donated. Users may be rewarded for additional data uploads, updates, additions, amendments, surveys/questionnaire fulfillment, and so forth. The tokens may be utilized to pay a vendor or third party for a product, service, system, or data, secure a digital asset, tracking the life of an asset, share a stake in an asset or company, participate in an initial coin offering, receive a reward, maintaining and managing a digital asset, make a charitable contribution, or receive a tax deduction.

In other embodiments, the data may include digital political profiles and political opinions that are monetized for specific data points related to political affiliation, user political beliefs, and voting plans are self-identified data and self-validation may be performed through user opt-ins that are identified and confirmed by the user. Token based compensation for political data such as voting preferences or other determinations made prior to the vote being cast can be used for political mapping and polling and allows for the user to have more direct control over the user and monetization of their political data. Refineries can be created for the data that the political campaigns own this data can then be resold. User compensation may be generated by the politician or political campaigns and paid to the data owners in order to test the temperature on any issue that might be important to their constituents. The compensation may be generated from the politicians, political campaigns or through political action groups utilizing a process that allows voters to tokenize their data and political opinion and receive remuneration through digital currencies, hard currencies, charitable contributions, and tax deductions. The earnings for a user's data may also be donated to the campaign of their choice. Users may be solicited and rewarded for additional data uploads, updates, additions, amendments, surveys/questionnaire fulfillment, and so forth. The tokens may be utilized to pay a vendor or third party for a product, service, system, or data, secure a digital asset, tracking the life of an asset, share a stake in an asset or company, participate in an initial coin offering, receive a reward, maintaining and managing a digital asset, make a charitable contribution, or receive a tax deduction.

BRIEF DESCRIPTION OF THE DRAWINGS

Illustrated embodiments are described in detail below with reference to the attached drawing figures, which are incorporated by reference herein, and where.

DETAILED DESCRIPTION OF THE DISCLOSURE

Figure 1:
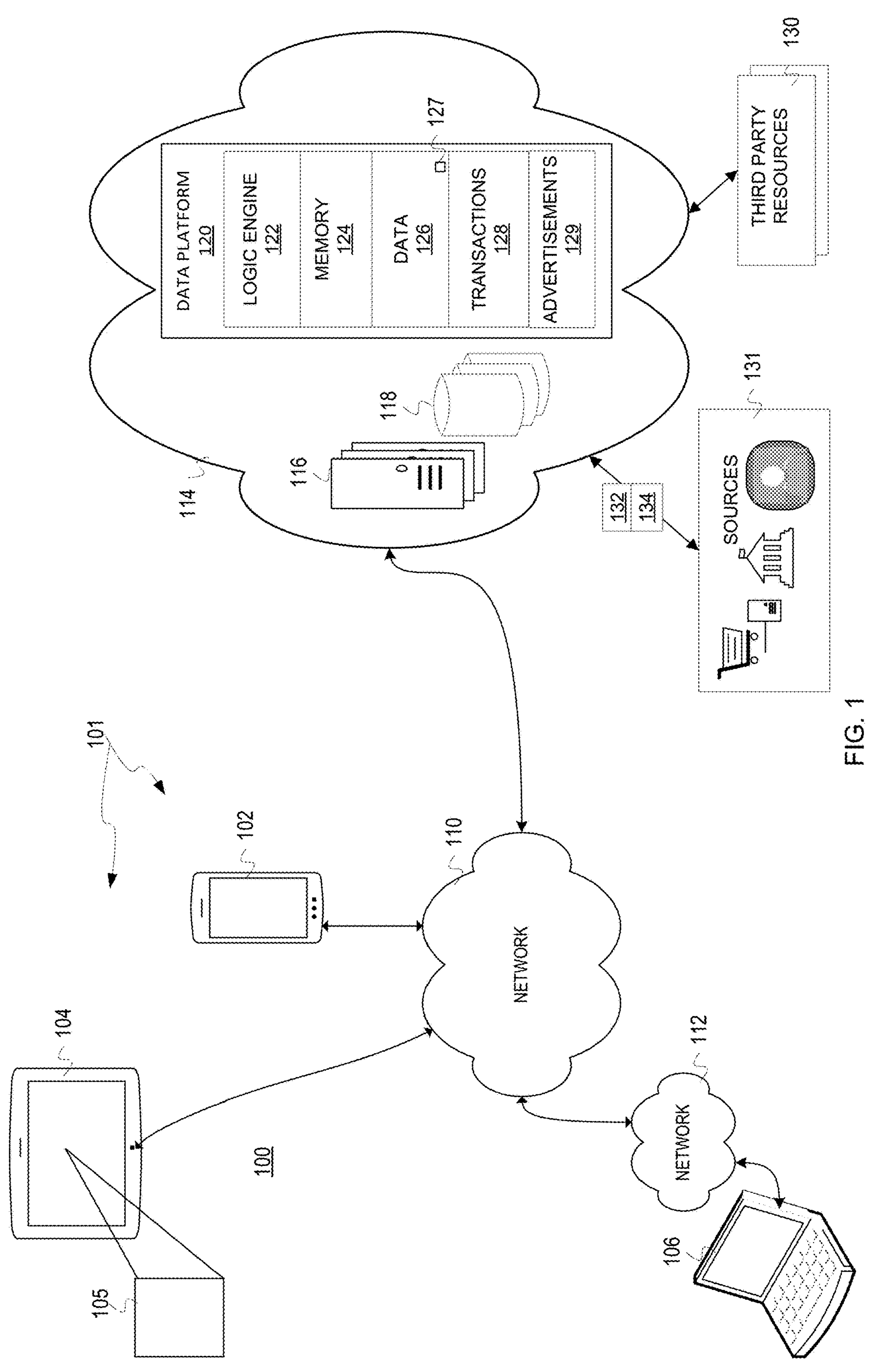
FIG. 1 is a pictorial representation of a system for managing user information in accordance with an illustrative embodiment.

The illustrative embodiments provide a network, system, method, platform, and devices for data segmentation for improved data and asset management and monetization. The data management may include data control, data governance, data valuation, compliance and security, risk management, anti-money laundering control Fraud detection, sanction screening, regulatory reporting. The illustrative embodiments provide individual consumers, entities, organizations, corporations, and data vendors a measurements, pool, segment, and value for consumer and corporate data. As a result, the data may be utilized as a measurable asset. The data value may be derived from the segmentation and identification of unique data points within a larger shared data pool. The utilization of the data provides for equity holdings, credit card activity, and user specified parameters and preferences to be processed for the purpose of targeting advertisements to consumers. The illustrative embodiments create a relationship between data sets regarding ownership of stock portfolios, equities, investment holdings, and user associated interests including receipts for baskets of goods documenting the products that consumers buy or items consumers are potentially shopping for that are owned by the companies represented within their portfolios, in order to strengthen and enhance their investments in companies with their current investment portfolios.

Data tracking and segmentation provides for improved real-time and online advertisements, product recommendations, stock tips, investment insights, and shopping recommendations via an ad-targeting network. The improvements allow advertisements to be selectively targeted based on consumer profiles that may include real-time and historical purchasing data and the real-time and historical stock and equity portfolios. Data from multiple primary sources may be leveraged towards the targeted advertising including stock trading data, stock custody data, and consumer credit/debit card transaction data.

The advertising network data is processed, and advertisements are delivered to users/consumers so that they can act in their own best interests and purchase products, services, and commodities that are in alignment with their holdings. This technology tool provides investors who own stock in specific companies a means to support that stock ownership by receiving targeted purchase recommendations and advertisements that allows consumers them to make informed purchase decisions that facilitate and support the success of each stock held within own individual investor portfolio by purchasing those products. Alternatively, when users buy products outside the products represented in their portfolios, the user may receive data and advertisements from brokers to buy or switch to the stocks associated to those products.

The illustrative embodiments utilize data records from stock transactions, equities, credit card transactions, user preferences, and other self-interests to perform targeted advertisements. Different data clearing houses, groups, or parties may be utilized to process and verify user and consumer data. For example, every stock transaction including the stock, shares, amount, type of transaction (e.g., limit, market, short, futures transaction, option, etc.), and other information is received, processed, and stored.

The illustrative embodiments provide a system, method, platform, and network for encrypting, securing, developing, and managing data valuations, transactions, and utilization. The data may be accessible from any number of authorized and connected devices. The illustrative embodiments allow users/consumers, consumer groups, companies, organizations, entities, governments, and other parties worldwide to develop data strategies and the conversion of any data into a monetizable asset (including a transactable token currency). For example, a platform is provided for capturing, identifying, monetizing, converting, utilizing, and improving data.

As referenced herein, data refers to the personal or commercial data, user profiles, web profiles, search profiles, application profiles, and other information applicable to a user, consumer, entity, device, system, or other party. The illustrative embodiments comply with all applicable data privacy and administration rules, laws, and best practices. Any number of mobile devices, computers, machines, servers, arrays, or so forth may be utilized to implement the illustrative embodiments. A user may tokenize his/her data and convert all applicable data into an asset that may be controlled, valued, and monetized in commercial transactions. The illustrative embodiments also provide the user the ability to control data generation and the seamless utilization of the data. For example, algorithmic processing may determine how and when online and digital data is utilized and monetized, the price point or fair data valuation based on applicable pricing (e.g., demographic, global, location, utilization, etc.) based on going rates, principles of supply and demand, market economics, market analysis, machine learning, exchanges, auctions, real-time bidding, artificial intelligence, and so forth. Relevant information regarding data utilization may be acquired in real-time, based on historical transactions/archives, selling prices, or other applicable information or data that informs the value of a data sale or transaction. The illustrative embodiments allow the end user to select advertisement preferences that coincide with their stocks/shares, ownerships, interests, holdings, demographics, opinions, behaviors, beliefs, social structure, purchase plans, and real-world desires. The opportunity for the user to sell the data to the highest bidder provides enhanced choices for managing and utilizing their personal data that are not allowed by existing systems, such as cookie tracking based advertisements.

The illustrative embodiments may receive, process, collect, and source data from any number of traditional data collection methods, such as online (e.g., websites, mobile applications, user profiles, etc.) and real-world sources (e.g., location, retail purchases, credit card purchases, physical assets, etc.). The illustrative embodiments are a considerable improvement over traditional targeting, advertising, and marketing techniques, processes, and systems. For example, traditional blind advertisements may be transformed into a precisely targeted advertisement based on user verified and confirmed data, sources and information allowing each individual user to indicate products and service interests. Data in each user's data profile may be effectively utilized. Data, profiles, data sets, data pools, and other compilations may be tokenized to better protect, manage, and monetize the various types of data. The illustrative embodiments improve the functionality of computer networks that process information to be monetized.

In one embodiment, tokens may be created that track the data. The tokens may include information or metadata regarding the data and may point to a location where the data or physical item is stored. The token may be utilized to provide a key, identifier, pointer, indicator, or link required to securely access the data. As a result, the tokens may be created, communicated, bought, sold, and otherwise monetized through a blockchain system. The tokens may include a pointer that securely points to the data being monetized whether for a single user, organization, company, or multiple users. In another embodiment, the tokens themselves may include the data that is being monetized or otherwise exchanged.

The illustrative embodiments may be utilized to perform a transaction for the data. The data may be grouped, associated, and commoditized for any number of trades, exchanges, purchases, donations, or other transactions. The data may be associated with a platform for transactions involving the data and associated advertisements. The transaction may be performed automatically or based on user input, feedback, instructions, or commands.

One embodiment provides a blockchain based security token system that gives consumers the ability to control, monetize, and/or donate any or all of the proceeds from the utilization, sale, or sharing of their profile and/or data and advertising-based revenue. The illustrative embodiments curate or collect data in real-time from users based on an opt-in system with clear compensation and renumeration guidelines. For example, any number of computing or communications devices, platforms, applications, or so forth may be utilized to capture the data.

The security tokens utilized may represent any number of existing, custom/proprietary, and other tokens. In one embodiment, formatted, structured, or unstructured data may be converted into an encrypted token that represents, includes, or references the applicable data. The security interest in a data asset may be represented in the form of a token. Data across numerous fields and with different utilizations may be captured in a token (or tokenized). For example, intelligence, counterintelligence, consumer profiles, consumer/user, private, public, and other types of data may be captured and monetized. For example, the illustrative embodiments may provide a data management system that allows an asset, such as ownership of a digital profile to be tokenized as an asset that may be tracked, grown, and expanded through an opt in submission from multiple sources and monetized digitally through an e-commerce platform.

The security tokens may be issued, regulated, managed, and distributed by a platform to comply with the existing regulatory framework. The platform may provide a data monetization process for creating and performing transactions between buyers and sellers (e.g., similar to a stock trading platform). The illustrative embodiments may apply pricing based on a set price range, guidelines, industry-standard, or market rate. The data in the form of a token may allow the user to directly control and monetize their data in a transparent and secure blockchain platform. Consumers may receive security tokens in several ways when they sign up to participate in the system/service, when and where they opt in to include their data in the marketplace and Information Data Exchange, and when corporations and/or third parties purchase or monetized access to their data. For example, the data may be managed within a self-directed and mobile computing environment. The illustrative embodiments allow users to determine how and when their data is shared and monetized eliminating guesswork used by search, advertising, and marketing companies to generate user approved and desired consumer marketing data.

In one embodiment, the asset of data is created by the opt-in submission of a user's stock/ownership/interest profile, trading profile/account, social network profile(s), website utilization profiles, or generic/customized profile, and the associated data. The platform may be further used to secure all rights to any revenue streams associated with the data asset (e.g., any sale, sharing, or monetization of the user profile to a third party, site, or advertiser). By opting into the program, the user is providing their profile and perfecting the profile to match their actual daily living and purchases of products. As a result, the illustrative embodiments put the user in full control of the use and monetization of their data while avoiding the erroneous or inaccurate use of information and blind ad targeting practices inherent in currently available advertising programs and systems. The illustrative embodiments take third-party unauthorized or on monetized used of poor user data and enables an accurate and monetized data stream to be created for the user. The user benefits as do the third parties that are using the more accurate data. For example, assets associated with the user (e.g., stocks, hedge funds, business entities, charitable organizations, etc.) may benefit by adding revenue, increasing in value/valuation, and otherwise benefiting the user.

The illustrative embodiments may enable the user to track utilization and monetization of their data in a more transparent fashion. As a result, the user may be able to see and track dividends, revenue sharing, price appreciation, or other forms of digital and real-world asset monetization. For example, a value-based reward system tracked utilizing blockchain may be implemented. Smart contracts may be utilized with blockchain to ensure proper utilization and monetization of the data for verification purposes. The secured token generation process of the user data/profile provides proof of ownership to the user and ensures contract conditions are written into the smart contract code within the blockchain structure. The blockchain records maintain and track the creation, issuance, management, and monetization of each token throughout the lifetime of the user's involvement and ownership of their data. In one embodiment, a user may be rewarded with additional tokens for keeping their data/profile updated as well as keeping the data current through additional participation in surveys, watch a video, verify, a purchase, add studies, product marketing, expanded data provisioning, and questionnaires.

The user may be incentivized to provide additional data, such as pictures, audio content, videos, location (e.g., real-time, GPS, beacon, triangulation, delayed for safety, historical, etc.), Internet protocol address, purchases, purchase plans, investment, investment interests, identification of friends from each social network, sharing access to third-party applications, search data, views, likes, shares, comments, and so forth. As a result, the user may specify advertisement preferences that are associated with their stocks, portfolio, assets, equities, holdings, interests, demographics, opinions, behaviors, beliefs, social structure, purchase plans, and real-world desires. The user data that is recorded and stored may reside permanently on the blockchain, but typically only has a one to three-year lifecycle to be relevant. Thus, the user is incentivized to maintain, share, and update their data and associated profiles.

The data profile may be singular to a user or may be expanded to include deeper insights into a family, group of friends, employees, or other affiliated or associated groups. For example, a family circle profile may include an opt in for parents, children, grandparents, uncles, cousins, neighbors, family friends, and so forth. The data profile may be shared as a family asset between a partner, spouse, and children allowing the family data to be managed and monetized as a single asset. As a result, advertisers and others may get deeper insights into participating users. The illustrative embodiments manage the data collection, pricing, reconciliation, verification, payments, or so forth. Advertisers may be able to identify consumer data that is relevant to their campaign in order to provide direct incentives and/or monetization for users who provide specific advertiser-based insights. For example, a user may select to support a corporate restaurant of which a brother is a part-owner, an online educational institute that a friend works for, or a business that supports charities approved of by the user.

The illustrative embodiments may also allow user to transfer or donate the revenue or value generated for a charitable deduction or associated tax deduction. Each of the described data components is 100% opt in with users being rewarded for sharing specific data points that are desirable to advertisers or other third parties. For example, users may opt-out of specific data points that the do not wish to share with advertisers. The data captured by the illustrative embodiments may be consolidated and purchased by advertisers who provide incentives, rewards, or donations in exchange for access to users and focus group data used for the mining of advertiser-based user insights, analytics, marketing, and advertisement targeting.

The illustrative embodiments may also be utilized to create a data index that catalogs user profiles, data sets, and data transactions. Advertisers may then select a pricing structure for each type of data profile component that is desirable to advertisers thereby creating a virtual market for advertisers to purchase real time user data. The changing values of the data may be tracked over time for specific user profiles, consumer groups, and data pools based on their value to advertisers. The use of security tokens tied to user profiles creates a marketable asset that gives greater validity to commercial uses of blockchain technologies and the security token market.

Cryptographic, security, or digital tokens may be exchanged for actual currency, preferred stock options, stock warrants, bonds, exchange traded fund (ETF) shares, initial coin offerings (ICO), gift cards, vouchers, and other forms of compensation. Tokens may be utilized to communicate data and compensate users, service providers, aggregators, advertisers/marketers, and other applicable parties. The systems may also manage any number of smart contracts between relevant parties, such as the users/consumers, service providers, network operators, content providers, and so forth. The tokens utilized by the illustrative embodiments may be utilized for any number of purposes including compensation, communicating the data, data sets, and data pools, and secure management of the data. The system may utilize multiple types of tokens (e.g., asset tokens, utility tokens, etc.) that are utilized together within the blockchain. Various smart contracts and/or decentralized applications may be self-executed to process and manage the various transactions occurring on the blockchain. The illustrative embodiments including the systems, methods, devices, processes, and components described herein may implement any number of blockchain implementations.

The blockchain system may utilize crypto-protocols and crypto-token-protocols. For example, the blockchain system may generate tokens, manage a protocol utilizing a consensus algorithm, and record the transactions and other actions in a distributed ledger. The various protocols may control who, when, and how the various parties may control and otherwise manage the blockchain through any number of public and private permissions.

The illustrative embodiments provide and utilize a platform and the blockchain to tokenize data from real-world assets, consumer assets, personal assets, and corporate assets for the purpose of documentation, validation, valuation, and tokenization for improved connectivity sale, provenance tracking, and monetization of data and real-world assets.

Tokenizing personal, and corporate assets is accomplished by creating, pooling, assessing, and determining the market value of each tokenized asset via a data refinery and executing the sale or monetization of tokenized assets in the data asset marketplace (i.e., Information Data Exchange). The ability to better refine value and monetize personal, digital, and real-world assets presents a new type of investment opportunity to a broader potential investor base.

This provides increased corporate and consumer data value, and greatly improves user ability to better monetize personal data, real world data assets, and real-world physical assets and provides improved liquidity compared to other traditional securities. Each individual data point or real-world digital asset may be valued and tracked through a tokenization process that tokenizes and deidentifies each user specific individualized consumer or corporate data point or real-world asset. These data-points are pieces of information related to a real-world asset or data based assets which are stored inside blockchain blocks, which enables consumers and corporations to create and participate in a data valuation and data monetization payment processing ecosystem that utilizes a data refinery and data exchange creating an improved privatized data protection platform that improves the ability to facilitate data and asset monetization features across personal consumer and corporate data assets and real-world data assets and across physical holdings allowing for improved process for data access, data interaction, data-valuation, and data monetization on the blockchain.

Tokenization and monetization of core data and underutilized or latent corporate data, consumer data and real-world physical assets is an unlimited resource for monetization that grows exponentially each year. These untapped or underused data pools and asset pools may be tokenized for sale, which may unlock latent consumer and corporate value in a number of ways including new revenue streams, improved operational efficiency, enhanced customer experience and deeper customer connectivity and loyalty. These data pools provide an enhanced consumer experience through optimized and refined data utilizations, that by nature are inherently more valuable in a data asset marketplace setting and that also through the Information Data Exchange, which provides an enhanced level of data ownership and data protection and control.

With the wide proliferation of the internet, smart phone and devices, digital data is captured in a wide range of corporate and human activities in countless methodologies and formats. The illustrative embodiments better refine and value tokenized assets. The platform is paired with the blockchain to connect consumers, brands, advertisers, retail, corporations and provides improved incentives for participation in a blockchain based real-world and data asset valuation, data pooling, validation, and tokenization process.

FIG. 1 is a pictorial representation of a system 100 for managing user information in accordance with an illustrative embodiment. In one embodiment, the system 100 of FIG. 1 may include any number of devices 101, networks, components, software, hardware, and so forth. In one example, the system 100 may include a smart phone 102, a tablet 104 displaying graphical user interface 105, a laptop 106 (altogether devices 101), a network 110, a network 112, a cloud system 114, servers 116, databases 118, a data platform 120 including at least a logic engine 122, a memory 124, data 126, tokens 127, and transactions 128. The cloud system 114 may further communicate with sources 131 and third-party resources 130. The various devices, systems, platforms, and/or components may work alone or in combination.

Each of the devices, systems, and equipment of the system 100 may include any number of computing and telecommunications components, devices or elements which may include processors, memories, caches, busses, motherboards, chips, traces, wires, pins, circuits, ports, interfaces, cards, converters, adapters, connections, transceivers, displays, antennas, operating systems, kernels, modules, scripts, firmware, sets of instructions, and other similar components and software that are not described herein for purposes of simplicity.

In one embodiment, the system 100 may be utilized by any number of users, organizations, or providers to aggregate, manage, review, analyze, process, distribute, advertise, market, display, and/or monetize data 126. The data may include personal data, commercial data, data sets, data pools, and other forms of data. For example, the data 126 may be utilized in marketing or advertisements for goods or services associated with the user (as well as family and friends as allowed or specified). In one embodiment, the goods and services represent any number of items, content, products, or services sold by a business, entity, organization, or entity. In one embodiment, the system 100 may utilize any number of secure identifiers (e.g., passwords, pin numbers, certificates, etc.), secure channels, connections, or links, virtual private networks, biometrics, or so forth to upload, manage, and secure the data 126, generate tokens, and perform applicable transactions. As noted, the system 100 may be a blockchain system that utilizes a digital ledger to track tokens 127, transactions 128 involving the data 126 and advertisements 129. For example, the digital ledger may store the data 126, tokens 127, transactions 128, and advertisements 129 along with their details, information, and data. The devices 101 are representative of multiple devices that may be utilized by businesses or consumers, including, but not limited to the devices 101 shown in FIG. 1. The devices 101 utilize any number of applications, browsers, gateways, bridges, or interfaces to communicate with the cloud system 114, platform 120, and/or associated components. The devices 101 may include any number of Internet of Things (IoT) devices.

The data 126 may include a number of different data types. The data 126 may include demographic data, consumer data, family and health data, property data, ownership data, purchase data, behavioral data, interests and activity data, and other applicable types of data. The data 126 or advertisements 129 may store the good, services, and products that the user is interested in. The user may represent individuals, families, groups, entities, businesses, aggregations, or other parties.

Demographic data may be a combination of static and influx data points that include age, gender, occupation, marital status, education/education level, income level, religion, birthday, family size, ancestry, and so forth. Demographic data, although mostly static, is commonly quite important to marketers and other interested parties. Consumer data may include websites visited, purchase plans, purchases, brand affinity, cars, clothes, travel, and other information applicable to users, clients, customers, groups, or so forth. The family and health data may include permanent or long-lasting data elements which may be helpful for predicting future purchases and include information related to family, health, and medical conditions, such as childcare, diapers, diabetes, incontinence, rental information, and so forth. The family and health data have a large potential for cross marketing of data. Property data may include information regarding ownership, rentals/renters, address, for sale, square footage, occupants, past occupants pool, and vehicle ownership. In one embodiment, data related to vehicles, such as ownership, title, gas mileage, emissions, tire readout, recalls, and so forth may be tokenized for alerts and consumer data monetization via the platform. This data may be treated and value as static data (even though changes are likely and expected). The interests and activity data may include data regarding hobbies, general interests, product and brand preferences, and other applicable influx data. Political affiliation data may be a matter of public record in many states as the user self identifies. The data may be static, or perennial based on the user's voting record. The user may choose to self-identify political and voting information and voting plans or may keep that private. In one embodiment the platform may be used to create an opinion economy, where governments, cities, companies, advertisers, brands, or any data solicitor may obtain real time information and data from deidentified users allowing users and government, advertisers, and outreach providers to connect and exchange currency or value for providing data solicitors with a direct connection to improved consumer data.

The wireless device 102, tablet 104, and laptop 106 are examples of common devices 101 that may be utilized to capture, receive, and manage data 126, perform transactions 128, and communicate advertisements 129. For example, the various devices may capture data relevant to the user that is subsequently monetized for the benefit of the user (e.g., location, purchases, behavior, web activity, application use, digital purchases, etc.). Other examples of devices 101 may include e-readers, cameras, video cameras, electronic tags, audio systems, gaming devices, vehicle systems, kiosks, point of sale systems, televisions, smart displays, monitors, entertainment devices, medical devices, virtual reality/augmented reality systems, or so forth. The devices 101 may communicate wirelessly or through any number of fixed/hardwired connections, networks, signals, protocols, formats, or so forth. In one embodiment, the smart phone 102 is a cell phone that communicates with the network 110 through a 5G connection. The laptop 106 may communicate with the network 112 through an Ethernet, Wi-Fi connection, cellular, or other wired or wireless connection.

The data 126 may be collected and sourced from any number of online and real-world sources including, but not limited to, clearinghouses (e.g., stocks, credit card transactions, etc.), data clearinghouses, website traffic and cookie-based analytics, social media, application data, point of sale, purchase, and transaction history, loyalty programs and coupons, payment services, location-based email list for mailers, surveys and questionnaires, and other applicable sources. The data 126 may be captured based on the permissions, authorization, and confirmation of the user. For example, the data 126 may include stock trading data, stock custody data, and consumer credit/debit card transaction data. The data 126 may also store information regarding a user's purchases (e.g., past, present, future, likely, etc.), interests (e.g., personal, commercial, etc.), business/business needs, and other applicable information. The data 126 may also store information regarding the family, friends, and associates of the user if authorized or requested by the user. As a result, the user may be able to support businesses and groups associated with friends and family as well by receiving targeted advertisements and potentially purchasing goods/services based on those advertisements.

These same data collection sources may be utilized to perform analysis of the data 126. In one embodiment, the data 126 may be captured through registered account information, programs/applications, website traffic, and tracking cookie-based analytics. For example, information, such as time spent on each site, page views, clicks, conversions, relevant content, trends, and other information may be recorded as part of the data 126. The data 126 may also include digital or online transactions performed through services, such as PayPal®, Venmo®, Zelle®, Google®, Square®, WePay®, Skrill®, Payza®, Stripe®, Dwolla®, Amazon Pay, 2checkout®, and other similar services.

The data 126 may be captured through social media and applications. Social media data may be utilized to provide real-time polls, surveys, questionnaires, likes and dislikes, feedback, preferences for media content, site traffic, interests, and numerous other consumer data. Any number of mobile, computing, personal assistant (e.g., Siri, Alexa, Cortana, Google, etc.), or other applications may be utilized. Social media data may be utilized as definitive or anecdotal data.

The data 126 may also be captured through point of sale (POS) transactions, card transactions, in-person purchase, digital purchases, and purchase history. In one embodiment, a credit card clearing house may be utilized to capture the data. Customers, consumers, and clients may be comfortable with sharing the specific data points associated with point-of-sale transactions or basket of good analysis due to established practices. The point-of-sale transactions may include extensive data, including, but not limited to, name, address, item/service, price, credit card type, purchase location, date, brand preference, brand category, product affinity, spending levels, order history, inventory, restock data, purchase demographics, and so forth. Point-of-sale and transaction history data may have static, perennial, and influx data points with the value of each data point being tracked and measured within the data marketplace using the data valuation index, and data calculator that further informs the Information Data Exchange and the data derivatives marketplace.

The data 126 may also include location-based information and communications. An example of static and perennial data points that may be collected include a standard web form, email request form, wireless triangulation, routers/towers/access points reached, proximity beacons, and so forth. The location-based communications may capture data, such as email, consumer/business addresses, phone numbers, and so forth.

The data 126 may also include surveys and questionnaires. Responses to surveys and questionnaires may be one of the best ways to gather and inform information regarding the user's demographics, interests, and preferences that may not be able to be determined in other ways due to privacy, entity names, applicable laws, and so forth. The ability to gather real-world consumer insights may help complete or round out a user profile. The surveys and questionnaires may be performed digitally (e.g., websites, extensions, programs, applications, browsers, texting, or manually (e.g., audibly, on paper, etc.). Responses to surveys and questionnaires may help achieve saturation of datapoints for user profiles.

The cloud system 114 may aggregate, manage, analyze, and process data 126 and tokens across the Internet and any number of networks, sources 131, and third-party resources 130. For example, the networks 110, 112, may represent any number of public, private, virtual, specialty (e.g., trading, financial, cryptocurrency, etc.), or other network types or configurations. The different components of the system 100, including the devices 101 may be configured to communicate using wireless communications, such as Bluetooth®, Wi-Fi®, or so forth. Alternatively, the devices 101 may communicate utilizing satellite connections, Wi-Fi, 3G, 4G, 5G, LTE, personal communications systems, DMA wireless networks, and/or hardwired connections, such as fiber optics, T1, cable, DSL, high speed trunks, powerline communications, and telephone lines. Any number of communications architectures including client-server, network rings, peer-to-peer, n-tier, application server, mesh networks, fog networks, or other distributed or network system architectures may be utilized. The networks, 110, 112, and cloud system 114 of the system 100 may represent a single communication service provider or multiple communications services providers.

The sources 131 may represent any number of clearing houses, web servers, service providers (e.g., trading platforms, credit card companies, transaction processors, etc.), distribution services (e.g., text, email, video, etc.), media servers, platforms, distribution devices, or so forth. In one embodiment, the sources 131 may represent the businesses that purchase, license, or utilize the data 126, such as advertising or marketing goods and services utilizing the system 100. In one embodiment, the cloud system 114 (or alternatively the cloud network) including the data platform 120 is specially configured to perform the illustrative embodiments and may be referred to as a system or platform.

The cloud system 114 or network represents a cloud computing environment and network utilized to aggregate, process, manage, generate, sell, monetize, and distribute data 126 and advertisements 129 while supporting the transactions 128 and utilization. The cloud system 114 may implement a blockchain system for managing the data 126, transactions 128, and advertisements 129. For example, any number of blockchain tokens may be utilized to manage the data and ensure proper compensation of the user. The cloud system 114 allows data 126, transactions 128, and advertisements 129 from multiple businesses, users, managers, or service providers to be centralized. In addition, the cloud system 114 may remotely manage configuration, software, and computation resources for the devices of the system 100, such as devices 101. The cloud system 114 may prevent unauthorized access to data 126, tools, and resources stored in the servers 116, databases 118, and any number of associated secured connections, virtual resources, modules, applications, components, devices, or so forth. In addition, a user may more quickly upload, aggregate, process, manage, view, and distribute data 126 (e.g., profiles, updates, surveys, content, etc.), transactions 128, and advertisements 129 where authorized, utilizing the cloud resources of the cloud system 114 and data platform 120.

The cloud system 114 allows the overall system 100 to be scalable for quickly adding and removing users, businesses, authorized sellers, interest-based information, transaction-based information, analysis modules, distributors, valuation logic, algorithms, moderators, programs, scripts, filters, transaction processes, distribution partners, or other users, devices, processes, or resources. Communications with the cloud system 114 may utilize encryption, secured tokens, secure tunnels, handshakes, secure identifiers (e.g., passwords, pins, keys, scripts, biometrics, etc.), firewalls, digital ledgers, specialized software modules, or other data security systems and methodologies as are known in the art.

Although not shown, the cloud system 114 may include any number of load balancers. The load balancer is one or more devices configured to distribute the workload of processing the uploaded data 126 as well as applicable transactions to optimize resource utilization, throughput, and minimize response time and overload. For example, the load balancer may represent a multilayer switch, database load balancer, or a domain name system server. The load balancer may facilitate communications and functionality (e.g., database queries, read requests, write requests, command communications, stream processing, etc.) between the devices 101 and the cloud system 114. For example, the cloud system 114 may offload verification of users that seek to be added to the system 100 along with applicable data 126 and information. Load balancing may be performed between automatic systems and devices as well as individual users. Other intelligent network devices may also be utilized within the cloud system 114.

The servers 116 and databases 118 may represent a portion of the data platform 120. In one embodiment, the servers 116 may include a web server 117 utilized to provide a website, mobile applications, and user interface (e.g., user interface 107) for interfacing with numerous users. Information received by the web server 117 may be managed by the data platform 120 managing the servers 116 and associated databases 118. For example, the web server 117 may communicate with the database 118 to respond to read and write requests. For example, the servers 116 may include one or more servers dedicated to implementing and recording blockchain transactions and communications involving the data 126, transactions 128, and advertisements 129. For example, the databases 118 may store a digital ledger for updating information relating to the user's data 126 and transactions 128 as well as utilization of the data 126 and transactions 128 to generate and communicate the advertisements 129. For example, the user's data 126 may be packaged in digital tokens that may be securely communicated to any number of relevant parties.

The databases 118 may utilize any number of database architectures and database management systems (DBMS) as are known in the art. The databases 118 may store the content associated with each user/consumer/purchaser which may specify an address, name, age, demographics, interests, family/friend information, biometric identifiers, payment information, permissions, settings, location, cause preferences, cause restrictions, and so forth. Any number of secure identifiers, such as inaudible tones, QR codes, serial numbers, or so forth may be utilized to ensure that content, personal, or transaction information is not improperly shared or accessed. The databases 118 may include all or portions of a digital ledger applicable to one or more blockchain transactions including token generation, management, exchange, and monetization.

The user interface 105 may be made available through the various devices 101 of the system 100. In one embodiment, the user interface 105 represents a graphical user interface, audio interface, or other interface that may be utilized to manage data, transactions, and other information. For example, the user may enter or update associated data utilizing the user interface 105 (e.g., browser or application on a mobile device). The user interface 105 may be presented based on execution of one or more applications, browsers, kernels, modules, scripts, operating systems, or specialized software that is executed by one of the respective devices 101.

The user interface 105 may display current and historical data as well as trends. The user interface 105 may be utilized to set the user preferences, parameters, and configurations of the devices 101 as well as upload and manage the data, content, and implementation preferences sent to the cloud system 114. The user interface 105 may also be utilized to communicate the advertisements 129 to the user. The devices 101 (e.g., displays, indicators/LEDs, speakers, vibration/tactile components, etc.) may present, play, display, or otherwise communicate the advertisements 129 visually, audibly, tactilely, or any combination thereof.

In one embodiment, the system 100 or the cloud system 114 may also include the data platform 120 which is one or more devices utilized to enable, initiate, generate, aggregate, analyze, process, and manage data 126, transactions 128, advertisements 129, and so forth with one or more communications or computing devices. The data platform 120 may include one or more devices networked to manage the cloud network and system 114. For example, the data platform 120 may include any number of servers, routers, switches, or advanced intelligent network devices. The data platform 120 may represent one or more web servers that perform the processes and methods herein described. The cloud system 114 may manage blockchain management of the data 126 utilizing blockchain technologies, such as tokens, digital ledgers, hash keys, instructions, and so forth.

In one embodiment, the logic engine 122 is the logic that controls various algorithms, programs, hardware, and software that interact to receive, aggregate, analyze, rank, process, score, communicate, and distribute data, content, transactions, alerts, reports, messages, or so forth. The logic engine 122 may utilize any number of thresholds, parameters, criteria, algorithms, instructions, or feedback to interact with users and interested parties and to perform other automated processes. In one embodiment, the logic engine 122 may represent a processor. The processor is circuitry or logic enabled to control execution of a program, application, operating system, macro, kernel, or other set of instructions. The processor may be one or more microprocessors, digital signal processors, application-specific integrated circuits (ASIC), central processing units, or other devices suitable for controlling an electronic device including one or more hardware and software elements, executing software, instructions, programs, and applications, converting and processing signals and information, and performing other related tasks. The processor may be a single chip or integrated with other computing or communications elements.

The memory 124 is a hardware element, device, or recording media configured to store data for subsequent retrieval or access at a later time. The memory 124 may be static or dynamic memory. The memory 124 may include a hard disk, random access memory, cache, removable media drive, mass storage, or configuration suitable as storage for data 126, transactions 128, instructions, and information. In one embodiment, the memory 124 and logic engine 122 may be integrated. The memory 124 may use any type of volatile or non-volatile storage techniques and mediums. In one embodiment, the memory 124 may store a digital ledger and tokens for implementing a blockchain processes.

In one embodiment, the cloud system 114 or the data platform 120 may coordinate the methods and processes described herein as well as software synchronization, communication, and processes. The third-party resources 130 may represent any number of human or electronic resources utilized by the cloud system 114 including, but not limited to, businesses, entities, organizations, individuals, government databases, private databases, web servers, research services, and so forth. For example, the third-party resources 130 may represent advertisement agencies, marketers, e-commerce companies, verification services, credit monitoring services, blockchain services, payment providers/services, and others that pay for rights to use the data 126, track or provide information regarding the transactions 128, and create or monitor utilization of the advertisements 129.

In one embodiment, the data platform 120 may implement a blockchain ledger, manager, or technology. In another embodiment, the blockchain ledger may be accessible through sources 131. Any number of existing, developing, or future blockchain technologies, companies, or providers may be utilized (e.g., Aeternity, Ethereum, Bitcoin, Dfinity, ContentKid, Blockphase, Chain of Things, Flowchain, Decissio, Cognate, SkyHive, Safe, SALT Lending, Gemini, Circle, Coinbase, Chronicled, IBM, Voatz, Steem, Shipchain, etc.).

The blockchain is utilized as a way to store and communicate the data 126, transactions 128, and advertisements 129. The blockchain may utilized one or more distinct ledgers for different entities, services providers, types of data, users, or so forth. For example, each new user with data received by the data platform 120 is assigned a token or other secure identifier. In one embodiment, the digital tokens may be managed utilizing a key that allows the user or controlling party to access the ledger. In one example, the tokens may be controlled by the user or control may be reassigned. The blockchain may cross-reference updates to the data 126 with the original record for the data platform 120 to ensure proper maintenance, control, licensing, management, and transactions. In one example, different licensing tiers, pricing algorithms, license verification, cause information, and payments are combined to create a unique platform. The illustrative embodiments provide a system 100, cloud system 114, and data platform 120 for using user data, specifically stocks, equities, ownership, holdings, and interests, to generate selective or targeted advertising. The illustrative embodiments are performed based on the user's request, authorization, or approval to apply with all applicable laws.

The blockchain may also utilize any number of payment systems (e.g., PayPal®, Venmo®, Dwolla®, Square®, wire transfers, credit cards, Quicken®, etc.) to receive money and distribute payments to the applicable party. In one embodiment, the data platform 120 may receive a small fee or percentage per transaction, data uploaded/updated, data purchased, shared, or licensed, purchased item, browsing session, or so forth. In one embodiment, the data platform 120 may be utilized to verify users and advertisers (as well as other users/entities that utilize the data platform 120) and associated data 126 and transactions 128 associated with the data 126.

The third-party resources 130 may represent any number of electronic or other resources that may be accessed to perform the processes herein described. For example, the third-party resources 130 may represent government, private, and charitable servers, databases, websites, programs, services, and so forth for verifying the data 126, transactions 128, and the advertisements 129. In another example, auditors may verify the advertisements 129 are actually generated based on the data 126 including the transactions 128.

Various data and venue owners that access the data platform 120 may legally extract and tokenize the data 126, transactions 128, and advertisements for use in the exchange provided by the system 100 by identifying and tracking data utilizing automatic data extraction tools. Any number of privacy and data policies may be implemented to ensure that applicable local, State, Federal, and international laws, standards, and practices are procedures are met.

In one embodiment, a user or consumer group represented by a user of the devices 101 or the sources 131 may elect and receive permission to collect observational data collected from secure and authorized systems to achieve access to partial or complete data from the sources 131 (e.g., professional drivers, human resources, prison records, property values, property square footage, real estate sales, retail sales, retail prices, purchase data, stock ownership, commerce, waste stream data, etc.).

The logic engine 122 may also perform valuation of the data 126 and advertisements as is taught by U.S. provisional patent application 62/755,815 entitled "Method and System for Data Valuation and Secure Commercial Monetization Platform" and filed Nov. 5, 2018 and corresponding PCT/US19/59920 filed Nov. 5, 2019 and as is taught by U.S. provisional patent application 62/826,457 entitled "Method and System for Data Futures Platform" filed Mar. 29, 2019 and corresponding PCT/US20/25495 filed Mar. 27, 2020 which are hereby incorporated by reference in their entirety. The illustrative embodiments may also support third-party utilization of the data 126 and transactions 128 to generate the advertisements 129. Various authorization, auditing, and validation processes may be performed by auditing groups, commissions, industry groups, or other professionals/entities. The various embodiments may also allow a user to donate the value of their data 126 and transactions 128 and consumption of advertisements 129.

In one embodiment, the logic engine 122 may utilize artificial intelligence. The artificial intelligence may be utilized to enhance data 126, analyze transactions 128, and generate advertisements 129 to increase value, utilization, effectiveness, and profits. For example, artificial intelligence may be utilized to review, authenticate, and validate data and transactions that are received by the system 100. The artificial intelligence of the logic engine 122 may be utilized to ensure that the data 126 is improved, accurately analyzed, and value increased. For example, it is expected that data and the associated tokens that are validated utilizing artificial intelligence may be given a premium value by advertisers.

In another embodiment, the devices 101 may include any number of sensors, appliances, and devices that utilize real time measurements and data collection to update the data 126. For example, a sensor network, wearables (e.g., watches, bands, implantable devices, etc.) and Internet of things (IoT) devices may gather user and behavioral data. The data platform 120 may also work in conjunction with hands-free data mining and measurement tools that tracks location, activity, and video-based marketing data (e.g., from GPS location, video from storefronts, beacon detection, proximity alerts, etc.) from any number of third-party sources. The user may be tracked through any number of environments, locations, and conditions. The advertisements 129 may also be generated based on the activities, actions, and location of the user.

In one embodiment, the data platform 120 may extract data from third-party platforms by opting in and providing user credentials to various applications (e.g., Charles Schwab, TD Ameritrade, E*Trade, Vanguard, Fidelity, Merrill Lynch, etc.) the data platform 120 may extract data from the sources 131.

Figure 2:
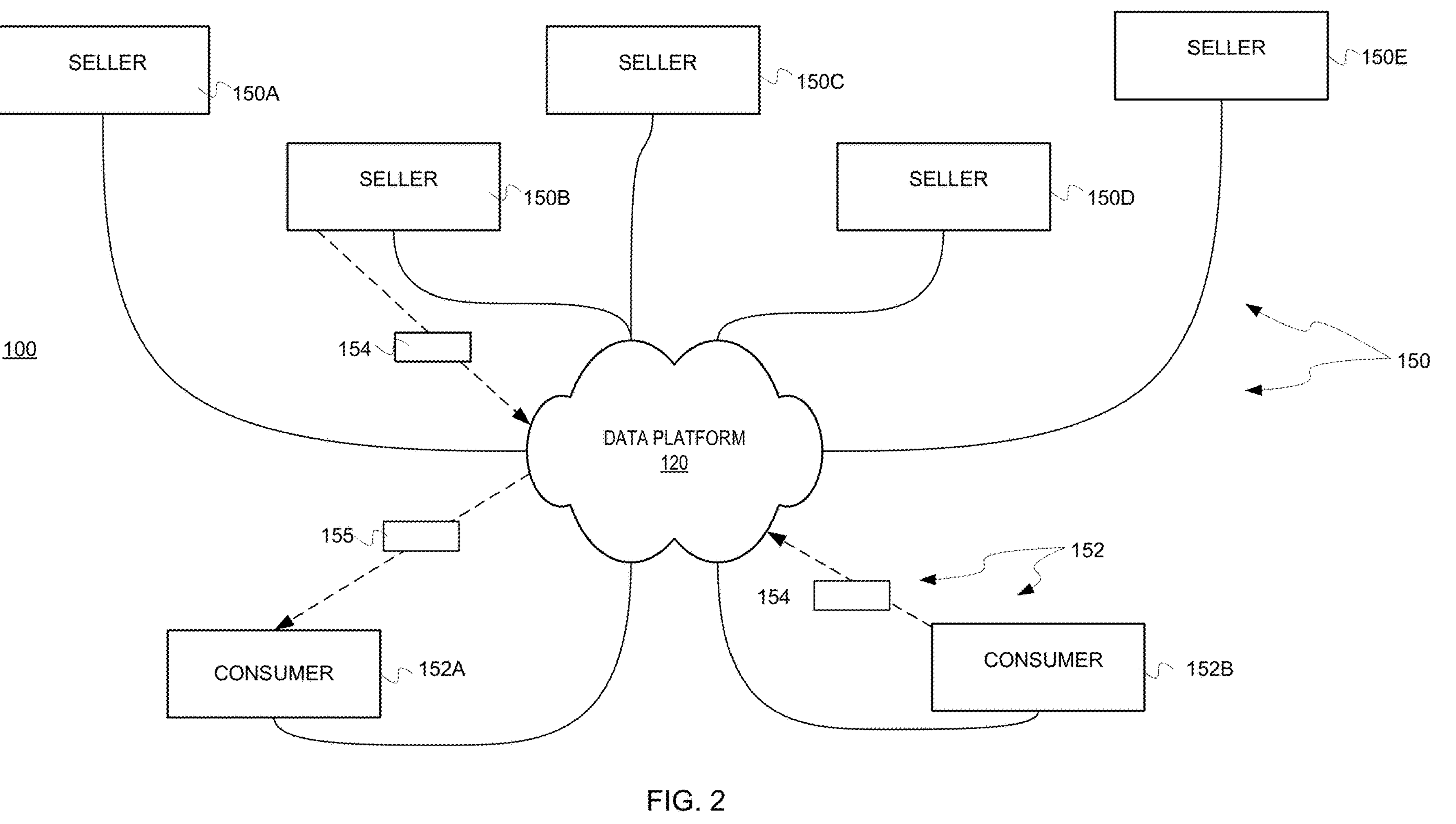
FIG. 2 further illustrates portions of the system of FIG. 1 in accordance with an illustrative embodiment.

FIG. 2 further illustrates portions of the system 100 of FIG. 1 in accordance with an illustrative embodiment. As shown the sellers 150A-E (jointly sellers 150) may represent the sources 131 of FIG. 1. The sellers 150 may represent any number of exchanges, platforms, clearinghouses. advertisers, marketers, businesses, retailers, service providers, individuals, organizations, entities, or so forth referred to as sellers 150 or businesses for purposes of simplicity. The consumers 152A, 152B (jointly consumers 152) represent any number of users, consumers, groups, or individuals that have data 154 (also including transactions) that is utilized to allow targeted advertisements 155 to that they are willing to allow the sellers 150 to access through the data platform 120. In one embodiment, the data platform 120 may represent all or portions of the system 100 of FIG. 1 (including the cloud system 114, servers 116, and databases 118).

The consumers 152 may actively or passively upload data 154 to the data platform 120. The data platform 120 may also receive amended, updated, or add additional data 154 for the consumers 152 at any time as described herein. The consumers 152 may have an agreement (e.g., contract, terms of services, permissions, authorizations, etc.) for the utilization of the data 154 by the sellers 150 or other interested parties to generate the targeted advertisements 155. The agreement or contract may specify how, when, and what portions of the data 154 may be used as well as the associated compensation terms. The agreement may specify that the data 154 may be processed, analyzed, purchased, licensed, rented, leased, or otherwise managed by the data platform 120 for the mutual benefit of the consumers 152 and the sellers 150. For example, the consumer 152B may elect to receive targeted advertisements 155 to support the companies, organizations, entities, or other groups in which the consumer 152B has stock, ownership shares, interests, holdings, or a vested interest. The consumer 152B may be interested in the targeted advertisements 155 to support herself or to support family and friends. In another example, the consumer 152B may elect to license use of their data 154 such that they are compensated utilizing a digital currency (or hard currency) for each access of or utilization of their data 154 by the sellers 150.

The data platform 120 may process raw consumer data to generate the targeted advertisements 155. The targeted advertisements 155 may be desirable to the user because the targeted advertisements 155 support the companies, stock, holdings, ownership, or interests of the user. In one embodiment, a term or logo utilized with each of the advertisements may indicate that the targeted advertisements are for the benefit of the user. In one embodiment, the targeted advertisement 155 may even include the stock ticker, name of the company, user's name, key word, identifier, certification, or so forth indicating that the targeted advertisement has gone through the analysis, authorization, and vetting process herein described.

The data platform 120 performs valuation of the data 154 and targeted advertisements 155 based on information from any number of sources including current rates, contracts, indices, exchanges, and other applicable information. For example, current targeted advertisement rates may be utilized to value the data. The tokens paid to the consumers 152 in exchange for the data 154 may vary based on the volume, quantity, verification, and types of information included in the data 154. The data platform 120 normalizes data monetization for the consumers 152 and sellers 150. Compensation performed by the data platform 120 may be performed utilizing digital currencies or hard currencies. In one embodiment, blockchain-based currencies may be utilized to compensate the consumers 152. Full tokens or partial tokens may be utilized to represent the values most accurately being exchanged. There may be a predefined number of tokens available thereby allowing early adopters of the system 100 to earn more over time. For example, in response to the consumer 152A selling or granting access to the data 154 to the data platform 120 or the seller 150B, the consumer may be compensated with tokens (e.g., Bitcoin, Ethereum, proprietary tokens, etc.). All or portions of the data 154 may be involved in a transaction. For example, in addition to stock, ownership, equities, and interest, the data 154 may include numerous components relating to all aspects of the life, work, hobbies, entertainment, studies, politics, health, family, consumer habits, for the consumer 152B. Not all of the sellers 150 may sell products, goods, or services that correspond to the stocks, holdings, and interests of the consumers 150. The seller 150D may only license rights to temporarily (e.g., for a single session, activity, timer period—day, week, year, or custom amount) access the consumer habits of the consumer 152B existing and updated in real-time. The exchange for the tokens may include a pointer to a secure storage or vault accessed through the data platform 120. The pointer may be an encryption key, access information, unique identifier, or other security information for accessing the data 154 associated with the user. In another embodiment, security tokens used for the blockchain may also be embedded with the data 154. The tokens granted through the data platform 120 may vary in value, may be fixed, or may act similar to other monetary instruments (e.g., stocks, bonds, certificates of deposit, etc.) for a specified original value of the data 154.

The data platform 120, sellers 150, or consumers 152 may keep and maintain digital ledgers that track the transactions within the system 100 to verify and authenticate the data 154, advertisements 155, and associated transactions. The sellers 150 may utilize the data 154 to advertise, sell, or market goods, services, products, perform market research, generate analytics, and otherwise generate and communicate the advertisements 155 and communicate the advertisements 155 to the consumers 152. As previously noted, the data platform 120 may also represent one or more processing, analysis, blockchain, or distribution centers, systems, devices, facilities, or so forth. The sellers 150 and consumers 152 may represent any number of individuals or groups (e.g., hundreds, thousands, millions, etc.).

As noted, the sellers 150 may send or distribute goods and services associated with the advertisements 155 through the cloud system or directly to the consumers 152. In one embodiment, the seller 150B may distribute goods and services to the consumer 152A through the data platform 120. The data platform 120 may perform distribution of the data 154, targeted advertisements 155, and/or goods and services. For example, the data platform 120 may include any number of physical storages, digital storage, warehousing, and distribution systems, facilities, professionals, employees, contractors, electronics, and so forth.

The data platform 120 is unique in the way that data is tracked and utilized. Existing systems do not allow a user to control how and when their data is utilized. Most users are unable to monetize their data as it is utilized by search companies, social media companies, online retailers, and others. The platform and implemented methods provide a unique and transparent manner to track data of a user and utilize the data. The interactions between consumers 152 and the sellers 150 through the data platform 120 is unique and mutually beneficial. The illustrative embodiments provide the system for better tracking data (e.g., data packets, files, content, etc.) that may be subsequently utilized to update advertisements and marketing that is presented to the consumers 152 by the sellers 150 (or other parties).

The system 100 and data platform 120 may be a unique portion of a blockchain system that enables for user data to be securely accessed through tokens that may be created, modified, vended, and otherwise transacted.

Figure 3:
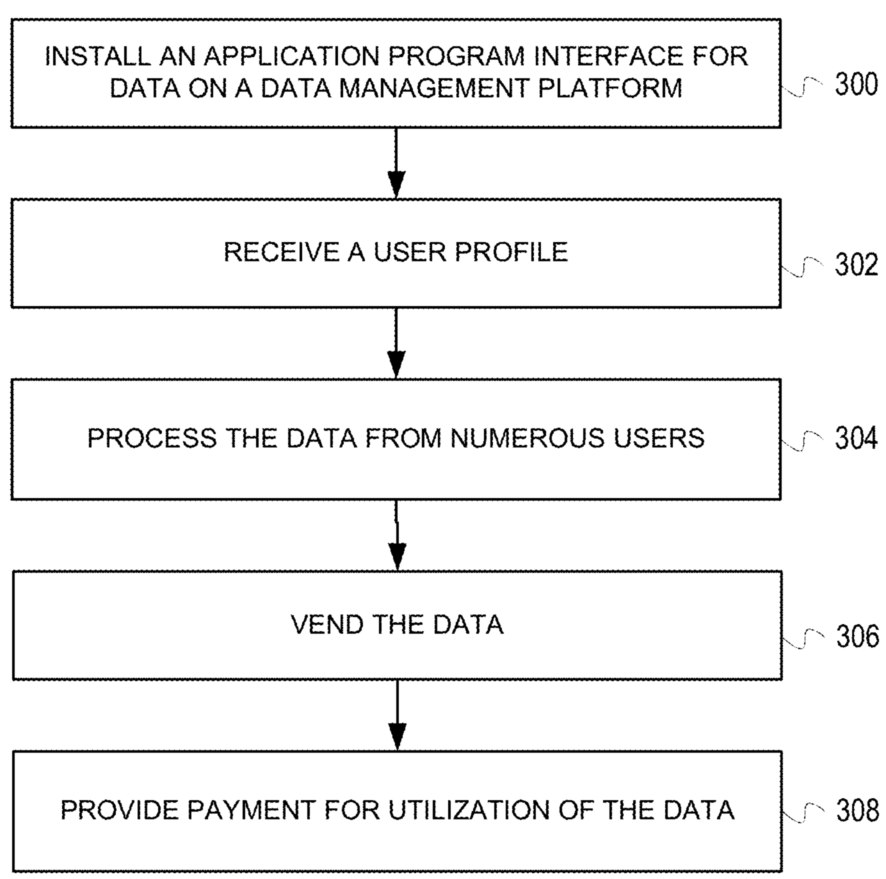
FIG. 3 is a flowchart of a process for vending data in accordance with an illustrative embodiment.

FIG. 3 is a flowchart of a process for vending data in accordance with an illustrative embodiment. The process of FIGS. 3-7 may be performed by a platform, device, server, or other equipment in accordance with illustrative embodiments (see for example the devices, servers, systems, and equipment of FIG. 1). All or portions of the steps or processes of FIGS. 3-7 may be performed automatically (without user interaction). The process of FIG. 3 may be implemented by a system or platform, such as the system 100, data platform 120, or devices 101 of FIG. 1 referred to generically herein as the platform. The steps of FIGS. 3-7 as well as the systems, devices, and components of FIGS. 1, 2, 8, and 9 may be combined in any order, integrated, or otherwise combined as useful.

The process of FIG. 3 may begin by installing an application program interface for data on a data management platform (step 300). The application program interface (API) may be installed or integrated with any number of platforms, programs, or so forth, such as a data management platform. The API may also be any number of software programs, scripts, modules, sets of instructions, or so forth. In one embodiment, the API is integrated with a web browser as an add-in, extension, application, or other interface. For example, the API may be integrated with a search tool (e.g., standalone, browser-based, network managed, etc.). The API may be utilized by individuals, corporations, data exchange companies to enhance their data protection and data management and monetization strategy. The API may also be installed on other electronics devices, such as personal computers, tablets, mobile devices (e.g., smart phones, tablets, etc.), gaming devices, streaming devices, virtual reality/augmented reality devices, and so forth. The illustrative embodiments are an improvement over existing technologies because they provide user control of personal and online data for the purpose of monetization by the data owners.

Next, the system receives a user profile (step 302). The user profile may represent an individual, family, group of individuals (e.g., friends, clubs, associates, etc.), company, organization, or entity and may be referred to generally as a "user profile" or "data profile." For example, a user profile may be created for a user. The data profile may also include user preferences, settings, parameters, and other applicable information that control what, when, and how data may be collected, shared, and monetized. The user profile may be generated or determined from already available information for the user. For example, the user profile may represent one or more profiles compiled by devices, accounts, services, or so forth. The user may provide answers utilizing one or more surveys, fields, questions, or other applicable information and data to determine applicable information and data. The user profile may also represent the other profiles herein described.

Next, the system processes the data from numerous users (step 304). In one embodiment, the numerous users may be associated with the other user through familial relationships, friendship, organizations, business entities, or other associations. The user and numerous users may be bound by law/regulation, agreements, consent, or so forth. The data may be processed by adding, confirming, modifying, reconfirming, and authorizing data according to the user profile. In one embodiment, raw data may be converted into data objects. For example, user purchases may be created to specify that the user has children 10, 12, and 16 with interests in specified sports, gaming, mobile devices, and camping. The illustrative embodiments may utilize artificial intelligence or machine learning to perform processing and segmentation of the data during the data collection process. The data may be raw, partially processed, structured, or unstructured as utilized and monetized. The data herein described may be transformed from raw data into data objects, sets, and profiles tied to real world and digital assets.

In one embodiment, during step 304, the data may be associated with a unique security token that points to or includes the data. The data may include new, added, modified, or updated user data or profile objects, such as consumer interest, sharing of personal plans, likes and dislikes, opinions, social media feeds, purchases, preferred retailers, products and services of interest, and other similar information.

Next, the system vends the data (step 306). The tokens may grant access to the data. Full or partial tokens may be included in transactions. The tokens may be involved in transactions by advertisers, brands, corporations, and any entity who values or requires access to data to enhance their brand reached. Tokens may be passed from these parties to consumers/users in exchange for access to their data. The tokens may be distributed each time a user associated with a data object participates in sharing, updating, exchanging, or selling the data. The illustrative embodiments provide the ability to band multiple variable priced micro fractions of tokens for each single or new data point/object. The platform may also band a single higher value token to represent and monetize a large exchange of data (e.g., objects, sets, profiles, pool(s), etc.).

Next, the system provides payment for utilization of the data (step 308). The system may track the fluctuating value of the data points, sets, and pools (all referred to as "data"). The system may ensure that users receive optimal compensation and monetization of their data. User may be paid in hard currency (e.g., American Dollars, British Pounds, Mexican Pesos, etc.), digital currency, discounts, services, rebates, or so forth. The purchasers of the tokens/and associated data may offer users micro fractions of a tokens market value in exchange for access to advertiser desired data profile elements. The described systems and methods allow data to be monetized even if not fully utilized by the user (e.g., company, individual, entity, etc.). As a result, the user may be able to create new or enhanced revenue streams from latent data that may be collected as a byproduct of their business. The illustrative embodiments may provide a method of utilizing data that satisfies user, legal/privacy, and industry standards as well as securing the data against unwanted access or intrusions.

Figure 4:
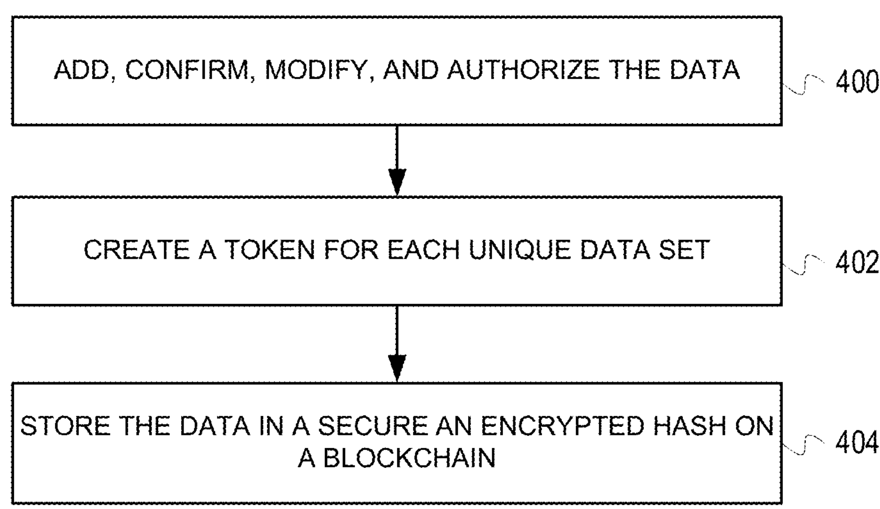
FIG. 4 is a flowchart of a process for storing data in accordance with an illustrative embodiment.

FIG. 4 is a flowchart of a process for storing data in accordance with an illustrative embodiment. The process of FIG. 4 may begin by adding, confirming, modifying, and authorizing the data (step 400). At any time, different data objects may be added. The data may be added as individual elements, sets, profiles, and pools. The platform may be added, confirmed, modified, and authorized as structured or unstructured data.

Next, the system creates a token for each unique data set (step 402). The tokens may point to a single data object/element, data sets, data profiles, or data pools. The illustrative embodiments allow for the tokenization of a real-world or digital asset for the purpose of implementing micro-fraction ownership of the corresponding asset. The tokens may then be involved in any number of transactions involving numerous parties.

Next, the system stores the data in a secure and encrypted hash on a blockchain (step 404). In one embodiment, an encrypted hash on the blockchain may be utilized to store the data (e.g., data objects, data sets, data pools, etc.). Although reference is made to utilizing a blockchain system, the illustrative embodiments may also utilize other secure storage techniques, such as encrypted databases, secured servers, and so forth. The hash may link to the data that is stored in a secure location.

Figure 5:
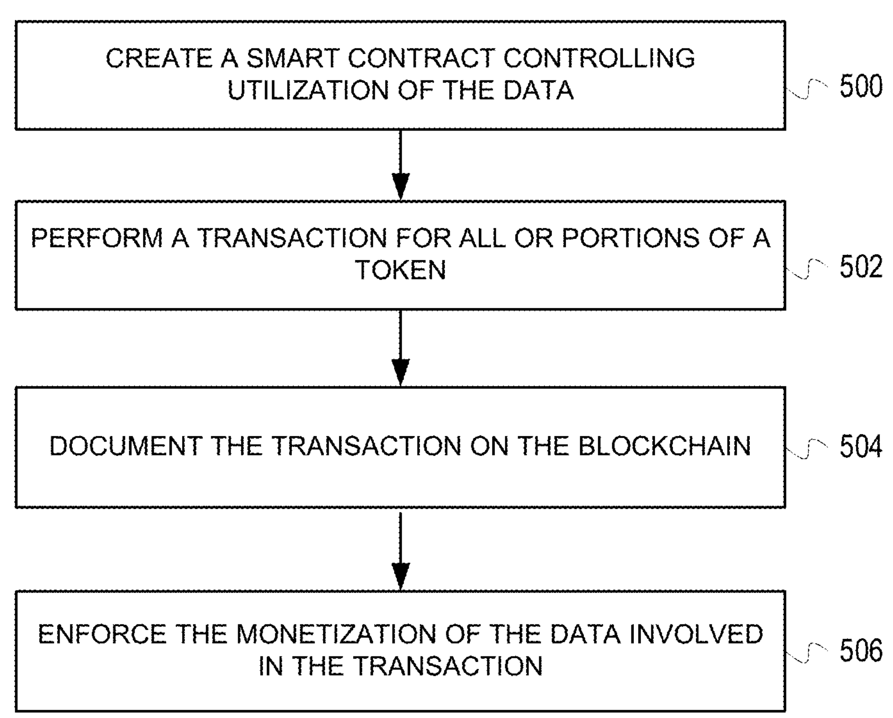
FIG. 5 is a flowchart of a process for monetizing data in accordance with an illustrative embodiment.

FIG. 5 is a flowchart of a process for monetizing data in accordance with an illustrative embodiment. The process of FIG. 5 may begin by creating a smart contract controlling utilization of the data (step 500). The smart contract may be created based on the requirements of the user and potential purchasers (e.g., advertisers, corporations, etc.). The smart contract governs how the user is compensated for transactions involving the data. The smart contract may also specify the rights granted to a token holder. The legal rights, permissions, binding terms, and other information may be specified by the smart contract. In one embodiment, the smart contract controls how the data is utilized and monetized. The price of the data may be governed by free market valuations. Alternatively, the smart contract may set price maximums and minimums. In one embodiment, the smart contract may allow for the geographic utilization of the data. For example, the data may be of value for location-based targeting to interested parties (e.g., neighborhood, region, city, state, etc.). User preferences set by the user may set permissions, settings, limitations, thresholds, and requirements implemented as part of the smart contract.

Next, the system performs a transaction for all or portions of a token (step 502). The platform may include or represent an exchange. As noted, full tokens or partial tokens of any size may be involved in transactions. For example, fractional or micro share of the tokens may be involved in the transactions. The purchase or exchange of tokens may provide a party access to the data associated with the token. Transactions may be performed through the system that measures and values the tokens, data, and other transaction components in real-time. The transaction may include any number of markets, limit, stop, short, option, or futures transactions or orders. For example, the transaction may be performed based on a price that is predetermined or determined in real-time or determined at the time of transaction of the data from the seller to purchaser.

Next, the system documents the transaction on the blockchain (step 504). In one embodiment, the transaction may be recorded on the ledger associated with the blockchain. The transaction may also be recorded utilizing any number of databases or so forth.

Next, the system enforces the monetization of the data involved in the transaction (step 506). In one embodiment, the monetization of the data and associated transaction involved in the transaction may be governed by the smart contract.

Figure 6:
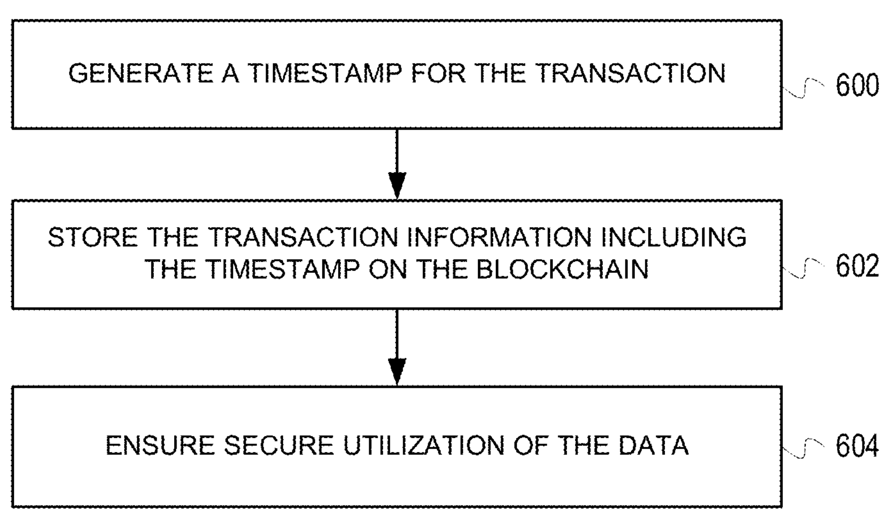
FIG. 6 is a flowchart of a process for documenting a transaction in accordance with an illustrative embodiment.

FIG. 6 is a flowchart of a process for documenting a transaction in accordance with an illustrative embodiment. The process of FIG. 6 may begin by generating a timestamp for the transaction (step 600). The transaction may be timestamped utilizing any number of standards. In one embodiment, the transaction is marked in a blockchain logo in Unix/Epoch time which is the time 00:00:00 UTC on Jan. 1, 1970 minus leap seconds. An Epoch timestamp may provide a universal time stamp that is searchable, accessible, readable, and recognizable across locations, time zones, and so forth. Accurate time keeping is required to ensure that transactions are properly documented to ensure accurate valuations, ownership, transactions, and monetization of the tokens and associated data. For example, the utilization of Epoch/Unix timestamps may allow for greater reliability when retrieving a datapoint associated with the transaction.

Next, the system stores the transaction information including the timestamp on the blockchain (step 602). As part of this process, a new block of information may be added/chained together. For example, once new data comes in the data is entered into a fresh block. Once the block is filled with data it is changed on the previous block, which makes the data chained together in chronological order.

Next, the system ensures secure utilization of the data (step 604). The data may be accessed utilizing a key or identifier included in the token. As previously noted, the data may be de-identified or disassociated from the user to prevent identity theft, hacking, or any other unwanted usage of the user's data.

The illustrative embodiments may be utilized to create corporate and consumer data estates. Corporation, entity, group, family, or user may be tokenized as a data estate. The data grouping of the estate may include each data profile element with a single profile and corporation data profile, groups of data profiles, and token-based micro shares tied to data points, data objects, data sets, data pools, data visualizations, and data estates. Artificial intelligence may be utilized to verify the data is current and complete. The single and groups of data profiles may be ranked by value and desirability. Data estates may be similarly involved in transactions and monetized as is herein described.

The decentralized nature of the illustrative embodiments including utilization of blockchain technology may allow any currency to be exchanged for access to data. As a result, the existing pay per click (PPC), pay per view (PPV), cookie targeting, or other existing models may become obsolete. Many of these blind targeted advertising models are ineffective and costly to corporations or groups that purchase or access the data. The illustrative embodiments focus on data completeness by motivating users to provide accurate and real time data for enhanced value to advertisers. As a result, many of the best guess, blind, or implied processes are not optimally utilized for ad generation and targeting. The value provided by the data refinery, data vault, and data exchange may lead to higher conversion rates over standard advertising and marketing campaigns that utilize generic digital format website advertisements.

The data valuation and monetization system and methods herein described are also disruptive because they give profile owners visibility and control over which companies, groups, entities, or individuals are authorized to access their data and which parties are blocked access. For example, a whitelist and a blacklist may be utilized to specify the parties that have full, limited, or no access to the data. As a result, blocked parties are prevented from participating in any transactions for tokens/data for which they are unauthorized.

The illustrative embodiments allow for the reduction or click-fraud events, wasted advertisements, and reduce the need to monitor ad network traffic for indications of bot or other fraudulent mechanisms used to falsely imply higher web traffic numbers, ad-clicks and ad-views on advertisements or targeted content further ensuring internet activity and consumer responsiveness to advertisements are genuine.

The illustrative embodiments also provide a platform for users to securely store their data in a data value that obscures unwanted access to their data. For example, the identifying information for the user may be disassociated from their data and profile. As a result, user profiles and data may be more freely shared with approved advertisers, brands, marketers, and others and lessens the need for those parties to focus revenue on blind and behavioral targeting that historically has exceptionally low conversion rates.

The illustrative embodiments provide a methodology to define and value user data by measuring user engagement and data verification, date profile completeness, profile data point saturation, data point marketability, data point desirability and market specific data. The platform may also indicate that specific data has become less or more desirable and may indicate when data is static, non-static, ever changing or perennial, or less desirable through the utilization of the data platform and data marketplace.

In the illustrative embodiments, token purchases and payouts may be documented in smart contracts and stored on the blockchain. The smart contracts may be executed by users and parties (e.g., advertisers, marketers, analysts, researchers, etc.) who trade access to the data for a full or partial share of the token. Tokens may be exchanged between parties based on needs and desires. The data may be valued based on how often it is updated, modified, verified, and based on overall completeness.

Figure 7:
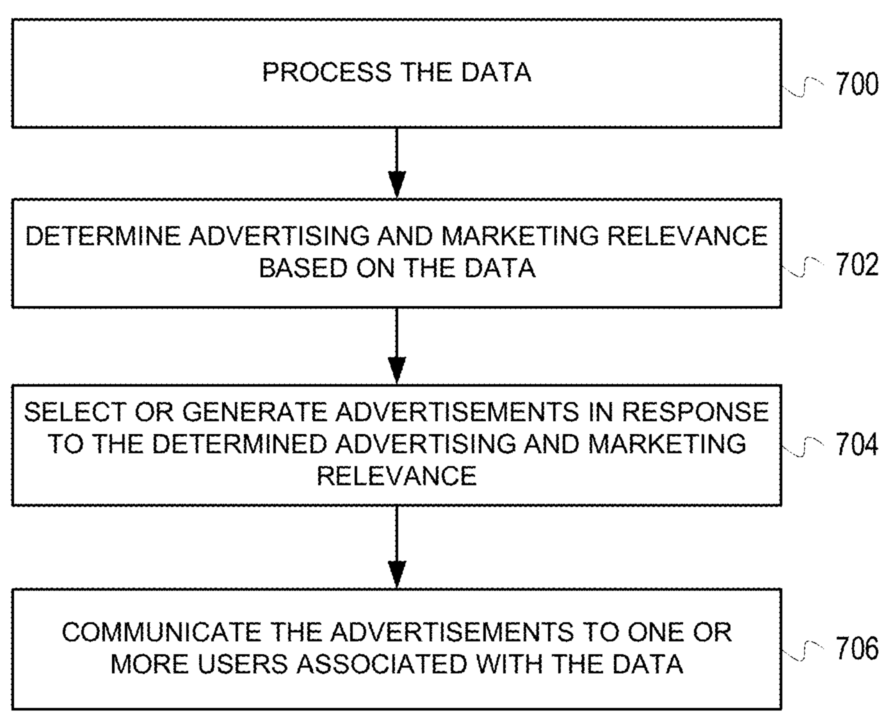
FIG. 7 is a pictorial representation of a platform for monetizing data in accordance with an illustrative embodiment.

FIG. 7 is a flowchart of a process for monetizing data in accordance with an illustrative embodiment. As previously described, the process may be performed by a special platform, system, device, equipment, or component. The process of FIG. 7 may begin by receiving one or more data components associated with user data of a user from one of a number of sources (step 702). The data components may represent various types of data, numbers, profiles, or other information associated with the user. The data component may also be referred to as data elements. The reference to the data components in FIG. 3 may represent one or more data components that are received in a session, simultaneously, sequentially, or concurrently. The data components may be received through any number of processes, devices, platforms, or so forth. For example, the data elements may be received through online applications, baskets of goods, paper receipts, or electronic purchases, video selections, point-of-sale, foot traffic, location, surveys, social media selections, web consumption and history, audio input, or devices, such as wireless devices, personal computers, e-books, digital assistants, vehicles, gaming devices, virtual/augmented reality systems, or so forth. The platform may also confirm the data component is applicable to the user and/or verifiably received from the user. In one example, as data is received, the user may ask a verification question, such as "is this Blair?" The platform may also utilize machine learning to recognize activities, programs, and behavior associated with each of a number of users that may utilize the electronic devices that are part of or in communication with the platform. The platform may also receive specific user input to confirm that data belongs to the user or originated from the user or their authorized activities. For example, the user may verify that the data component is accurate and resulted from actions, activities, selections (active or passive), opt ins, surveys, codes/passwords/pins, biometric recognition, feedback, or data of the user. In another example, the user may determine that the data component was not received utilizing approved methods or processes. As a result, the data component may be deleted or otherwise removed. The data component may not be incorporated into a larger data set, or a data profile associated with the user. The user maintains control over their data and how it is captured, managed, monetized, and otherwise utilized by themselves and third parties. Incomplete data sets may be marked as incomplete to request data sets for completion as needed.

Next, the platform creates on or more tokens based on the user data (step 704). In one embodiment, the token includes an indicator, such as a secure link, instructions, algorithm, key, secure identifier, or pointer that points to the user data. The indicator may also grant access to the holder/recipient to access the user data securely as an authorized party. In another embodiment, the token itself may include the user data. In other embodiments, a portion of the user data that is less personal may be included in the token and additional user data that is more personal may be linked to by the token.

Next, the platform stores the user data in a secure location (step 706). As noted, the user data may be stored with or separately from the one or more tokens. The user data may be stored in a secure server and/or database accessible through one or more networks. For example, a secure connection (e.g., virtual private network connection, encrypted connection, secure accounts, etc.) may be utilized between devices or systems to ensure the safe communication of the one or more tokens, user data, and other applicable information.

Next, the platform vends the user data to a party utilizing the one or more tokens (step 708). The party may represent one of a number of parties that have purchased, leased, rented, licensed, or otherwise legally acquired access to the one or more tokens and associated data. During step 708, the token may be transferred, or access may be granted. As previously noted, the user data may be made available to the party from the secure location utilizing an indicator included in the one or more tokens.

In another embodiment, the platform or a separate device may generate an advertisement in response to the user data. The advertisement may be generated on behalf of the party based on step 708. The advertisement may represent a physical, digital/electronic, temporary, remote display (e.g., billboard, store sign, etc.) or other advertisement, marketing, or information that may be presented to the user audibly, visually, tactilely, or through other techniques. For example, digital advertisements may be displayed through mobile applications, computer programs (e.g., browsers, search tools, etc.), or other mediums. The advertisements may also be displayed based on location or proximity.

Next, the platform compensates the user for vending the user data (step 710). In one embodiment, during step 710, the party may purchase the data or otherwise compensate a service provider, vending party, or user associated with the data. Any number of tracking processes may be utilized to ensure that all transactions are processed with money, currency (e.g., digital currency, physical currency, electronic currency, etc.) being exchanged or transacted. The user may be compensated based on a preset time period (e.g., day, week, month, year, etc.). The service provider, aggregator, intermediaries, or other parties may also be compensated as part of the process of step 710. The platform monetizes the data to ensure that the user is compensated for the receipt, analysis, processing, and utilization of the data. As previously noted, the user may elect not to receive earnings, payments, or the monetary benefit of the data being monetized. For example, the earnings (e.g., dollars, cryptocurrency, points, credit, discounts, etc.) may be donated, shared, used as a tax deduction, or otherwise distributed to charitable groups, organizations, individuals, and so forth.

The process of FIGS. 3-7 may be performed automatically by algorithms, programs, or instructions configured to determine the validity and authenticity of data components. The user may specify preferences for controlling how and when the data is utilized. For example, a granular level of authorization may include individual applications, companies, organizations, entities, and other permissions regarding who may access the data.

Any number of preparatory steps may be performed as part of the processes of FIGS. 3-7. For example, a user profile may be created for a user. The user profile may be generated or determined from already available information for the user. For example, the user profile may represent one or more profiles compiled by devices, accounts, services, or so forth. The user may provide answers utilizing one or more surveys, fields, questions, or other applicable information and data to determine applicable information and data.

Figure 8:
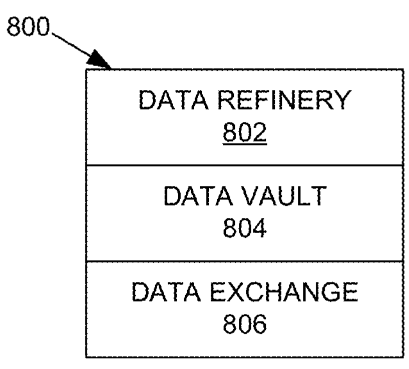
FIG. 8 is a pictorial representation of a platform for monetizing data in accordance with an illustrative embodiment.

FIG. 8 is a pictorial representation of a platform 800 for monetizing data in accordance with an illustrative embodiment. The platform 800 may include a data refinery 802, a data vault 804, and a data exchange 806. The platform 800 of FIG. 8 may be representative of one or more devices, such as the servers 116, data platform of FIG. 1, or other smart networked device implementing specific hardware, software, firmware, and/or sets of instructions. The platform 800 including the data refinery 802, data vault 804, and the data exchange 806 may function as separate platforms or an integrated platform.

The data refinery 802 is utilized to create data objects and capture applicable data to include the data objects. In one embodiment, the data refinery 802 may be positioned within the user's existing system to capture data that is already received, entered, gleaned, or otherwise determined by the existing system. The data object may be created to store all, portions, or types of data associated with the user (e.g., individual, couple, family, company, organization, group, entity, etc.).

The data vault 804 is utilized to securely store the data objects and add, modify, and improve the associated data. In one embodiment, the data vault may be utilized to collect, characterize, and value the data. The data vault 804 may also determine the pace at which new data objects are added or updated as well as the types of data. For example, the data vault 804 may determine that information relevant to two of the user's clients including company preferences for wireless services and legal services are added to the data vault 804 each day. The data vault 804 may be a physical or virtual storage and vault that securely stores information. In one embodiment, the data objects may be deidentified to remove identifying information to prevent hacking, identity theft, and other unwanted or prohibited utilization of data. The data vault 804 may also assign an initial value for the data object. The value may be associated with similar data, going rates, completeness of the data, the type of data, the user supplying the data, historical information, and so forth. The value may change at any time based on a determination of the platform 804 (i.e., the data vault or data exchange).

The data exchange 806 is utilized to price and perform transactions for the data objects. In one embodiment, the data exchange 806 creates a ticker associated with the data object. The ticker may be associated with the data object(s) for a user. The data exchange 806 allows the data objects to be priced and purchased. In one embodiment, the exchange may utilize secure tokens to access the data. For example, transactions involving the data may represent a key for accessing the purchased or leased data. For example, the tokens may include an encryption key, password, biometric, or other secure identifier for accessing the data object from the data vault or other stored location.

The platform may perform data reconciliation of the information at any time during the process. In one embodiment, a data reconciliation engine may review the applicable information to determine products/services that align with the data and interests of the user. In one embodiment, the platform may determine a portfolio of potential advertisements for goods and services associated with the user's data or interests. As a result, the advertisements, prompts, outreach, services, rewards, and so forth may be readily available in real-time or near real-time.

Likewise, at any time the platform may create targeted advertisements based on the user data. The targeted advertisements or marketing may represent any number of advertisements displayed to the user including Internet advertisements, in-application advertisements, television/video/Internet Protocol Television advertisements, radio/Internet radio, print advertisements, and other forms of advertisements and marketing. In one embodiment In one embodiment, advertising and marketing may be directed toward the user in response to a selection made by the user to opt-in to targeted advertisements that benefit the user's interests rather than random or blind targeted advertisements. For example, the selection may involve the acceptance of financial or legal language utilizing a graphical user interface presented utilizing a web interface, mobile application, or so forth. The selection may be used to receive highly targeted and user specific advertisements rather than generic advertisements or advertisements that are not associated with the user's data and interests. In one embodiment, a profile associated with the platform may specify the companies, organizations, entities, or other groups that the user would like to support. The user's profile may also include any number of settings, configurations, parameters, selections, releases, authorizations, verification requirements, or other information and data that controls how the user's data is utilized in accordance with the illustrative embodiments. The user referenced herein may also refer to one or more individuals, a group of people, an entity, an organization, associated persons, or so forth. The data may also be referred to as personal data, consumer data, private data, monetized data, authorized data, advertising data, or marketing data and may include individual data units, data sets, data pools, and other amalgamations or compilations of data, values, and information. The illustrative embodiments utilize blockchain and tokens because of the need for enhanced confidentiality and performance of data transactions.

The illustrative embodiments allow blocks of user data, vending data, transaction data, and other data and information described herein to be stored across a blockchain system, platform, or network. There is no single point of control or failure. User's data is secured so that access and utilization results in compensation directly or indirectly to the user in a way that has not happened before. The user, service providers, sellers, intermediaries, exchanges, platforms, managers, and/or other parties or devices may perform create, read, update, and delete operations on the data with an audit trail of the user data and utilization being tracked. As a result, validation, and reconciliation of all portions of the process may be performed effectively.

The illustrative embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible or non-transitory medium of expression having computer usable program code embodied in the medium. The described embodiments may be provided as a computer program product, or software, that may include a machine-readable medium having stored thereon instructions, which may be used to program a computing system (or other electronic device(s)) to perform a process according to embodiments, whether presently described or not, since every conceivable variation is not enumerated herein. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical, or other form of propagated signal (e.g., carrier waves, infrared signals, digital signals, etc.), or wireline, wireless, or other communications mediums.

Computer program code for carrying out operations of the embodiments may be written in any combination of one or more programming languages, including an object-oriented programming language such as Java, Smalltalk, C++, or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (e.g., through the Internet using an Internet Service Provider).

Figure 9:
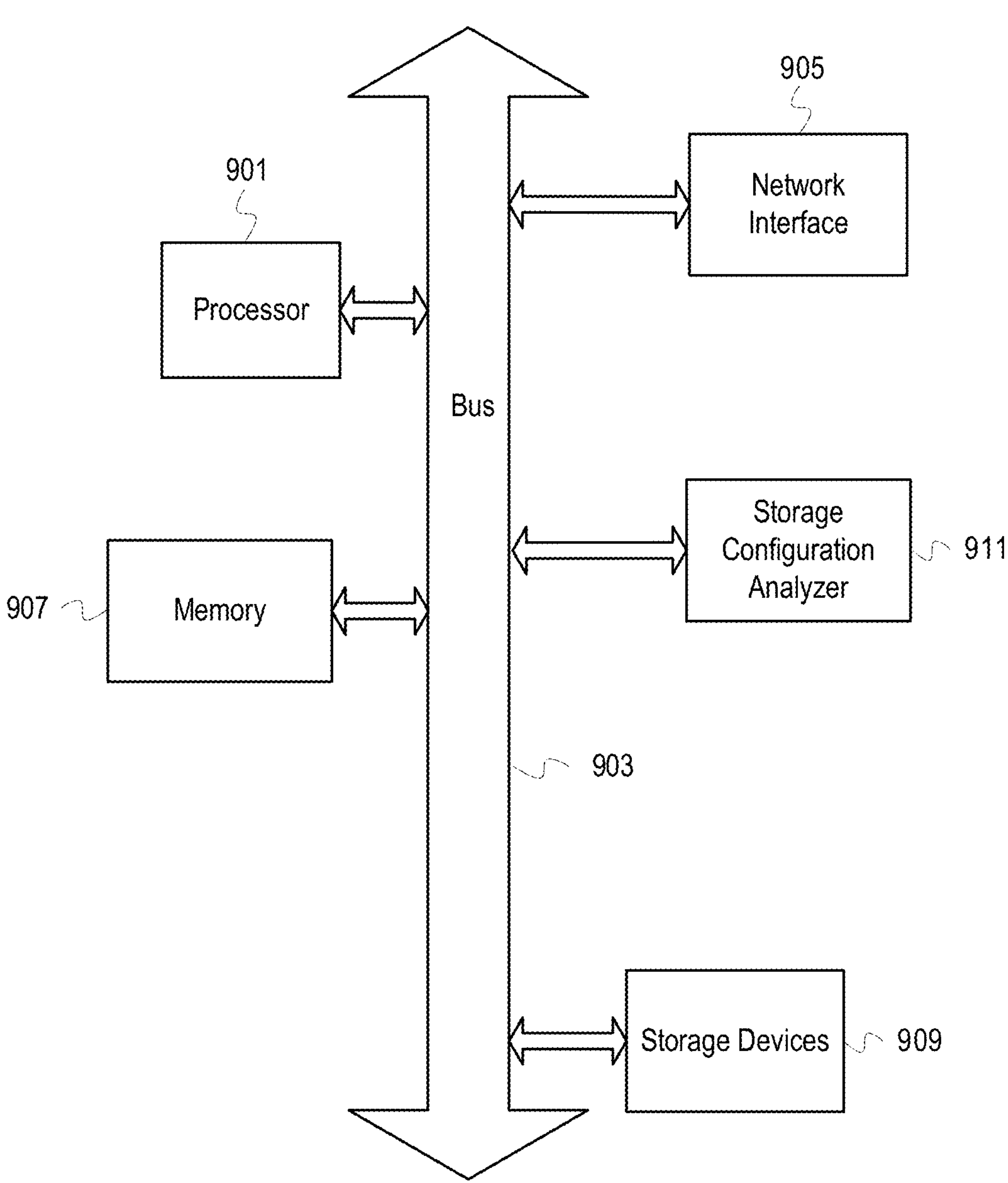
FIG. 9 depicts a computing system in accordance with an illustrative embodiment.

FIG. 9 depicts a computing system 900 in accordance with an illustrative embodiment. For example, the computing system 900 may represent a device, such as one or more of the devices 101 of FIG. 1. The computing system 900 includes a processor unit 901 (possibly including multiple processors, multiple cores, multiple nodes, and/or implementing multi-threading, etc.). The computing system includes memory 907. The memory 907 may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computing system also includes a bus 903 (e.g., PCI, ISA, PCI-Express, HyperTransport®, InfiniBand®, NuBus, etc.), a network interface 905 (e.g., an ATM interface, an Ethernet interface, a Frame Relay interface, SONET interface, wireless interface, etc.), and a storage device(s) 909 (e.g., optical storage, magnetic storage, etc.). The system memory 907 embodies functionality to implement embodiments described above. The system memory 907 may include one or more functionalities that store content, blockchain data, parameters, application, user profiles, and so forth. Code may be implemented in any of the other devices of the computing system 900. Any one of these functionalities may be partially (or entirely) implemented in hardware and/or on the processing unit 901. For example, the functionality may be implemented with an application specific integrated circuit, in logic implemented in the processing unit 901, in a co-processor on a peripheral device or card, etc. Further, realizations may include fewer or additional components not illustrated in FIG. 9 (e.g., video cards, audio cards, additional network interfaces, peripheral devices, etc.). The processor unit 901, the storage device(s) 909, and the network interface 905 are coupled to the bus 903. Although illustrated as being coupled to the bus 903, the memory 907 may be coupled to the processor unit 901.

The illustrative embodiments provide a system, method, device, and platform that utilizes a blockchain based system for tokenizing and monetizing consumer data, corporate data, financial data, accounting data, personal data, family history, DNA tracking, human resources, art, real-world objects, collections, memorabilia, content, media, music, files, and video content. In one embodiment, data related to book collections, music collections, record collections, art collections teaching lesson plans, music lessons, church sermons, prayers, and so forth may be objective and tokenized for the purpose of monetization or proof of ownership, sharing, licensing, or for insurance documentation purposes.

The platform provides a data and asset monetization methodology that transforms data, real-world objects, and virtual objects into tokenized data objects through a process that refines and objectifies profile data, corporate data, and real-world assets for the purpose of token-based monetization. This blockchain based data documentation and monetization platform covers a variety of real-world object and specific cloud and Internet-based data collection, valuation, and monetization methodologies.

The illustrative embodiments provide a platform that offers consumers, corporations, brands, services providers, and data aggregators, a complete data protection and monetization solution. The various embodiments may be utilized to objectify, tokenize, and track the value of data via the blockchain for the purpose of consumer and corporate data valuation and monetization.

The system, method, and platform may deidentify, document, objectify, tokenize, and provide enhanced user and corporate control over access to personal and corporate data. The platform may be utilized to mine data assets and is used across a wide range of consumer and corporate data pools. The data includes, but is not limited to core data, derivative data, data partnerships, data development, and provides data owners the ability to monetize any single data point or multiple data points, profile groups, or large sets of data or data profile pools.

The platform may be used to tokenize and monetize physical assets, such as real estate, property plant and equipment (PPE), square footage, capital, physical locations, mobile applications, accounts, contacts, property appraisal, data assets, corporate assets, inventories, art, collectibles, signs, furniture, receivables, and so forth. The platform may also be utilized to tokenize and monetize intangible assets, such as patents, copyrights, trademarks, leases, logos, brand names, brand positioning, computer programs, digital content, files, customer lists, franchise agreements, supply chain agreements, corporate owned assets, non-fungible assets, domain names, trade secrets, and other non-tangible, or semi-tangible assets. Intangible assets often provide the core of a company's competitive advantage and mark position and are often the key driver of a business' success.

In a corporate and accounting embodiment latent data may become tokenized data that may be used for the purpose of corporate data valuation and monetization, which can be used to identify and unlock internal unused or nascent data pools that add value to their corporate bottom line. Human Resources (HR) tokens also provide additional revenue streams through the creation of a tokenized data sets of latent data such as HR files, resumes, personnel files, accounting data, business plans, employee tax forms and so forth for similar companies. These tokens may be purchased by similar companies or companies looking for new employment data streams or for category indicators to identify industries where applicants are applying for work, high or low unemployment, income data, housing data, franchise data, competitive analysis, SWOT analysis, competitors' websites and customer experiences, competitors' market positioning, competitors' pricing, and current offers.

In one embodiment non-profits such as churches have their own data vault, which uses the tokenization process to tokenize each church and congregation as a tokenized asset. The creation and population of their data vaults, provides each church with the ability to create and determine the value associated with the data and tokenized asset value across all church owned real estate, and other physical owned church assets through an NFT valuation, and hard asset valuation tied to the tokenization process. Additionally, churches may generate passive income through the creation of prayer tokens. The platform may be used to provide an encryption process and data donation model where churches may accept donations for prayer requests or prayer donation requests in the name of a specific parishioner. The donations may also be used as contributions to the church in the name of the parishioner that the prayers are intended for. The prayer token may utilize a crypto technology and voice-over platform to capture the prayers and donations made. Now individuals in need of spiritual comfort may utilize crypto technology through the metaverse to access churches and prayers from their parish, from their religious leaders or from the Vatican—including the Pope, Cardinals, Bishops, Priests, and Parishioners—to offer choice prayers for real-time adoption. The same practice easily applies to the 10,000 distinct religions worldwide.

In the illustrative embodiments, the platform is linked to a user, corporate, corporate group (e.g., human resources, accounting, legal, research and development, business, management, etc.), organization, or other profile which may be secured and accessed via the platform. The profile may also be directly tied to the banking account associated with the profile for securely storing, documenting, tracking, and monetizing the value of the data. The platform may also pay a dividend (e.g., data, financial, etc.) through blockchain or through a consumer bank account based on the current market price of available tokenized data. The data may be more valuable if it is comprehensive, up-to-date, frequently updated, or so forth. The platform may incentivize users to update missing data elements to further increase the value of the data. For example, added data components may help create a more comprehensive data profile that helps advertisers, brands, corporations, and others improve advertising outcomes through increased advertising/marketing conversions, data utilization, and so forth.

The illustrative embodiments provide for enhanced refinement, valuation, and monetization of tokenized assets. The platform may be paired with the blockchain to connect consumers, brands, advertisers, retail, corporations, and other groups through real-world processes of aggregating, monetizing, and distributing data utilizing blockchain.

Advertisers, services providers, and others may reach, access, and utilize consumer or corporate data more effectively. Decentralized smart contract-based data and asset monetization may improve results for individuals, companies, creators, licensors, distributors, and others.

The various embodiments may utilize a deidentification process to further maximize how different types of data may be utilized. Smart contracts and blockchain management may be utilized to effectively monetize the different types of assets. The platform may utilize artificial intelligence and machine learning to provide recommendations for aggregation, utilization, or monetization of a tokenized data profile.

The platform may utilize a virtual private network to further provide software, secure communications, analytics tools, widgets, programs, apps, or widgets.

Figure 10:
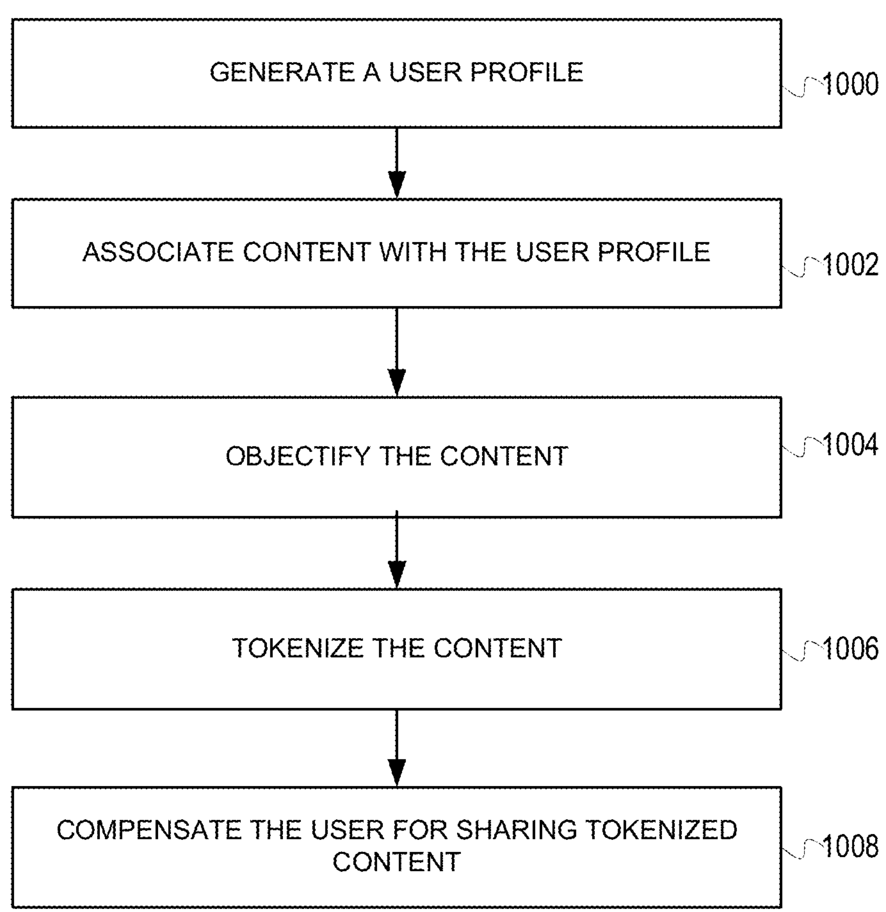
FIG. 10 is a flowchart of a process for creating content for compensation in accordance with an illustrative embodiment.

FIG. 10 is a flowchart of a process for creating content for compensation in accordance with an illustrative embodiment. The process of FIGS. 10-23 may be implemented by one or more devices, and platforms as herein described. As described, the various methods, flowcharts, steps, systems, platforms, and devices throughout may be combined, integrated, or utilized in any order. The data and content referenced herein may be created by any number of content creators (e.g., individuals, professionals, content creation employees, students, etc.), 3$^{rd}$ party content creators, fan-based content creators, and so forth.

The process may begin by generating a user profile (step 1000). The user profile may be generated based on information provided by one or more users. The users may represent individuals, families, corporations, organizations, businesses, groups, or so forth. The user profile may be automatically generated by one or more platforms. The user profile may specify how, when, where, and other details for how the data and content may be aggregated, processed, and monetized. The user profile may be updated or changed at any time by the user. Alternatively, user permissions, settings, parameters, and factors may be manually established by the user for the user profile.

The user profile may one or more secure profiles which may be secured and accessed via the platform or directly tied to the user's banking account for the purpose of securely storing, documenting, tracking, and monetizing the value of a consumer's data. The platform may also pay a data dividend on the blockchain or through a consumer bank account based on the current market price of available tokenized consumer data which may provide greater returns on data value when the available data is comprehensive. The platform may also incentivize users to update missing data elements that help advertisers, brands, potential employers, businesses, or others to increase conversions where the end result is a targeted purchase/sale of a brand targeted item or service.

Next, the platform associates content with the user profile (step 1002). In one embodiment, the user may create the content utilizing any number of devices (e.g., mobile phone, video camera, sound recorder, camera, screen capture equipment, etc.). As described herein, content may include various types of different data, files, content, or other information and data. The user profile may establish how, when, and under what conditions the content/data may be acquired, stored, managed, or otherwise utilized.

Next, the platform objectifies the content (step 1004). The platform may determine the type of data associated with the content, metadata, as well as associated information (e.g., capture data, upload data, associated activity, etc.).

Next, the platform tokenizes the content (step 1006). In one embodiment, the content may be associated with one or more tokens. The one or more tokens may be non-fungible or fungible tokens. For example, the content may be encapsulated as a non-fungible token. The content may include music, art, photographs, memes, that are incorporated in any number of files or formats that may be tokenized virtually or physically.

Next, the platform compensates the user for sharing tokenized content (step 1008).

Figure 11:
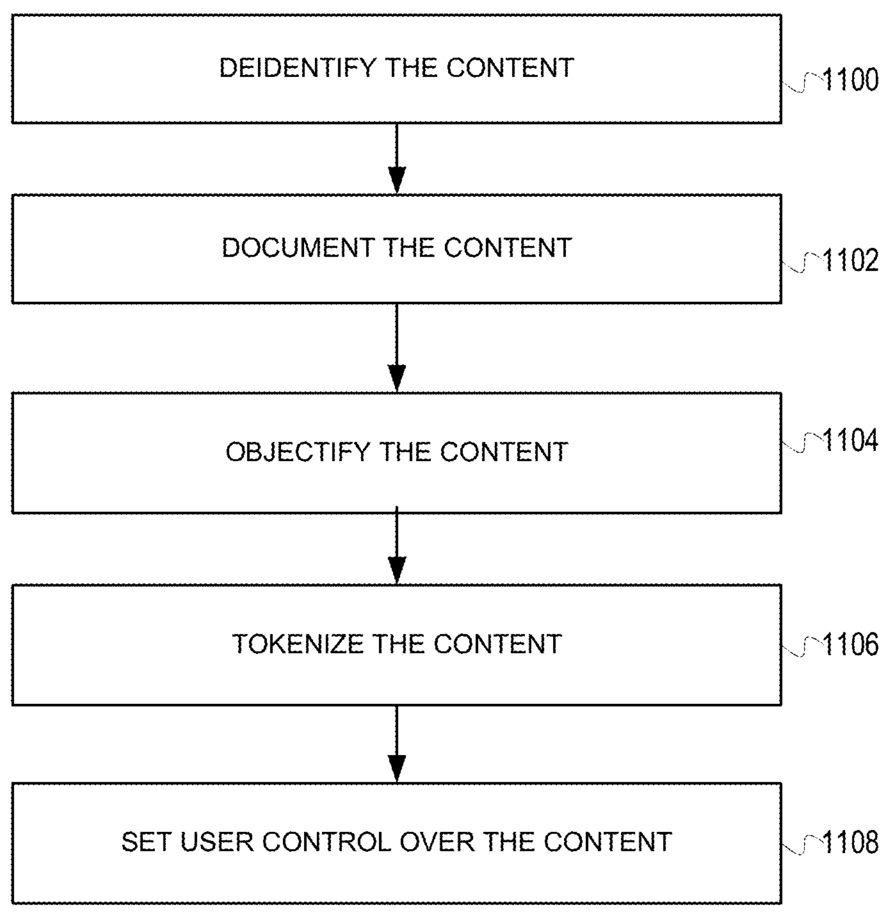
FIG. 11 is a flowchart of a process for processing for controlling content in accordance with an illustrative embodiment.

FIG. 11 is a flowchart of a process for processing for controlling content in accordance with an illustrative embodiment. The process may begin by deidentifying the content (step 1100). As previously noted, data, files, and other content may be referred to as content or data with specific implementations of each described more specifically. The content may be deidentified so that it may be utilized in ways that still protect the privacy and identity of the user. For example, the platform may comply with applicable local, State, Federal, and international laws, industry standards, and best practices relating to privacy of the user, such as the Health Insurance Portability and Accountability Act (HIPAA), children's online privacy protection act (COPPA), privacy acts (e.g., US Privacy Act of 1974, Gramm-Leach Bliley Act, etc.), the European Union General Data Protection Regulation (GDPR), and so forth. In one embodiment, the user's name, address, social security number, phone number, or other personally identifying information is removed from the content. In one embodiment, the personally identifying information is removed to enable broad utilization in a manner that protects the user. As noted, the content and data may correspond to various types of data (e.g., personal, purchase, corporate, gaming, health, hobbies/interests, etc.).

Next, the platform documents the content (step 1102). In one embodiment, the platform may save the content including all of the applicable data, files, and content in a digital ledger (associated with a blockchain technology), secured database, server, cloud storage system, or other secured location. The content may include documentation regarding how, when, and who may access the content as well as associated user/corporate profile information. For example, a secure pointer may be associated with the content. The saving may also be a separate step that may be performed. Documentation of content may be performed periodically, in real-time, based on event, happening, occurrence, transaction, or based on any number of other factors, conditions, settings, parameters, or so forth. In one embodiment, a virtual representation of the collected data may be stored on the blockchain and may be accessed by the data owner. For example, a virtual representation may be presented as a data visualization for the purpose of valuation, and monetization, providing the unique ability to better visualize data value in order to illustrate the value of each individual data point, data pool, data insights, utilization, and other collection or utilized data to give consumers/companies better insight and control over how, when, and who is able to monetize or utilize their content/data. Data may be presented as a data visualization utilizing a browser, program, mobile application, virtual reality, augmented reality, holographic, dedicated displays, audibly, tactilely, or utilizing a combination thereof. The platform provides a data marketplace and exchange to buy, sell, and trade data assets and physical/real world assets. The owners of the data may sell, lease, license, or perform other transactions for the data at any time.

Next, the platform objectifies the content (step 1104). During step 1104, the platform may determine the type of content and an associated category of content/data if applicable. The platform may denote the types, amounts, and details of the content. The objectification of the content may also include capturing metadata regarding the content.

Next, the platform tokenizes the content (step 1106). In one embodiment, one or more tokens are created to access and control the content. The tokens may represent fungible or non-fungible tokens. In one embodiment, a non-fungible token (NFT) is a unit of data stored on a digital ledger, called a blockchain, that certifies a digital asset to be unique, potentially of value, and therefore not interchangeable. The NFTs may be used to represent content, such as real-world items, art, collectibles, photos, videos, audio, and other types of digital files. Access to any copy of the original content may not be restricted to the buyer of the NFT. While copies of these content may be available for anyone to obtain, the NFTs may be tracked on blockchains to provide the owner with a proof of ownership that is separate from copyright.

In another embodiment, ownership of the content may be divided fractionally between multiple parties with each token including a share or percentage of the ownership of the item or content. As a result, the different owners/assignees may receive payments for monetization of the content through payments (e.g., cash, ACH, direct deposit, etc.) or additional tokens.

The token may include a secured pointer or link to the content stored in the digital ledger or secured database. The link may be utilized to share or manage the data.

Next, the platform sets user control over the content (step 1108). The user may specify settings, parameters, configurations, and other information that control how the content may be utilized, monetized, or otherwise managed. The user control information may include data from the applicable profile (e.g., user, company, gaming, social media, etc.). The information utilized to control the content may specify how the content/data is managed and distributed by an information data exchange. For example, the platform controls may specify how advertisers, marketers, artificial intelligence, research groups, or others may utilize the data. The platform and approved data collection process directly connects users with interested parties (e.g., corporations, marketers, advertisers, etc.) for increased control and monetization for both consumer and corporate data. The illustrative embodiments provide an improvement over the pay-per-click models in which there was little control over data collection, management, and utilization.

Figure 12:
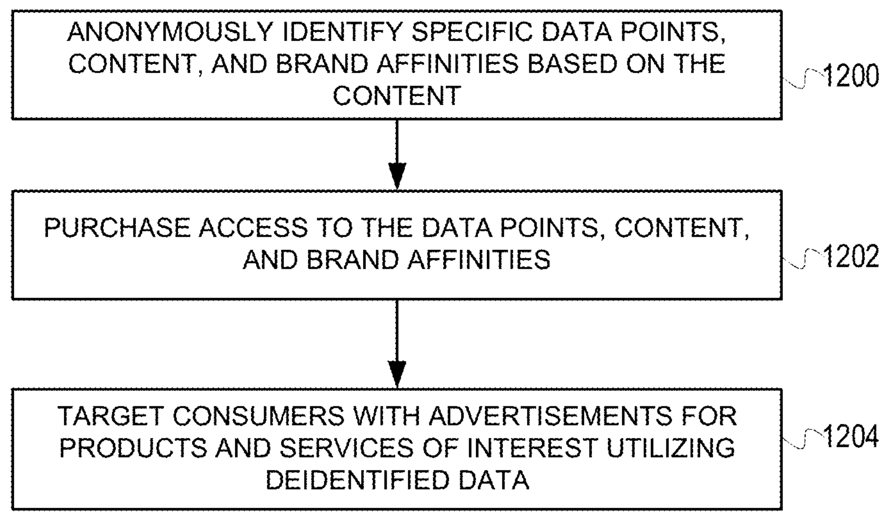
FIG. 12 is a flowchart of a process for targeted advertisements in accordance with an illustrative embodiment.

FIG. 12 is a flowchart of a process for targeted advertisements in accordance with an illustrative embodiment. The process of FIG. 12 may also be implemented by one or more advertising, marketing, or other companies that has authorized access to the applicable data or content. The process may begin by anonymously identifying specific data points, content, and brand affinities based on the content (step 1200). In one embodiment, the platform may utilize software installed on multiple devices to track the applicable data and content. The data and content may be tracked, aggregated, and/or saved without any identifying information. As a result, the data may be utilized in unique ways without compromising the privacy, safety, and security of the user (whether consumer, corporate, private, public, governmental, etc.). Various levels of deidentification may be utilized. For example, in some cases all of the personally identifying information, except for the applicable zip code and gender may be removed. In another example, the city and age of the user along with the applicable data points, content, and brand affinities may be tracked. Any different combinations of deidentified and specific data may be utilized based on the needs, interests, and wants of interested parties. Different types of artificial intelligence, machine learning, or advanced logic may be utilized.

Next, the platform purchases access to the data points, content, and brand affinities (step 1202). The platform may purchase access from the applicable content/data owner. As noted, the platform may provide a platform for tracking, aggregating, saving, selling/buying/monetizing the applicable data.

Next, the platform targets consumers with advertisements for products and services of interest utilizing deidentified data (step 1204). Any number or type of advertisements, marketing materials, or other data implementations may be implemented by the platform. The platform may utilize television, Internet, in-application, radio, search, print, or other advertisements to target the applicable consumers.

Figure 13:
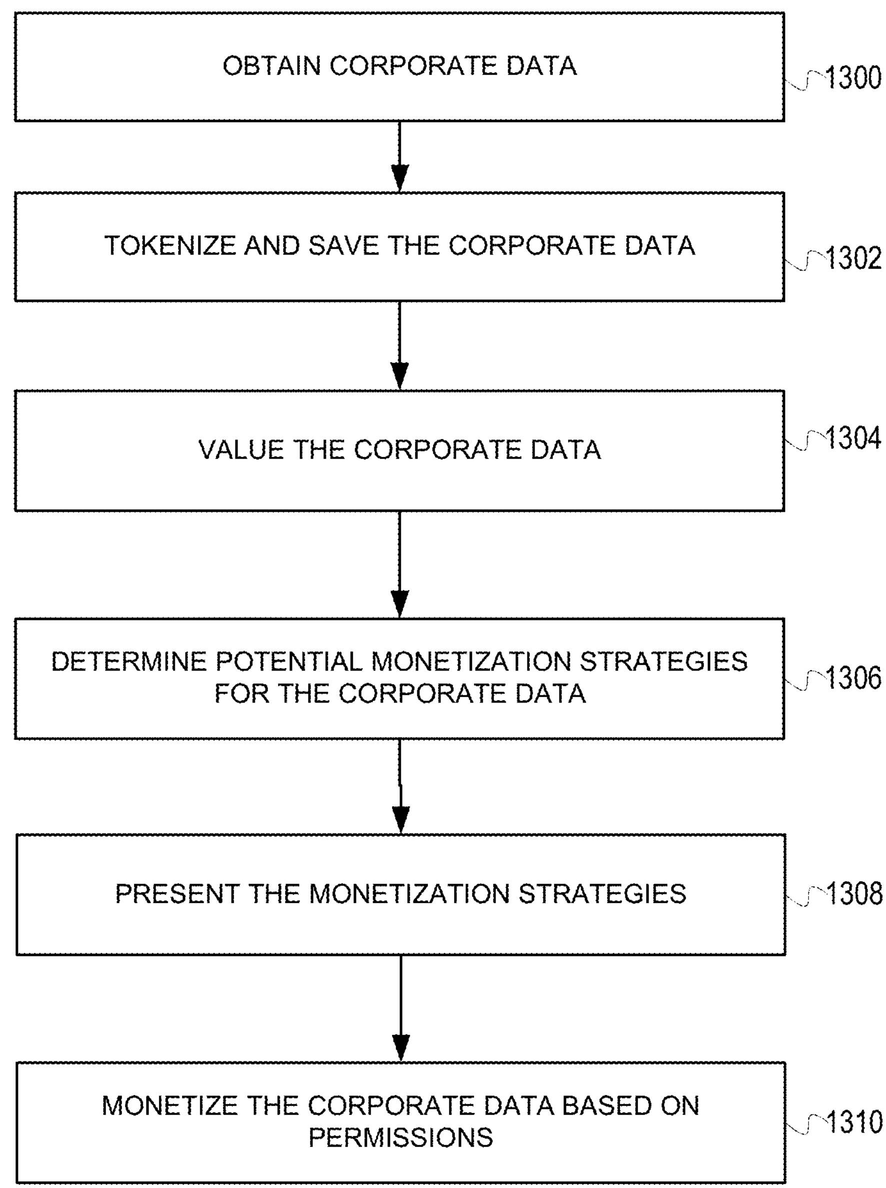
FIG. 13 is a flowchart of a process for utilizing corporate data in accordance with an illustrative embodiment.

FIG. 13 is a flowchart of a process for utilizing corporate data in accordance with an illustrative embodiment. All or portions of the process of FIG. 13 (and other processes) may be performed automatically without user interaction. The process of FIG. 13 may begin by obtaining corporate data (step 1300). The corporate data may be retrieved, tracked, or aggregated from any number of sources. Established data sources may be utilized for all or some of the data. New gather processes, servers, software, inputs, or databases may also be utilized to track additional data. The platform may provide corporations feedback regarding valuable or potentially valuable data that the corporations is, could be, or might track or record in the past, present, or future.

Next, the platform tokenizes and saves the corporate data (step 1302). The corporate data may be securely stored with one or more pointers, links, or access codes to the corporate data. The corporate data may be stored separately from the token or within the token.

Next, the platform values the corporate data (step 1304). The platform may value the corporate data based on the types of data, amounts of data, data update level (e.g., within 2 hours, days, weeks, months, years, etc.), users associated with the data, data completeness, and so forth. In one embodiment, one or more scores may be assigned based on the potential value of the data as described herein.

Next, the platform determines potential monetization strategies for the corporate data (step 1306). The monetization strategies may be determined based on the unique types and amounts of data. In one embodiment, the data may represent physical assets, such as real estate, property plant and equipment (PPE), capital, land, buildings, square footage, accounts, inventories, art, collectibles, receivables, or so forth. In another embodiment, the data may represent intangible assets, such as patents, trademarks, copyrights, leases, logos, brand names, brand positioning, computer programs, customer lists, franchise agreements, supply chain agreements, lottery positions, non-fungible assets, domain names, trade secrets, and other intangible assets. The monetization strategies may include selling or leasing the data. The data may also be accessed by advertisers, marketers, researchers, or others.

Next, the platform presents the monetization strategies (step 1308). The monetization strategies may be communicated to the user based on the determinations of step 1306. The platform may automatically recommend one or more monetization strategies based on algorithms, historical results, monetization trends, and so forth. The platform may present the monetization strategies audibly, visually, or through any number of mediums. Emails, in-application messages, text messages, audio/video communications, or other communications or messages may be utilized.

Next, the platform monetizes the corporate data based on permissions (step 1310). In one embodiment, the permissions may be saved within the user profile. In another embodiment, the platform may require an affirmative selection or acknowledgement regarding how the corporate data is going to be monetized before the process may begin (e.g., advertising, marketing, research, machine learning, etc.).

In another embodiment, the corporate data may represent data that is utilized by a user or individual to earn an income. For example, the corporate data may represent the social media content, profile, and presence of an influencer. The corporate data may represent information from websites (e.g., gaming, communication, fan, retail, etc.), social media profiles, computer programs, mobile applications, and so forth.

Figure 14:
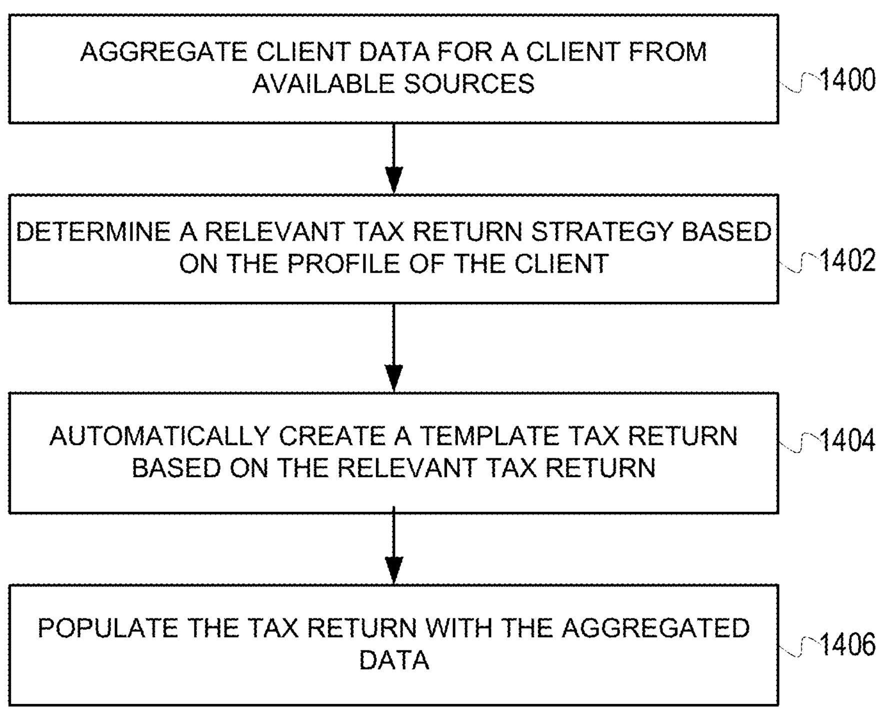
FIG. 14 is a flowchart of a process for generating a tax return in accordance with an illustrative embodiment.

FIG. 14 is a flowchart of a process for generating a tax return in accordance with an illustrative embodiment. The illustrative embodiment may be utilized to provide an enhanced tax collection and filing process. The process may be utilized for individuals in the lowest tax bracket, to high-net-worth employees and entities. The tax and business-related information may also be utilized as described in FIG. 13, other Figures, processes, and methods herein described. The various steps may tokenize data during the process for easy utilization, securitization, and/or potential monetization.

The process may begin by aggregating client data for a client from available sources (step 1400). Applicable accounting and tax data may be acquired from any number of sources, such as accountants, CPAs, bookkeeping/accounting software (e.g., TurboTax, H&R Block, FreshBooks, Sage Business Cloud Accounting, Account Edge Pro, Wave, Xero, and so forth. The platform may also evaluate past and present account information, account balances, transactions, corporate purchases/services, inventory, purchase orders, and other applicable information. The client may approve access to sensitive data to reduce or eliminate the need for third party data collection services thereby reducing the potential for identity theft, fraud, loss of savings, or theft of intellectual property. Not all of the retrieved or aggregated data is relevant. The platform may utilize various parameters, criteria, artificial intelligence, machine learning, or so forth. The platform may also remove or filter sensitive data to protect the privacy, intellectual property, trade secrets, know-how, and confidential works of the client (as well as their clients, patients, etc.). In one embodiment, a profile may be generated for the client. In one embodiment, the data may be deidentified so that it may be more broadly shared and utilized without compromising the safety, security, advantage, and privacy of the client.

Next, the platform determines a relevant tax return strategy based on the profile of the client (step 1402). The platform may compare the information, data, and profile for the client to a number of other entities or organizations. The platform may identify the most similar entities with successful tax returns and filing strategies. By identifying similar companies, the client may be able to utilize a similar path, strategy, structure, documentation, and efforts to be successful in the marketplace and with applicable government regulation and laws. For example, a selection of the most similar or relevant companies may be determined based on success metrics (e.g., share price, profitability, sales revenue, net profit margin, gross margin, customer loyalty and retention, net promoter score, etc.), known audits, reputation, professional rankings, and so forth.

Next, the platform automatically creates a template tax return based on the relevant tax return and the data (step 1404). The platform may use the most relevant tax return strategies and filings from selected companies as a template to create a tax return template for the client. Different strategies and forms may be combined from a single company or multiple companies to generate the best potential template tax return for the client. Different companies may have relevant corporate details that may best match up with the client, and as a result, their different tax filing strategies may be utilized.

Next, the platform populates the tax return with the aggregated data (step 1406). The already aggregated data may be utilized to populate the tax return for filing. The tax return may include federal and state filings. The tax return may also include any number of yearly payments, statements, declarations, or other filings that may be required throughout the year. The same methodology may be utilized for any number of managements, business, technology, or other processes that may be duplicated.

In one embodiment, the automatically completed tax return may be communicated for review by the user(s), an accountant, and/or tax return professional/service. For example, approval may be required before the one or more tax returns may be filed. An artificial intelligence or machine learning review may be performed by the data platform before filing the tax return. Any issues or problems may be communicated as an alert at any time during the process of FIG. 14. The issues may require corrections from one or more users. The platform may also electronically file the one or more tax returns (e.g., Federal return and one or more State returns) to complete the process. Likewise, the platform may be utilized to perform audits or comparisons of other tax returns to provide feedback, generate alerts, suggests changes, or provide input regarding past, present, or future tax returns, forms, strategies, and so forth.

Figure 15:
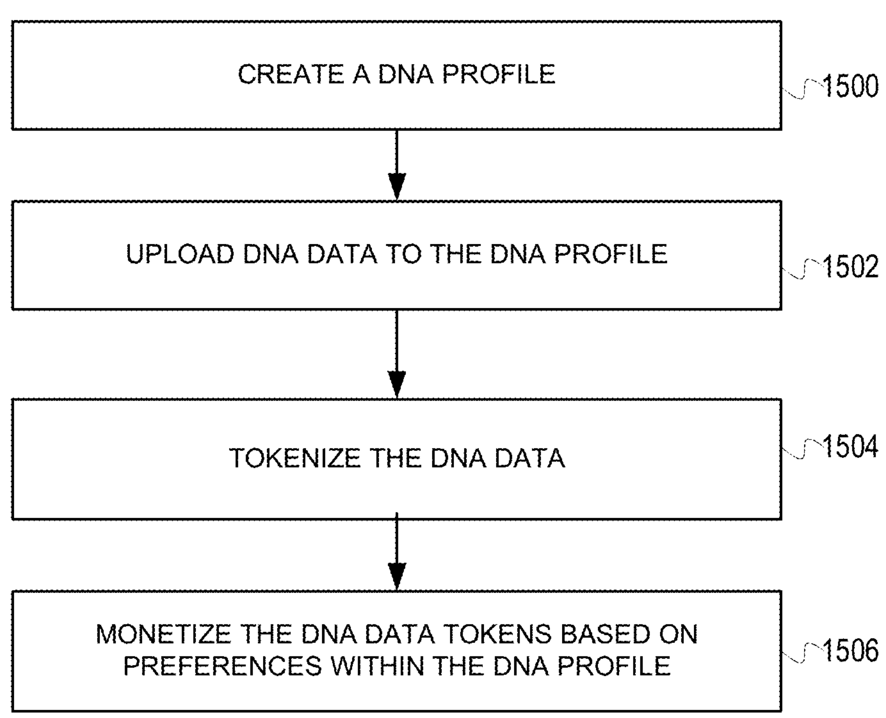
FIG. 15 is a flowchart of a process for monetizing DNA data in accordance with an illustrative embodiment.

FIG. 15 is a flowchart of a process for monetizing DNA data in accordance with an illustrative embodiment. The process may begin by creating a DNA profile (step 1500). The DNA profile may also be referred to as a user profile. The user profile may specify name, age, sex, ethnicity, birthday, birth location, parents, blood type, ancestry records, health history, home address, and any other applicable information. The user profile may include required and optional data that may be utilized to provide additional information to the user. For example, the data may also include medical history of diseases, conditions, ailments, issues, or other conditions. The DNA profile may specify the user's history of cancer, heart disease, autoimmune conditions, Next, the platform uploads DNA data to the DNA profile (step 1502). The DNA data may be acquired through any number of publicly or privately available DNA tests (e.g., AncestryDNA®, 23andMe®, MyHeritage®, FamilyTreeDNA®, etc.) or sequencing processes. The DNA data may include the entire genome sequence of the user or only portions of the genomic sequence. The DNA data may be uploaded based on explicit permissions from the user. Data may be associated between different platforms, servers, or databases. For example, the DNA profile may be updated based on the DNA data. The platform may also be configured to perform sequencing to gather the DNA data from a user specimen (e.g., saliva, blood, etc.).

Next, the platform tokenizes the DNA data (step 1504). The DNA data may be tokenized as herein described. The DNA data may be tokenized with or without user identifying information. For example, for various applications, such as medical research, the identifying data may be removed from the DNA data to protect the privacy of the user. The user may specify in the DNA profile how the tokenized DNA data may be utilized. For example, a user may specify that their DNA data may be utilized for medical research if their private information is disassociated from the DNA data. The user may also specify that their DNA data may be utilized to propose medications, treatments, remedies, or other wellness benefits. The DNA data may only be associated with their private information based on a request that is verified by the user and agreed to terms (e.g., privacy, payment, etc.).

Next, the platform monetizes the DNA data tokens based on preferences within the DNA profile (step 1506). In one embodiment, the DNA data tokens may be processed, sold, licensed, leased, rented, shared, analyzed, purchased, or otherwise managed by the data platform or otherwise made available to authorized individuals, groups, entities, or so forth. The DNA data tokens may be permanently or temporarily transferred. In some embodiments, the tokens may be utilized within the platform (e.g., a controlled ecosystem) to ensure that privacy rights are not violated. In one embodiment, the user associated with the DNA data is compensated in hard currency or cryptocurrency every time that their DNA data is utilized. As a result, the user benefits from sharing their DNA data rather than companies that may acquire the data illegally or utilizing questionable methods.

In one embodiment, the deidentified data may be utilized to determine DNA profiles and data that may be useful to any number of parties or entities. As a result, the user may be anonymously approached with any number of offers for licensing or sharing all or portions of their DNA data.

The DNA data may be utilized by medical professionals, pharmaceutical companies, citizen scientists, and others for the benefit of the user. Control of how and when the tokenized data is utilized is maintained by the user unless assigned, sold, or transferred at the user's approval.

Figure 16:
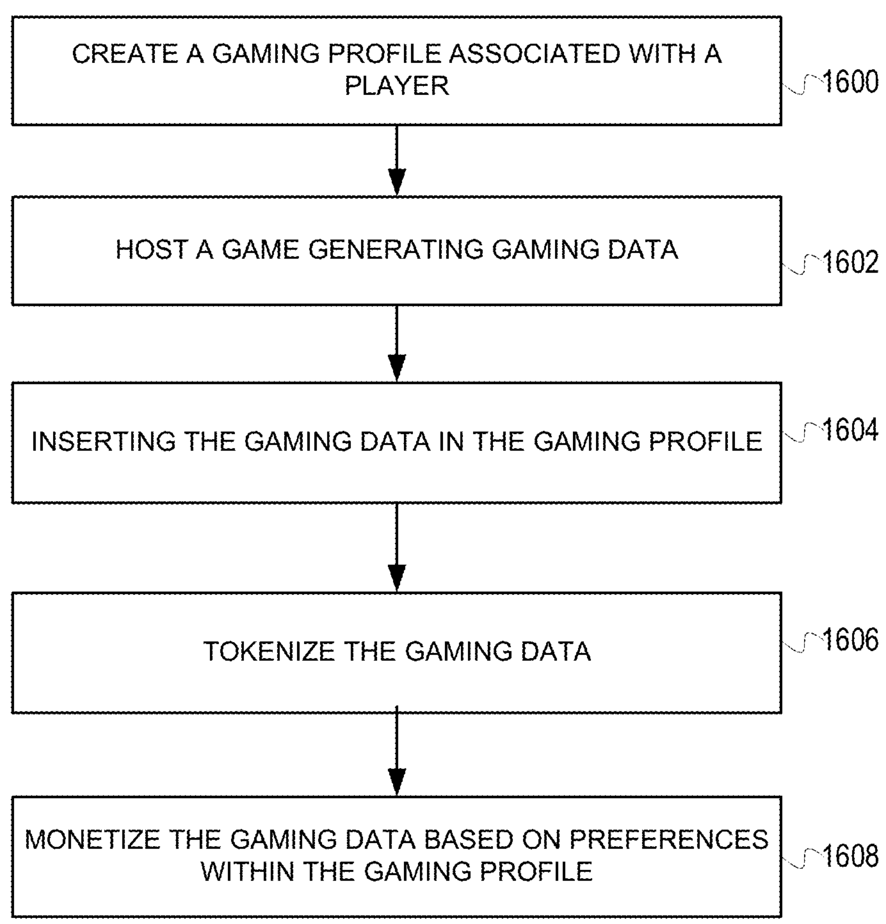
FIG. 16 is a flowchart of a process for monetizing gaming data in accordance with an illustrative embodiment.

FIG. 16 is a flowchart of a process for monetizing gaming data in accordance with an illustrative embodiment. The process of FIG. 16 may be utilized by players of various skill levels (e.g., novices, amateurs, experts, professionals, influencers, etc.) in-game trophies, badges, accomplishments, and purposes for playing. The process may begin by creating a gaming profile (step 1600). The gaming profile may include name, age, username, address, billing information, avatar, friends, privacy/sharing settings, interests, and so forth. The gaming profile may be similar to gaming profiles already utilized by players across systems, platforms, and networks. The gaming profile may also be automatically generated based on information applicable to a console, computer, or other applicable profile or data.

Next, the platform hosts a game generating gaming data (step 1602). The game may be hosted by the platform itself or by third-party platform or system that communicates with the platform. The platform may obtain or capture the gaming data utilizing any number of processes, such as game play, questions/surveys, purchases, or so forth. The gaming data may represent trophies, rewards, certificates, achievements, levels, task achievements, completion percentage, time periods, game events, checkpoints, or other applicable information that indicates status, gameplay, or achievements. The gaming data may be gathered through a player/player profile progressing through a video game and completing game elements. The game may represent any number of different games (e.g., role-playing, strategy/intellectual, action, action-adventure, first-person shooter, simulation, sports, massive multiplayer online games (MMO), etc.). Gaming data may also be captured during the game, uploaded, or transferred as collected or singular gaming data.

Next, the platform inserts the gaming data in the gaming profile (step 1604). The gaming data may be cumulatively added to the gaming profile associated with the user periodically (e.g., hourly, daily, weekly, etc.), based on game play, based on achievements/progress points, or so forth. The updates to the gaming profile may be performed automatically or in response to player inputs, selections, and/or approval. The updates may be performed in real-time, periodically, or based on approval from a user.

Next, the platform tokenizes the gaming data (step 1606). The gaming data may be encapsulated, integrated, attached, linked, or otherwise associated with one or more tokens. As previously noted, the tokens may represent nonfungible tokens, gaming tokens, crypto currency tokens, or so forth. Agreements with the player may specify how the tokens are utilized and managed. In one embodiment, the player controls and manages how the tokens may be utilized to ensure the players privacy, digital rights, personal contact, and so forth is protected. In one embodiment, the gaming data may include video, audio, images, or other content associated with the player's gameplay that may be monetized. For example, the players greatest moments as captured may be included as tokens that may be licensed, distributed, auctioned, sold, or otherwise monetized.

Next, the platform monetizes the gaming data based on preferences within the gaming profile (step 1608). As noted, the gaming data may be monetized utilizing any number of nonpermanent, semipermanent, or permanent transactions (e.g., licenses, royalties, sales, exchanges, etc.). The player may also implement any number of trades or transactions utilizing the tokenized gaming data. The platform may enable players to monetize their skills, efforts, games, highlights, or so forth. The platform may also enable various individuals or groups to sponsor a player through the purchase or license of tokens tied a specific gamer profile. The gaming data is monetized based on the preferences of the player. The player may have individual preferences, requirements (e.g., legal, moral, etc.), parameters, rules, or settings that govern how their gaming data may be monetized. The preferences are honored to ensure that the players are satisfied with the results of the monetization and so that additional players are comfortable utilizing the tokens and process of FIG. 16.

As previously noted, the players may be incentivized and/or compensated with rewards, coins, tokens, fiat currency, corporate branded tokens, physical steam points, in-game currency or credits, real-world prizes, cash, or any form of blockchain based tokens. The process may also be utilized by game developers or managers to make determinations based on player input (e.g., influencers, experts, fans, etc.). Tradeable in game rewards, skins, or other tradeable virtual items may be tokenized as an NFT and sold to other users through verifiable and traceable transactions via the blockchain.

Any number of processes may also be utilized to monetize or create valuable gaming data. For example, in-game challenges, surveys, advertisements, or other data gathering and monetization techniques and methodologies may be utilized. Players may also be rewarded and incentivized for top players/performances, level/achievement completion, finding a special item, fastest players to complete a game, and so forth. Developers may be able to form groups of subject matter experts and game experts that may facilitate existing and future game development. Players, third-parties, brands, and others may be compensated for creation of content, advertisements, video tips, fan content, and so forth. Retiring games or gainers shifting gaming platforms may monetize their data through the sale of their profile, steam tokens, cryptocurrency, or so forth that may be converted from digital bounties, rewards, trophies, or tokens.

Game developers, advertisers, and others may utilize the gaming profiles and data that are legally acquired to provide targeted marketing, advertising, offers, updates, opportunities, and so forth. The user/gamer controls monetization and utilization of their own data and profiles as tokenized on the blockchain as described herein.

Figure 17:
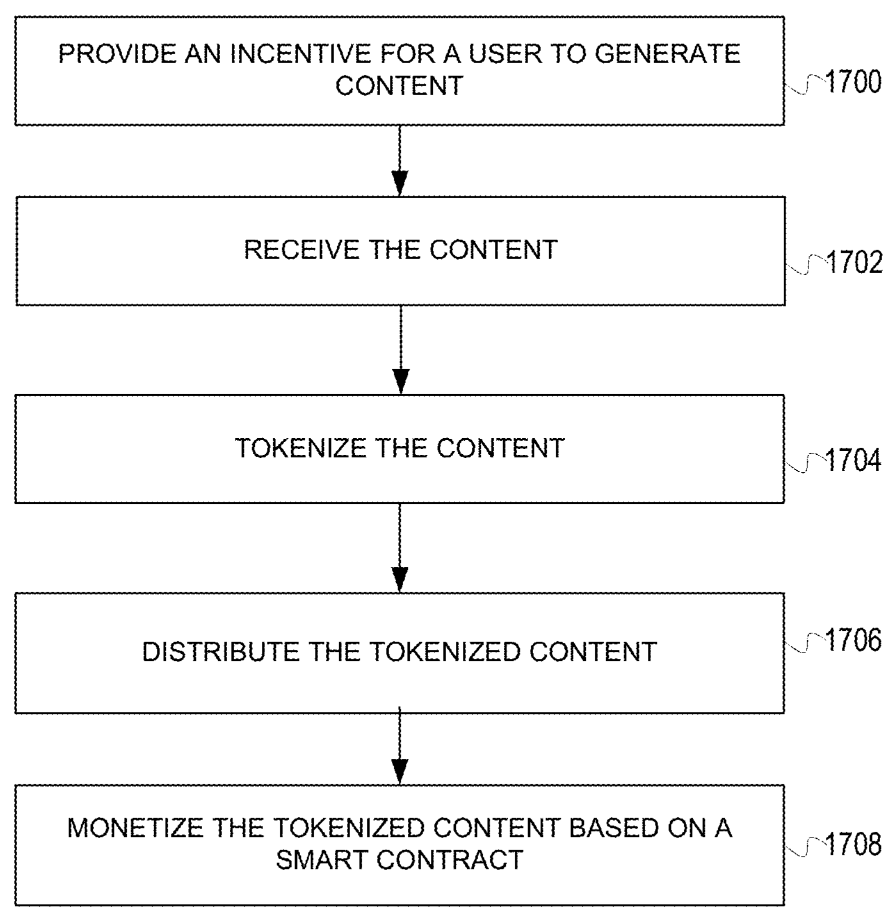
FIG. 17 is a flowchart of a process for distributing content in accordance with an illustrative embodiment.

FIG. 17 is a flowchart of a process for distributing content in accordance with an illustrative embodiment. The content of FIG. 17 may correspond to content or profiles, or influencers associated with social media content, gaming content, artistic content, sporting/recreational content, intellectual content (e.g., code, writing, whitepapers, quotes, essays, inventors, scientists etc.), movies, videos/skits, comics, documentaries, and so forth. Data related to book collections, music collections, record collections, art collections, virtual collections, teaching lesson plans, music lessons, church sermons, prayers, quotes, and so forth may be objectified and tokenized for the purpose of controlled sharing, donation, monetization, proof of ownership, or insurance documentation process. The illustrative embodiments allow corporate and personal data to be tokenized and monetized.

The process may begin by providing an incentive for a user to generate content (step 1700). Users may be incentivized utilizing any number of monetary (e.g., currency, crypto currency, etc.) or non-monetary incentives (e.g., status, coupons, discounts, etc.). The incentives or solicitations may be proposed utilizing one or more smart contracts that may be reviewed by the player/user for the purposes of transparency, clarity, and openness. In one embodiment, opinions as content may be very valuable. As a result, users that participate may be compensated (e.g., money, cryptocurrency, coupons, discounts, rebates, prize entries, etc.). For example, governments, cities, companies, organizations, churches, non-profits, advertisers, outreach providers, brands, or other data solicitors may obtain real-time information and data that those parties may consider important and relevant. The content may also relate to a user or group's location or intended destination. The location information may be shared in order to receive local marketing and advertising content for business trips, vacations, companies exploring relocation, and so forth.

Next, the platform receives the content (step 1702). The content may be received through an upload, in-application capture, screen captures, survey, user selections, import/export, messages (e.g., email, text, in-application message, etc.), and other processes. The content may represent an image, video, galleries, security camera content, metadata (e.g., time logs, data collected, etc.), audio, text, artwork, digital collectible, domain name, ticket, or other file or content. Video, audio, and other content may be captured from any number of sources (e.g., news events, sports video, paparazzi, amateur videographers, investigation, individuals, etc.). The content may be valued as previously described. Monetization strategies may be determined for the real-time and potential or unrealized value of content. The monetization strategies may be presented to the user for review and approval, or the monetization strategies may be automatically implemented without interaction, based on user preferences, or based on user approval.

Next, the platform tokenizes the content (step 1704). The content may be identified utilizing blockchain as unique and novel and assign a data value calculation. Any number of existing blockchain tokens may be utilized as well as proprietary tokens. For example, themed or branded tokens may allow any company or organization or non-profit to create their own cryptocurrency or blockchain tokens. For example, a brand or chain may initiate a themed or branded promotion using a corporate branded token data collection campaign that may be used to connect to consumers through data collection and consumer shared data access in exchange for tradeable or monetizable branded tokens. The tokens may be gamified in a way that encourages users to collect each branded token that acts as a puzzle piece to create a collectable puzzle image created through the collection of each unique token puzzle piece. The tokens may have an associated shape, number, image, number, or other associated information for completing the puzzle. One or more websites or applications may be utilized to collect, place, assemble, or otherwise utilize the token alone or with other individuals, groups, or entities. In one embodiment, the type of tokenization process may be selected based on the best blockchain technology or token for the type of content. For example, an asset such as artwork may benefit from token tracking methodologies that are different from that of personal asset, such as the image of a college or pro sports athlete that allows the athlete to manage their persona as a marketable asset.

In one embodiment, data related to vehicles, such as ownership, title, gas mileage, service record, emissions, tire readout, recalls, and so forth may be tokenized for alerts and monetization via the platform. This information may be utilized by owners, dealers, or others to validate relevant information during a transaction for or regarding the vehicle.

Next, the platform distributes the tokenized content (step 1706). In one example, the tokenized content may be distributed or communicated utilizing tokens. The tokens may include the content. In another example, the tokenized content may include a link to the content. The tokenized content may be purchased, leased, or otherwise temporarily access as noted. As previously noted, the content may be modified to prevent identifying information from being included. As a result, the value of the content and tokens may be maintained while removing information that may personally identify and individual or company.

Next, the platform monetizes the tokenized data based on a smart contract (step 1708). The smart contract may govern how the content associated with the tokens, cryptocurrency, platform/exchange, is utilized. The smart contract ensures that all portions of the agreement are fairly implemented.

Figure 18:
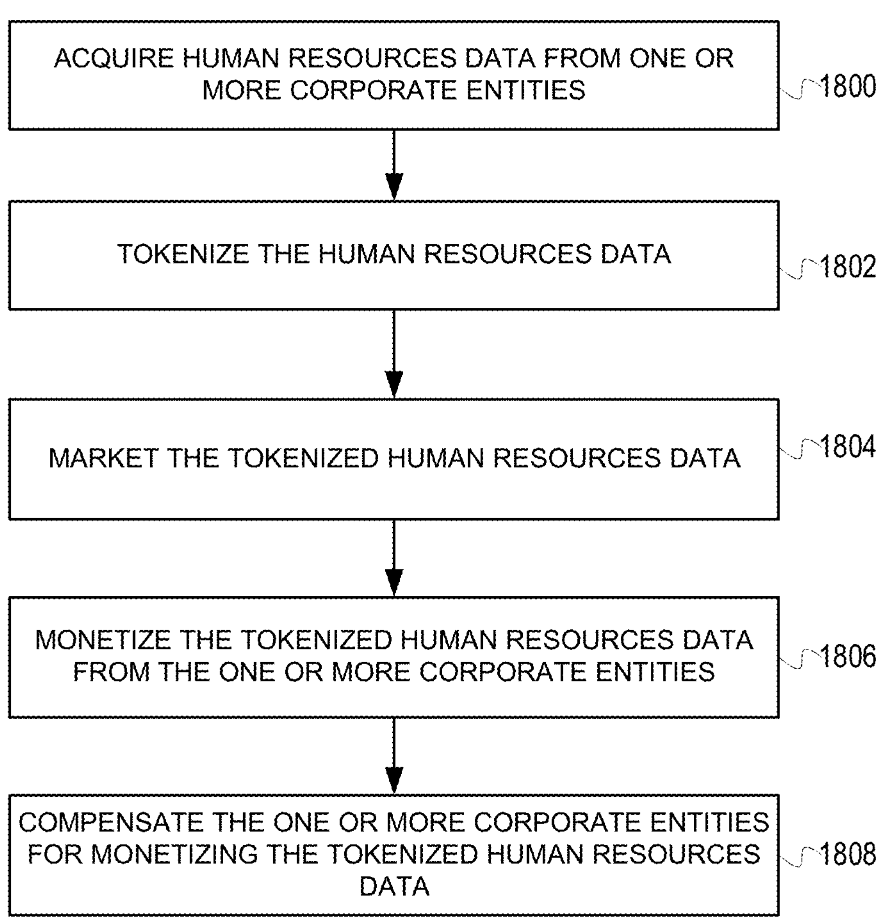
FIG. 18 is a flowchart of a process for monetizing human resource data in accordance with an illustrative embodiment.

FIG. 18 is a flowchart of a process for monetizing human resource data in accordance with an illustrative embodiment. In one embodiment, latent corporate, human resources (HR), and accounting data may be valued and monetized. The human resources data may include demographic data, recruiting data, performance management and efficiency data, talent development data, succession planning data, compensation and bonus data, engagement and retention data, time tracking (absentee) data, medical leave data, benefits data, and other similar information. The process may begin by acquiring human resources data from one or more corporate entities (step 1800). The human resource data may represent all or portions of the data associated with employees of a company, entity, or organization. The human resources data may be captured from any number of systems, platforms, software, operating systems, corporate service providers, or so forth (e.g., SAP, SuccessFactors, Sage Business Cloud People, Workday Human Capital Management, BambooHR, Fresh Team, Gusto, ADP, etc.). The human resources data may be captured as part of the onboarding process for the applicable employees. For example, the human resource data may include information captured as HR files, resumes, personnel files, accounting data, business plans, employee tax forms, and so forth for similar companies. Employees may include executives, managers, salaried employees, hourly employees, independent contractors, and others that perform work on behalf of the company, entity, or organization. In one embodiment, the identifying information may be removed from the human resource data to protect the privacy and security of individuals associated with the human resource data.

Next, the platform tokenizes the human resources data (step 1802). The human resources data may be tokenized to include or link to the human resources data. Secure access to the human resource data may be provided through the tokens, links, or identifiers. The human resources data may be deidentified to prevent unwanted identification and to minimize risks (e.g., identity theft, corporate data theft, etc.).

Next, the platform markets the tokenized human resources data (step 1804). The human resource data may be valuable based on the associated organization, number of employees, perspective, and other information that may be valuable to research companies, advertisers, marketing companies, hiring companies, or so forth. The tokens may be purchased by similar companies or others looking for new employment data streams, application data, income data, housing data, franchise data, competitive analysis, strength, weakness, opportunity, and threat (SWOT) analysis, market positioning, offer information, and other indicators, data, details, or information.

Next, the platform monetizes the tokenized human resources data (step 1806). The tokenized human resource data may be monetized internally or externally. In one example, the employment agreement of the employees may specify that human resource data may be captured and monetized the employment agreement, or a smart contract may also stipulate whether the employee receives any compensation for utilization of the tokenized human resources data. The platform or associated company may market, advertise, or display the type of human resources data that may be available to interested parties.

Next, the platform compensates the one or more corporate entities for monetizing the tokenized human resources data (step 1808). The tokens or tokenized content may be purchased by companies, consulting groups, or others looking to enhance their recruitment, development, training, and performance efforts as well as develop appropriate and competitive compensation, benefits, culture, and other company characteristics. In one embodiment, human resources data is acquired from the aforementioned entities regarding sexual harassment, employment termination, and age, gender, and race discrimination/equality efforts that may be tokenized. These tokens may be purchased by other companies to develop or refine their diversity, equality, and inclusion programs, standards, and efforts. Tokenized data assets may be monetized at any time even during a bankruptcy to enhance the value of the data.

Figure 19:
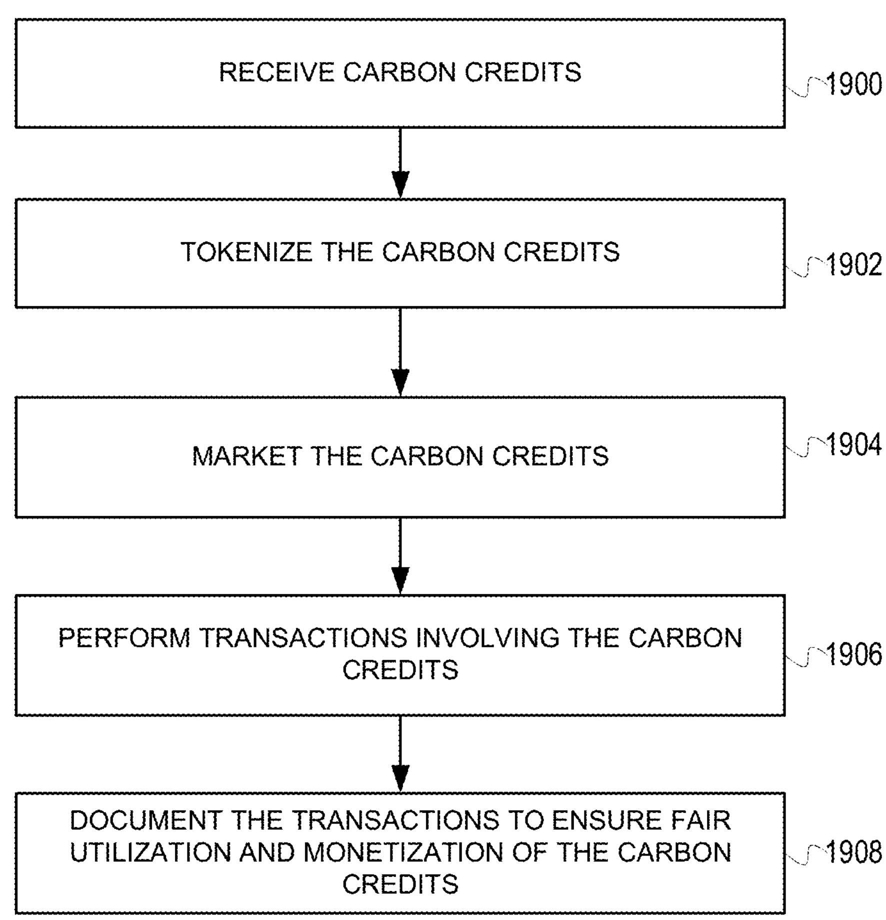
FIG. 19 is a flowchart of a process for processing carbon credits in accordance with an illustrative embodiment.

FIG. 19 is a flowchart of a process for processing carbon credits in accordance with an illustrative embodiment. In one embodiment, the process of FIG. 19 may be implemented by a trading platform (e.g., data platform). Carbon credits are used a system and method to reduce the emission of greenhouse gases to limit global climate change. In one embodiment, a carbon credit is a permit or allotment that allows the company that holds the carbon credit to emit a certain amount of carbon dioxide or other greenhouse gases (GHGs). In many cases, companies that do not need all of their credits may sell the credits to other companies that may need additional credits. Typically, a carbon credit is equal to one ton of carbon dioxide. Any number of existing cryptocurrency coins or tokens may be utilized. In another example, a new cryptocurrency coin may be utilized.

The carbon credits may be utilized by owners, purchasers, traders, and other parties that may represent large companies, governments, farmers, landowners, airlines, freight haulers, at-risk nations (e.g., island nations), and others. The carbon credits are associated with tokens to validate authenticity, verification, need, conservation/carbon offset efforts, document the process, and perform effective management. The carbon credits may be associated with coins, tokens, or transactions utilizing a smart contract. The carbon credits may also be associated with specific locations (e.g., GPS coordinates, latitude/longitude, legal title for properties, acreage, etc.) for the generation of carbon credits, protection of the land, advanced utilization, or other purposes. For example, the process of FIG. 19 may be utilized to ensure that specific tracts of land, acreage, square footage, associated with a carbon credit are utilized to remove more carbon from the air than was produced by the purchasing party.

The illustrative embodiments also facilitate the connection of companies and organizations who have an excess of carbon credits with companies who have exceeded their carbon production/utilization limits by allowing the companies to purchase additional credits to maintain compliance and good standing. For example, Bitcoin or cryptocurrency miners, server farms, or other groups/individuals may purchase carbon credits to mitigate their carbon footprint for automobiles, aircraft, computers/servers, factories, to create environmentally neutral, green, or carbon-reduced footprints. The illustrative embodiments may be run as an industry group, cooperative, collaborative group, or private entity in order to promote carbon credits outside of the political influence and uncertainty of governments, politics, and politicians.

The process may begin by receiving carbon credits (step 1900). The carbon credits are allocated to applicable companies. The allotment of carbon credits may vary based on the type of company, output, number of employees, critical nature of the company (e.g., healthcare, energy production, manufacturing, etc.). In one embodiment, the carbon credits may be ascribed an identifier (e.g., numerical value, hash, verification code, etc.) as each coin is minted/generated providing a novel electronic method to draw on the carbon credits and accurately track the coins and associated credits. In another embodiment, different users, parties, or companies may receive carbon credits based on carbon sequestration performed. Carbon may be sequestered by performed utilizing any number of systems, methods, or devices (e.g., geological sequestration, biological sequestration, direct air capture, etc.). For example, greenhouse gases may be captured from industrial facilities, power plants, dairies, or other facilities and then injected underground for captured, enhanced oil recovery, or other processes. Carbon credits may also be generated by protection or use/non-use of land (e.g., not deforesting the Amazon rain forest, planting carbon capturing crops/trees/plants, etc.) and other proactive or passive steps. Specific locations, properties, acreage, forests, parcels, or regions may be tied with one or more of the carbon credits. The process may allow companies or farmers with an excess of carbon credits to tokenize carbon credits for trade or sale on the tokenized asset marketplace.

Next, the platform tokenizes the carbon credits (step 1902). In one embodiment, the carbon credits may be associated with coins or tokens. During step 1902, tokens may be generated/minted to include the carbon credits and associated information. The coins require associated carbon credits to be associated with them. As a result, all coins are backed by an associated amount of carbon credits (e.g., 1 MT, ton, etc.). In one embodiment, a numerical value may be assigned to each block of credits. As a result, the platform may draw down and account for all credits, their sale, and utilization.

Next, the platform markets the carbon credits (step 1904). Entities with surplus carbon credits may market the associated coins or tokens utilizing the platform. The needs of different entities allow for the carbon credits to be exchanged with the money involved utilized to support environmental efforts and offset the effects of emitting carbon dioxide or other greenhouse gases, undesirable materials, or potential pollutants.

Next, the platform performs transactions involving the carbon credits (step 1906). In one embodiment, each time a carbon credit is utilized, the associated coin may be converted or tokenized as a non-fungible token or alternative type of coin (e.g., designated for utilized carbon credits). The record of the utilization includes all applicable information including creation date, carbon credit, transactions entities, transactions dates, utilization/retirement date, emission data, data for the company/entity utilizing the carbon credit, offset information, and so forth. Transactions may also involve partial tokens to allow smaller companies to participate in the process. As a result, partial carbon credits associated with partial coins may be tracked, managed, transacted, and utilized.

Next, the platform documents the transactions to ensure fair utilization and monetization of the carbon credits (step 1908). The transactions may be recorded in a digital ledger (e.g., multiple digital ledgers) for open and transparent review. For example, the ledger may track each instance the coin associated with the carbon credit is traded on the secondary market. All retired carbon credits associated with a token or coin may be indexed for reference. Used carbon credits may be drawn down from an overall, national, regional, or local account, count and/or tracking system. The blockchain system implemented by the platform provides an immutable ledger for each unique record of carbon retirement. For example, retired credits may be indexed and tokenized as an NFT. The ledger may track each instance the applicable coins are traded on the primary or secondary markets as the assets are held, traded, or monetized.

In one example, certified carbon credits may be valued at $8 per metric ton (MT) with pre-certified credits valued at $4 per MT. All tokens or cryptocurrency coins may be backed by certified or pre-certified credits. Each coin may be backed either by 12 MT of certified credits or 24 MT of pre-certified credits. Credits that are bought pre-certified typically have a lower initial cost providing a cost benefit when purchased as pre-credits. There may be a combination of certified and pre-certified credits backing each coin at a ratio of 2 to 1 (pre-certified to certified). The credits collateralizing each coin may be uniquely identified by an authorized group or party, such as GEC Communities, Inc. for the contract, concession, and time period of creation.

Each coin holder may have the ability to sell the underlying credits from the asset holding vehicle (e.g., coin, token, etc.) at a fixed costs per metric ton. The sales may be performed by authorized parties. The trading platform may impose limitations regarding the number of times that the coins may be traded per year or other time period. In one embodiment, if the credits are sold for a price greater than a predetermined amount or threshold (e.g., $6.40 net cost), the additional proceeds will belong to the coin holders. When credits are solid from the coin reserve, an entity, group, or conservator (e.g., GECC) may be paid 80% of the price ($8.00×0.80=$6.40 and the balance of the fund will stay in the coin holding vehicle for distribution. The managing entity may immediately replenish the coin with the number of credits that have been sold to ensure that the coin(s) are always properly collateralized.

In one embodiment, the difference per ton between the sales price and the threshold (e.g., $1.60 per metric ton—$8-$6.40) may be distributed to the coin holders with any administrative costs/fees subtracted from the total each time the sale occurs. For example, the funds may be utilized to cover overhead for managing the platform/exchange (e.g., approximately $0.24 per MT of the $1.60) with net proceeds (e.g., $1.36 per MT) distributed to the coin holders, such as the coin holder that sells the coins. Once the seller has been compensated for all credits that are collateralizing the coin(s) the balance may be distributed on a Pari Passu basis (i.e., equally without preference) across the coin holder base. The coin holder that sells the underlying carbon credits is paid first in the payment distribution for the sale. If a coin holder sells a volume of carbon credits greater than his underlying collateral the holder is effectively selling the credits backing other coins. Each individual coin holder has the right to "reserve" the carbon credits backing their coin(s) which are effectively removed from the total pool of carbon credits available to be sold or utilized. The act of reserving the credits may eliminate the possible duplicate sale of the credits from the pool. For example, a managing party or entity (e.g., GECC) may ensure that the carbon credits are properly allocated, associated with coins/tokens, and added/removed from the applicable pool. In one embodiment, when credits are sold, a token or coin may be generated permanently identifying those credits that have been retired and may clearly identify the related carbon signature that the credits are offsetting. All records associated with the carbon credit cryptocurrency management will be securely recorded and stored in the platform in conjunction with the books and records of the tracking organizations to ensure transparency, environmental protection, and best practices.

Figure 20:
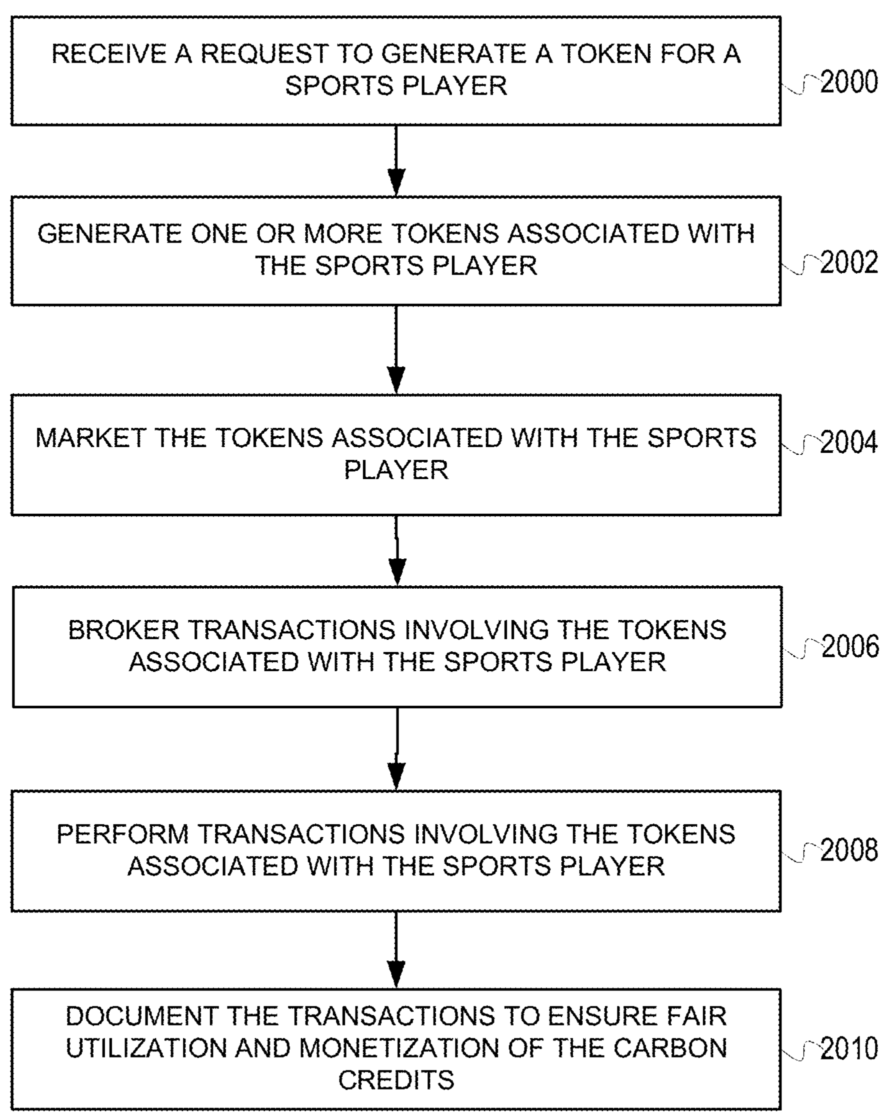
FIG. 20 is a flowchart of a process for monetizing tokens associated with a player in accordance with an illustrative embodiment.

FIG. 20 is a flowchart of a process for monetizing tokens associated with a sports player in accordance with an illustrative embodiment. The process may begin by receiving a request to generate a token for a sports player (step 2000). In one embodiment, the sports player may represent a developing, recreational, amateur, semi-professional, college, professional, expert, or other sports athlete regardless of skill level. The player(s) may also represent non-sport related individuals, such as chess players, influencers, scientists, intellectuals, politicians, specialists (e.g., doctors, lawyers, crane operators, engineers, etc.), or any number of individuals, organizations, or entities. The sports players may have rules, laws, limitations, or standards regarding the legal, organizational, standard-based, or other requirements that each player is required to adhere to comply with. For example, amateur, semi-professional, or college athletes may have limitations regarding the compensation, sponsorship, or other payments that they may receive to maintain their status (e.g., amateur, non-professional, collegiate, etc.), and comply with applicable laws, rules, and standards. The token may represent the name, image, profile, appearance, and likeness of the player. In other embodiments, the token may also represent a moment (e.g., score, play, response, historical moment, sentimental moment, etc.), event, image, likeness, achievement, video, meme, file, physical items, or other content associated with the player. Teams may also tokenize their logo, stadium, roster, pictures, or other content for recreational, entertainment, amateur, college, semi-professional, professional, or other teams.

Next, the platform generates one or more tokens associated with the sports player (step 2002). In one embodiment, the one or more tokens may represent the applicable content in any of the aforementioned formats. For example, the token may be associated with a player profile. The token may include the applicable content. For example, the content may be embedded, included, or integrated in the token. In another example, the token may include a reference or link to the content. The token may also include a smart contract. The smart contract may be utilized for sponsoring the player, licensing the content, paying royalties, purchasing the token (and/or associated content), and otherwise performing transactions for the content. In one embodiment, the token may be associated with physical or third-party ownership (e.g., items held in escrow, museums, etc.) or game or practice used items, such as signed balls, uniforms, shoes/footwear, skates, bases, rims, nets, tees, pads, pucks, helmets, hats, car parts, and so forth. The one or more tokens may represent nonfungible tokens or fungible tokens. For example, amateur, college, and professional sports players or personalities (e.g., referees, announcers, ball girls/boys, umpires, etc.) may create profiles. Different players may tokenize their persona to make it available to marketers, advertisers, companies, or others. For example, different offers, spokesperson roles, sponsorships, licenses, royalties, deals, or transactions may be performed virtually, electronically, and/or in person.

Next, the platform markets the tokens associated with the sports player (step 2004). The platform may manage the tokens associated with a number of players. The platform may communicate the available tokens utilizing any number of communications methods including mobile applications, websites, programs, email, text message, advertising (e.g., television, radio, browser, games, etc.), magazines, and other applicable methods. The platform may receive tokens from any number of sources.

Next, the platform brokers transactions involving the tokens associated with the sports player (step 2006). The platform may be configured to receive offers from any number of potential purchasers, licensees, assignees, owners, or so forth. The platform may allow buyers/sellers, licensors/licensees, or other applicable parties to negotiate applicable terms (e.g., price, time period, exclusivity, license fee, royalty rate, etc.).

Next, the platform performs transactions involving the tokens associated with the sports player (step 2008). As previously noted, any number of transactions or transaction types may be performed utilizing the platform. The platform may also allow each party to ensure that the transaction is performed fairly and transparently for both parties. For example, utilization of the blockchain may ensure that all transactions are performed transparently. The platform may also be configured to track additional distribution, sub-licenses, sales, or other transactions involving the content and tokens.

Next, the platform documents the transactions to ensure fair utilization and monetization of the carbon credits (step 2010). In one embodiment, the platform ensures that applicable information is able to be recorded in a blockchain digital ledger. The platform may also include one or more databases and digital ledgers for ensure open and fair transactions.

Figure 21:
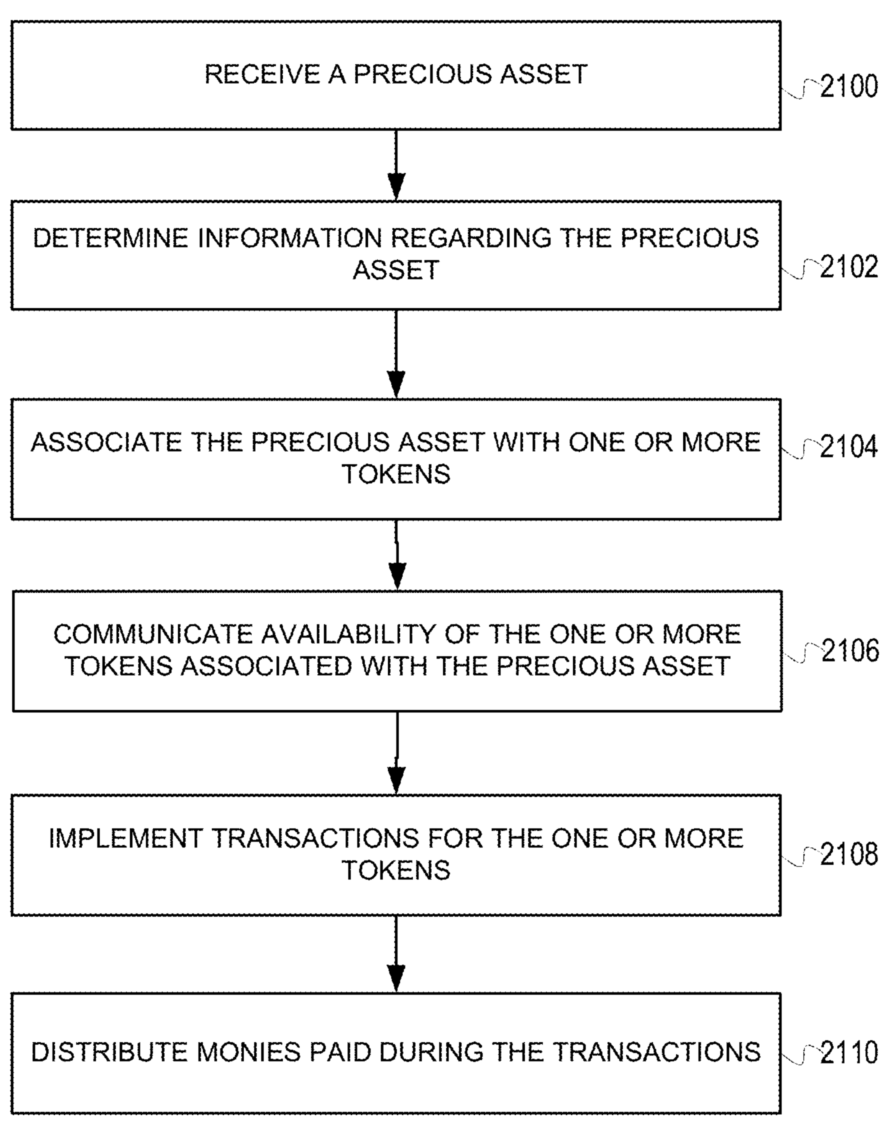
FIG. 21 is a flowchart of a process for protecting a precious asset utilizing a token in accordance with an illustrative embodiment.

FIG. 21 is a flowchart of a process for protecting a precious asset utilizing a token in accordance with an illustrative embodiment. The precious asset may represent any number of precious physical assets or items. The precious asset may represent any number of physical assets or items that are valuable, collectible, or have monetary, intrinsic, or sentimental value. The precious asset may also represent crude, raw, mined/unmined processed/refined, or other land, crops, natural resources (e.g., gold, gems, metal, rare earth elements or materials, etc.), or other materials or items. In some instances, the item is additionally documented with an RFID, tone, inaudible tone, chip, or other additional tracking device which may be used to provide additional authenticity and item verification.

In one embodiment, the process may begin by receiving a precious asset (step 2100). The precious asset may be received by an escrow group, repository, bank, financial institution, or other group authorized to receive and process precious assets. The precious asset may represent a precious metal, gem, or stone. In another embodiment, the precious asset may also represent digital or real-world artwork, paintings, collectibles (e.g., sports, non-sport activities, cards used in game items, stamps, coins, vintage clothes, toys, vehicles, etc.) and sporting memorabilia, or any physical items with actual or perceived value. In one example, the precious asset may represent one or more diamonds, platinum, gold, silver, lithium, precious metals, precious gems, and so forth. In another example, the precious asset may represent unmined diamonds or precious metals that are still in the ground. For example, a specified location, parcel, claim, vein, acreage, or geographic space may be designated.

Next, the platform determines information regarding the precious asset (step 2102). The information may describe the year of creation/discovery, location associated with the precious asset, manufacturer/discovering party, previous owners, value (e.g., appraised, intrinsic, expected, sold, etc.), description, and other applicable information. For example, where the precious asset is a precious metal or stone, the information may indicate the material type, number of karats, weight/troy ounces/pounds, stone quality, clarity, country of origin, mine/discovery location, processing information, previous owners, chain of title, modifications, maintenance, and so forth. The quantity and quality of the precious asset are very important to determine.

Next, the platform associates the precious asset with one or more tokens (step 2104). Identifying information regarding the precious asset may be associated with the one or more tokens. For example, a serial number, bar code, QR code, identification, number/marking/symbol, address, watermark, inaudible tone, tone, RFID, geolocation, or physical location, may be associated with a unique digital identifier (e.g., hash number, private key, public key, address, etc.) The precious asset may be associated with a single token or multiple tokens. For example, ownership may be held by a single owner or may be shared between multiple parties. In one embodiment, the information regarding the precious asset may be tokenized to form the one or more tokens in a unique or existing cryptocurrency or token. Any number of tokenization processes may be utilized.

Next, the platform communicates availability of the one or more tokens associated with the precious asset (step 2106). The platform may communicate availability of the precious asset utilizing any number of websites, messages (e.g., email, text, in-application message, etc.), interfaces, newsletters, newspapers, electronic communications, mobile applications, or so forth. The communications regarding the precious asset may indicate the availability to purchase, lease/rent, license, or otherwise perform transactions for the precious asset. The platform may perform any number of marketing, advertising, and promotional activities itself or through integrated, connected, or associated software, systems, platforms, devices, or so forth. In one embodiment, the platform may stipulate a price or value for the precious asset represented by the one or more tokens. For example, the valuation may represent the quantity multiplied by the price. Any number of other factors (e.g., meta/gem type, karats, weights, troy ounces, quality, purity, form, required processing, etc.) may also be utilized to value the precious asset.

Next, the platform implements transactions for the one or more tokens (step 2108). The platform may implement one or more transactions for the one or more tokens associated with the precious asset. For example, a purchasing party may purchase the tokens associated with the precious asset utilizing hard currency, cryptocurrency, wire payment, electronic payment, or other acceptable payment forms ("monies"). The platform ensures that the transaction is properly performed and documented utilizing one or more digital ledgers. The platform may also coordinate with one or more escrow groups, banks, financial institutions, or other groups that may be securely storing the precious asset for the past and/or future owner(s).

Next, the platform distributes monies paid during the transactions (step 2110). The platform may receive and process monies from the transaction. As noted, payments and distributions may be made utilizing any number of hard/fixed currencies, cryptocurrencies, or other accepted financial currencies or instruments.

Figure 22:
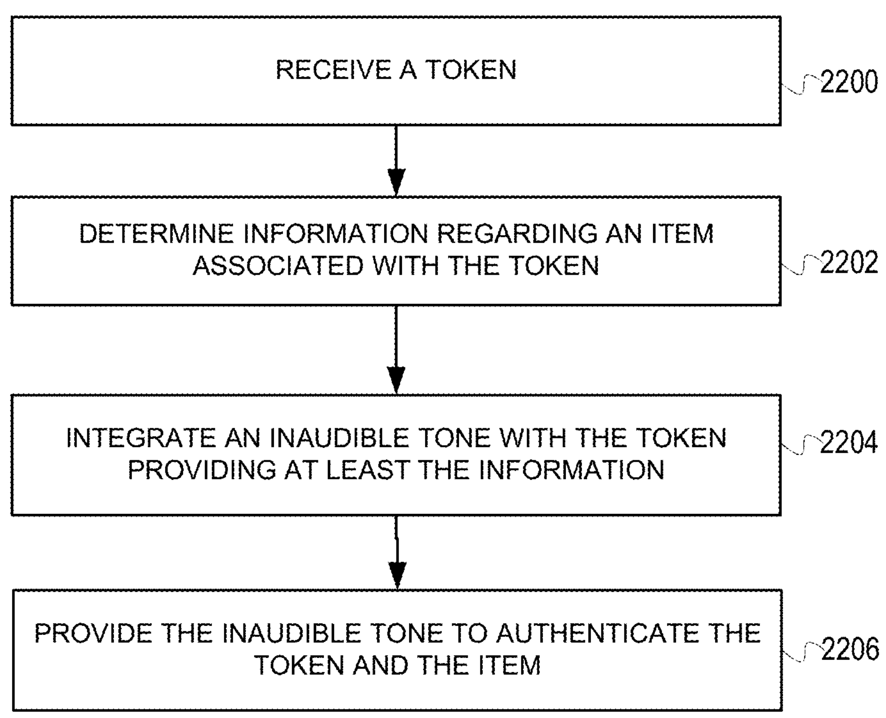
FIG. 22 is a flowchart of a process for authenticating a token utilizing an inaudible tone in accordance with an illustrative embodiment.

FIG. 22 is a flowchart of a process for authenticating a token utilizing an inaudible tone in accordance with an illustrative embodiment. The process of FIG. 22 may be performed as tokens are created or as data, content, information, or items are tokenized as described herein. In another embodiment, tokens may be enhanced or revised after creation or at any time. The process may begin by receiving a token (step 2200). As note, the tokens may represent any number of nonfungible tokens or tokens representing virtual or digital items, virtual items, or physical items and assets. The process may be performed utilizing any number of different blockchain tokens.

Next, the platform determines information regarding an item associated with the token (step 2202). The item may represent a virtual item, digital item, file, physical asset (e.g., mined and unmined precious gem/metal/coin, artwork, vehicle, home, collectible, etc.), or other content. The information may be related to the value of each asset and can contain metadata or details regarding the item, such as ownership, year created, creator/artist/manufacturer, identifying information (e.g., serial number, make/model, etc.), previous owner(s), condition, escrow location/company, and other applicable information. In the mining embodiment the tokenization process digital assets tied to mined and unmined assets are created and tokenized creating the ability to provide and track mined precious assets, and also track unmined precious assets that remains in the mines. The information within may include, but is not limited to, mining rights, precious metal or gem grade, the mine name and location, and market price fluctuations and market price at the time of purchase. In one embodiment unmined assets may be tokenized and valued with market rate pricing or fixed pricing at the time of asset purchase. Assets that require mining to extract value may be valued prior to the asset being mined. These unmined assets may be sold at market rate or sold at a spot price with a determined discount off of the market rate cost of the unmined asset. The buyer would assume downside risk whereas they benefit from the increase in the market price of the precious metal. A single platform may be utilized to create, manage, market, monetize, and create new revenue streams and asset valuations around asset quantity, price, tied to hard asset valuation around real time tokenized asset price determination, fluctuation, and valuation. The purchase of tokens tied to mined and unmined precious metal provides reduced operational and risk management costs, compliance with security, privacy and data sovereignty regulations in global markets and enhances existing anti-money laundering controls, fraud detection, sanction screening, regulatory reporting and may also act as a capital investment for future mining projects.

Next, the platform integrates an inaudible token with the token providing at least the information (step 2204). The inaudible tone is one or more audio signals that are inaudible to humans. The inaudible tone may be utilized to communicate the information as well as additional details about the token, the item, available transactions, or other information.

Next, the platform provides the inaudible tone to authenticate the token and the item (step 2206). For example, the inaudible tones may be utilized within a space to market the availability of the token and/or item for purchase, auction, licensing, or other applicable transactions. The inaudible tone may also be utilized to verify that the token is authentic. The information may include a certificate, Internet verification information, or other details for a potential party to verify and authenticate the token/item. The inaudible tones may also be utilized to verify any purchase, sale, license, or utilization of each unique token over time. In one embodiment, the platform or a physical item may be tagged or include an audio watermark with an inaudible tone transmitter in order to communicate the inaudible tones to one or more speakers, receivers, or personal computing devices, such as smart phones, tablets, wearable electronics, vehicles, or other electronic devices to validate and authenticate the token/item. The illustrative embodiments incorporate by reference U.S. Pat. Nos. 10,460,709, 11,030,983, 10,242,518 along with the associated description and drawings.

Figure 23:
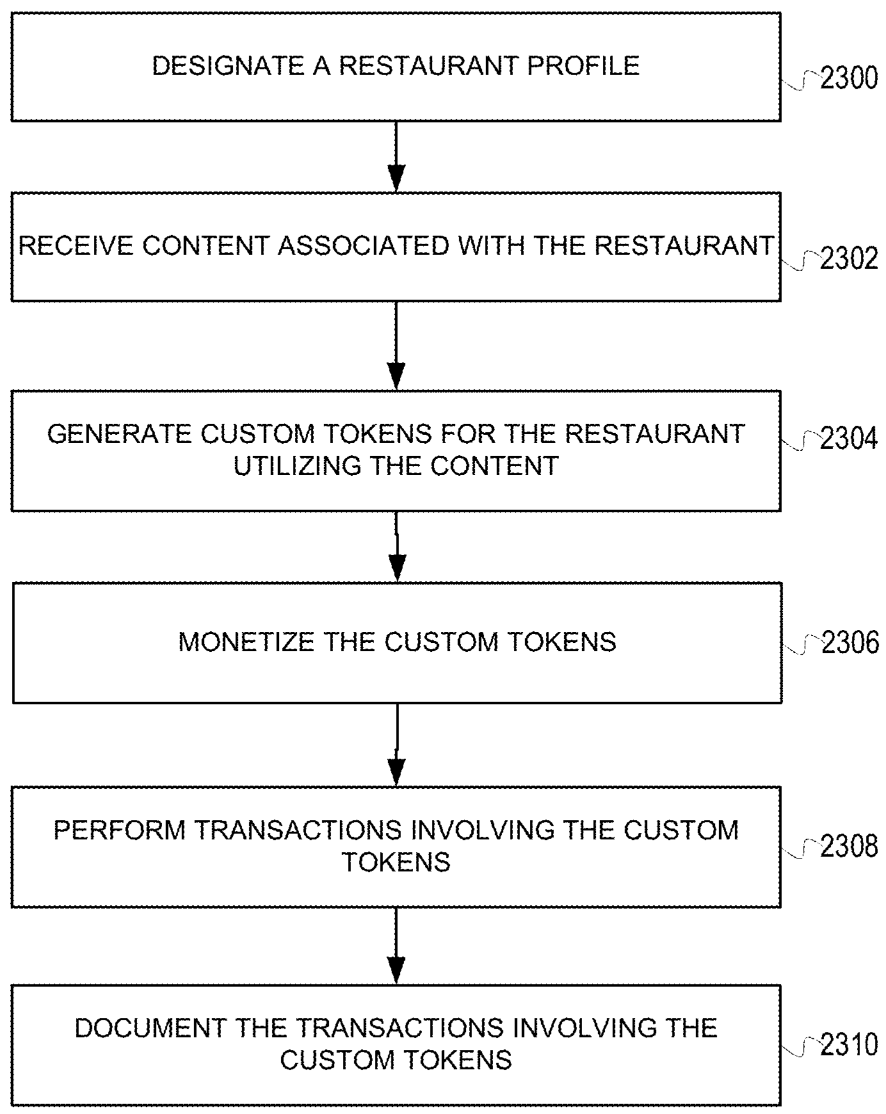
FIG. 23 is a flowchart of a process custom token generation in accordance with an illustrative embodiment.

FIG. 23 is a flowchart of a process custom token generation in accordance with an illustrative embodiment. The process of FIG. 23 may be applicable to any number of companies, groups, or organizations. In one embodiment, the process may be applicable to a restaurant or store. The process may begin by designating a restaurant or store profile (step 2300). The restaurant profile may specify information regarding a single location, multiple locations, a region, a chain of restaurants, or so forth. The restaurant or store profile may specify hiring, worker retention, consumer connections, best practices, marketing, brand outreach, campaign connectivity, and so forth.

Next, the platform receives content associated with the restaurant (step 2302). The content may also include internal information, such as consumer spending habits, loyalty rewards effectiveness, labor performance, inventory, parking lot traffic, grill times, drive thru time, seating times, food preparation times, customer satisfaction, and so forth. The platform may also tokenize real-world objects ranging from grills, kitchen equipment, signs, decorations, furniture, statues, artwork, or so forth.

Next, the platform generates custom tokens for the restaurant utilizing the content (step 2304). Any number of tokens may be generated for the content or assets associated with the restaurant. The custom tokens may be generated for single stores, restaurants, franchises, regions, associations, or other groups.

Next, the platform monetizes the custom tokens (step 2306). The tokens may be utilized to sell, lease, loan, or otherwise utilizes the physical or virtual assets of the restaurant. The platform may also value the tokens and associated content. Tokens and the associated content may be monetized based on remodels, upgrades, sales, or so forth.

Next, the platform performs transactions involving the custom tokens (step 2308). Hard currency, cryptocurrency, trades (e.g., inventory, food, goods, etc.) or other monetary exchanges may be utilized.

Next, the platform documents the transactions involving the custom tokens (step 2310). The transactions may be recorded by one or more digital ledgers.

Figure 24:
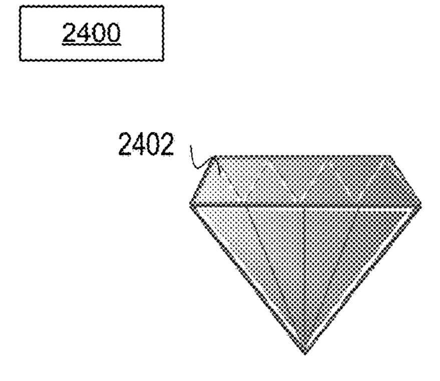
FIG. 24 is a pictorial representation of physical and virtual items associated with a blockchain token in accordance with the illustrative embodiments.
Figure 24:
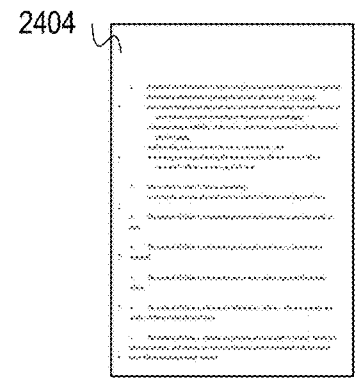
Figure 24:
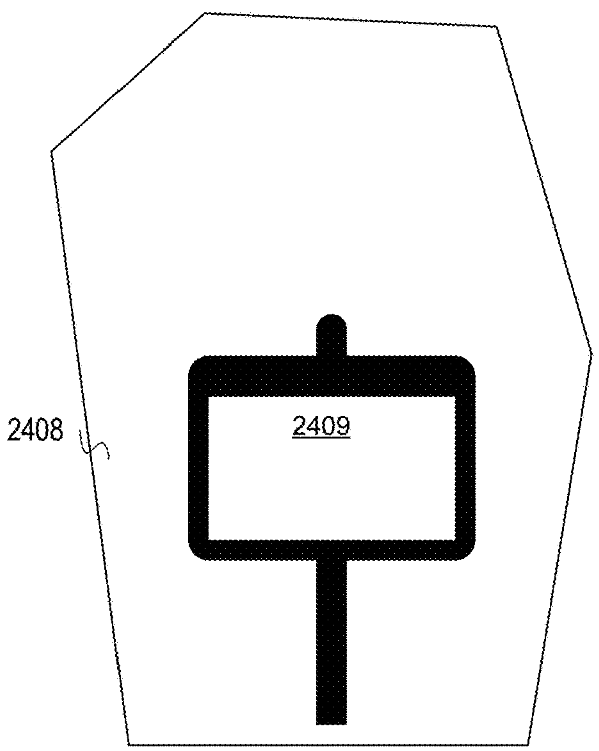
Figure 24:
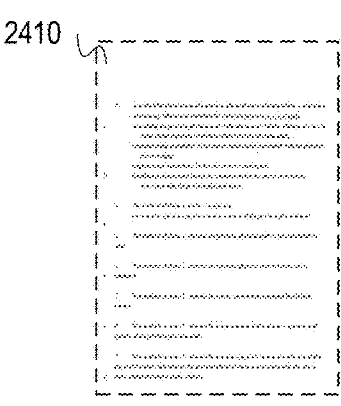
Figure 24:
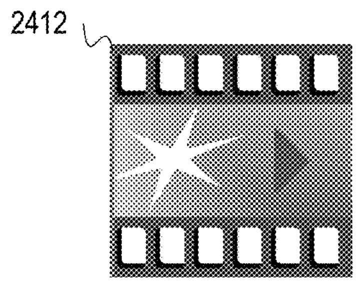
Figure 24:
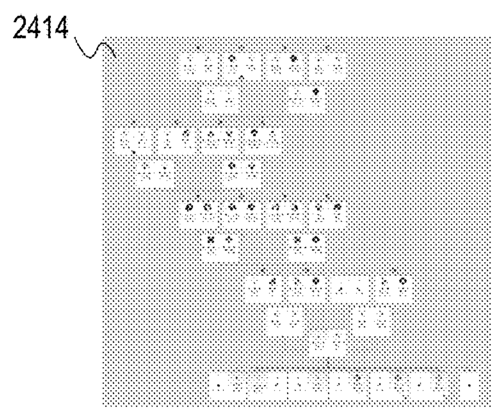

FIG. 24 is a pictorial representation of physical and virtual items associated with a blockchain token in accordance with the illustrative embodiments. The items 2402 may represent any number of physical, virtual, or physical and virtual items that may be associated with a blockchain token.

In one embodiment, a token 2400 may be associated with any of the items 2402. The token 2400 is representative of one or more blockchain tokens that may be associated with the items 2402. The items 2402 may include a gem 2404, a profile 2406, an unmined asset 2408, a data asset 2410, content 2412, a family tree 2414.

The gem 2404 may represent any number of precious gems, nuggets, rocks, jewels, jewelry, or valuable objects. In one embodiment, an identifier, hash, or other information associated with the token 2400 may be laser engraved on the gem 2404. Alternatively, a container or label of the gem 2404 may include the applicable information associated with the blockchain token 2400.

The profile 2406 may represent a physical or virtual profile. For example, the profile 2406 may represent a gaming profile, an Internet profile, a social media profile, a DNA profile, personal profile, corporate profile, or other type of profile. The profile may be generated based on compiled information or may be generated over time based on the activities, actions, and/or other observed behavior of the user that is authorized to be utilized. As previously noted, the user may authorize all or portions of the data in the profile 2406 to be compiled, shared, or otherwise utilized.

The unmined asset 2408 may include land or property that has verified minerals, gems, hydrocarbons, trees, crops, water, or other obtainable assets. The unmined asset 2408 may define a geographic area that may be mined, explored, or otherwise monetized. For example, the geographic area may be legally or geographically limited utilizing global positioning information, demarcations, boundaries, area, or so forth. As is known, the size, shape, and configuration of the unmined asset may vary significantly for the applicable terrain.

The token 2400 may be associated with the unmined asset 2408. The unmined asset 2408 may be tokenized with unmined, raw, refined, or other natural resources (e.g., hydrocarbons, water, trees, crops, herds, flocks, fields, minerals, metals, deposits, etc.). In one embodiment, the token 2400 may specify the location, boundaries, and limitations of the unmined asset 2408. The token 2400 may also specify the mining rights/ownership, grade of the unmined asset 2408, location/mine name, permits/regulations/laws, market price at the time of purchase, and additional information. In one embodiment, a sign 2409 may provide the applicable information associated with the token 2400. The sign 2409 may also represent a document or other digital resource. In one embodiment, the sign 2409 may be positioned at the location of the unmined asset 2408. In other embodiments, the sign 2409 may be associated with legal notices, postings, or documentation associated with the unmined asset 2408. The unmined asset 2408 may also be associated with a farm or ranch (e.g., crops, herds, etc.).

In one embodiment, a mine owner, operator, or other controlling party may sell access to tokens associated with tons of materials, portions of the property, royalty rights, or other portions of the mine itself or retrieved or unretrieved materials or resources. Sale of the token 2400 may be performed to allow the owner to receive capital investments, operating capital, or as an investment tool for individuals that buy the token 2400. Individual investors or groups may diversify their investment portfolio by buying tokens that are verified, authenticated, and validated before the tokens are generated. The price of the tokens may be fixed, variable with the spot price, or otherwise established based on the condition, processing, and future processing required for the unmined asset 2408. The buyer may assume downside risk associated with buying the token as well as the potential upside if the price of the resource increases over time. The token 2400 and others associated with the unmined asset 2408 may be traded over time on an exchange or platform as is described herein.

The data asset 2410 may represent any number of digital assets or a digital representation of a physical asset. For example, the digital asset 2410 may represent any number of profiles (e.g., gaming, Internet, online, HR, legal, investment, insurance, work, entertainment, etc.) that are controlled or owned utilizing the token 2400.

The content 2412 may represent physical, digital, or other content that is represented by at least the token 2400. For example, the content 2412 may represent artwork, collectible items, event tickets, music, media, games, videos, graphics, images, websites, domain names, memes, clothing, furniture, designs, pictures, courses/lessons, moments/events, and other content created, witnessed, or captured.

The family tree 2414 may represent the ancestry information of the user that is represented by the token 2400. The family tree 2414 may also include DNA information and a profile of the user (see for example profile 2406 or digital asset 2410). The family tree 2414 information may be shared with any number of family members, extended relatives, or friends.

Figure 25:
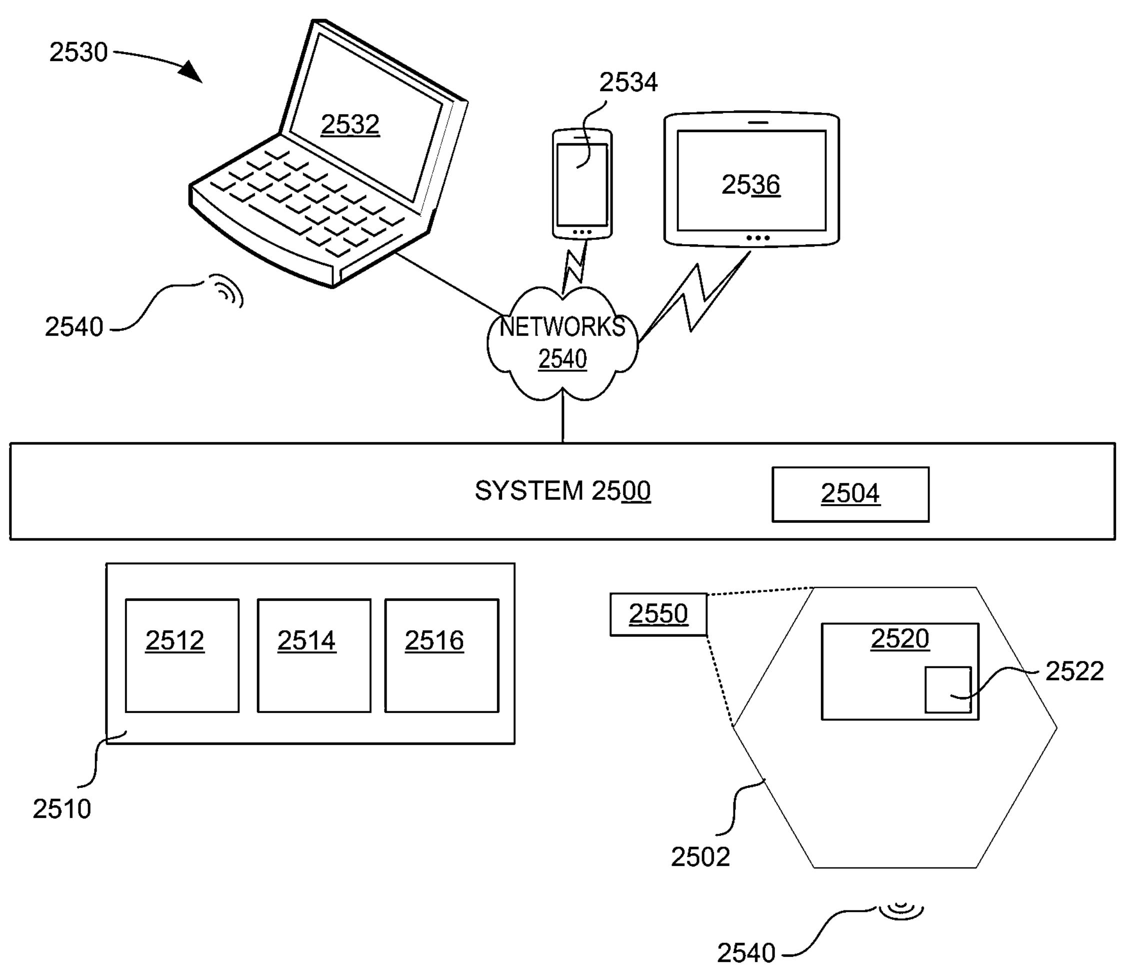
FIG. 25 is a representation of a token created based on an asset in accordance with an illustrative embodiment.

FIG. 25 is a representation of a token created based on an asset in accordance with an illustrative embodiment. In one embodiment, a system 2500 may be utilized to create a token 2502. The association between the token 2502 and the asset 2510 may be one-to-one. Alternatively, the asset 2510 may be controlled by multiple tokens. The token 2502 may represent a nonfungible token. The token 2502 may represent an asset 2510 (see FIG. 24 for a few examples). The asset may represent one or more of a physical asset 2512, a digital asset 2514, or a virtual asset 2516. The token 2502 may include an audible tag 2520. In one embodiment, the audible tag 2520 may include an audible identifier 2522. The audible identifier 2522 may include a unique alpha-numeric identifier that is utilized to identify the asset 2510 associated with the token 2502. The audible tag 2520 and audible identifier 2522 may alternatively be referred to as a tag and identifier especially if different broadcast/signal types are used (e.g., light, sensors, etc.).

The system 2500 may include a registry 2504. The registry may store all data and information associated with the audible tag 2520 including information and data relevant to the token 2502. The audible tag 2520 may represent the audible identifier 2522 at a specific frequency. As previously noted, the audible identifier 2522 may include inaudible tones/signals, audible tones/signals, optical signals, and/or a combination thereof. The audible identifier 2522 may include encoded data, patterns, or so forth. The data may be easily read or may be encrypted. The inaudible tones or signals are inaudible to humans.

In one embodiment, any number of electronic devices 2530, such as a personal computer 2532, smart phone 2534, tablet 2536, or other electronic devices (e.g., appliances, servers, security systems, commercial electronics, gaming devices, etc.) may be configured to listen for or detect the audible tag 2520 and the associated audible identifier 2522. The electronic devices 2530 may communicate with the system 2500 through any number of networks 2540. The networks 2540 may represent one or more wireless, satellite, wired, private, public, or other networks.

When the token 2502 is created the token 2502 includes or is associated with the asset 2510. The audible tag 2520 may be included in the digital asset 2514 or virtual asset 2516 (e.g., added, asset modified, new version created, etc.). The audible tag 2520 may be associated with the token in the registry 2504. The audible tag 2520 and audible identifier 2522 may be issued by an individual, company, organization, external sources, and/or a combination thereof. The audible tag 2520 may be utilized to perform validation and authentication of an NFT, such as the token 2502. The audible tag 2520 may communicate all or a portion of the information (e.g., publicly available information) stored within the token 2502. The integrity of the asset 2510 may be further protected utilizing the audible tag 2520. In one embodiment, the token 2502 may be uploaded, moved, or stored in a chip 2550.

The chip 2550 may include all or some of a processor/logic, memory, speaker, microphone, transceiver/interface, and/or sensors. The chip 2550 may be attached to or integrated with the physical asset 2512. As a result, the token 2502 may be better utilized to identify the physical asset 2512. The audible tag 2520 may be inserted by the originator, owner, creator, or other rights holder of the asset 2510 as part of the tokenization process or other processes. The audible tag 2520 may be utilized to track the purchase, sale, license, transfer, or changes to the token 2502 and associated asset 2510 over time.

When the token 2502 is opened, viewed, transacted, or otherwise engaged, the audio tag 2520 may be activated to emit a signal 2540, such as a sound (e.g., audible or inaudible), or light signal (e.g., visible light, ultraviolet, infrared, etc.). As noted, the electronic devices 2530 may detect the signal 2540 to identify the token 2502 and associated information and data including the audible tag 2520 and audible identifier 2522.

In one example, a movie trailer may be tokenized into the token 2502. The company associated with the movie trailer may generate an audible tag 2520 including the unique audible identifier 2522 that may be included within the movie trailer itself. The registry 2504 may record information specific to the movie trailer including all of the applicable information associated with the token 2502.

The registry 2504 may also create a log associating the audible identifier 2522 with the asset 2510, metadata, audible identifier 2522, and other related information. In one embodiment, the registry 2504 and/or log may be or write data to a blockchain. For example, when the token 2502 is utilized (e.g., played, sold, referenced, etc.) an electronic device, such as a smart phone may "hear" the audible tag 2520 to transmit the data base to the registry 2504. The registry 2504 may perform a lookup (or other database functionality) of the registry 2504 itself or associated databases, memories, servers, blockchains, or so forth. For example, a lookup of the audible identification 2522 may be utilized to perform authentication or verification of proper use, licensing/royalties, compensation, distribution, or so forth.

In one embodiment, the audible identifier 2522 may be mapped to a purchase cost, license fee, royalty, transaction fee including a specified amount of currency. The currency may be fixed or fluctuating (e.g., real-time updates). The currency or compensation may represent hard currency, cryptocurrency, rebates, discounts, or other forms of compensation.

In another example, the token 2502 may be utilized to purchase a ticket to an event. The ticket may require a specific amount of tokens (e.g., full, partial, etc.) or currency within the token 2502 to purchase access to the event. When the token is applied to the purchase, entry, or verification the audible tag 2520 may be emitted along with the audible identification 2522. The registry 2504 may be utilized to determine whether the token 2502 is sufficient to implement a transaction (e.g., sufficient cryptocurrency, tokens, cash, credits, etc.).

The system 2500 may map the audible identifier 2522 to a set of licensing rules related to the asset 2510. The rules may provide information regarding, where, when, what, and how the asset may be licensed, distributed, utilized, communicated, transferred, or so forth. In one embodiment, the licensing rules may be stored in a smart contract associated with the token 2502 that may be stored in the registry 2504.

In one embodiment, the asset 2510 may be a song (e.g., recorded music file, video, etc.). The song may have limited distribution rights associated with the holder of the token 2502 for distribution through a stream platform or provider. When the digital asset 2514/song is tokenized as token 2502 the audible tag 2520 along with the audible identifier 2522 may be inserted and mapped to the song and licensing information and metadata. The token 2502 may then be distributed by a music label to a distributor. When the token 2502 is utilized to play the song, the audio identification may be heard or found by the registry 2504. As a result, the registry 2504 may ensure that the license rights are being honored and maintained. In addition, the registry 2504 may also ensure that proper payments or compensation for the song are being implemented.

The assets 2510 may also represent physical, digital, virtual, or other forms of memorabilia. The memorabilia may relate to sports, entertainment, science, education, and any number of other topics. For example, the assets may include (new or used) baseball player profiles, baseball hats, uniforms, cleats, bases, game balls, practice balls, pads, kicking tees, pucks, pads, skates, helmets, car parts, tires, and other gear, equipment, or so forth. For example, sports memorabilia may relate to recreational, amateur, high school, semi-professional, college, professional (e.g., NBA, NFL, NHL, MLB, etc.), Olympic, or other levels of athletes. Ownership of memorabilia may be owned entirely, in part, or in fractions (e.g., equal or inequal).

In one embodiment, the physical assets 2512 may represent gold, precious metals or stones that may be tokenized based on information, such as karats, weight, quality, clarity, and so forth. The valuation typically uses the value equals quantity times price (V=Q*P) as one measurement tool, but other factors may be considered and utilized. The token 2502 that is created based on the asset may also include information regarding the country of origin, mine/extraction point, government licenses or authorizations, manufacturing processes, companies involved, and so forth.

As noted herein, the assets 2510 that are tokenized may represent any number of virtual or physical assets or items that are valuable, collectible, or have monetary, intrinsic, or sentimental value. The asset 2510 may also represent crude, raw, processed/refined, or other land, crops, natural resources (e.g., gold, gems, metal, rare earth elements or materials, etc.), mined or unmined precious metals or gems or other materials or items. In some instances, the item is additionally documented with an RFID, tone, inaudible tone, chip, sticker, or other additional tracking device which may be used to provide additional authenticity and item verification.

In one embodiment, the system 2500 may receive an asset 2510. The asset 2510 and/or ownership, title, or assignment documents associated with the asset 2510 may be received by an escrow group, repository, bank, financial institution, or other group authorized to receive and process precious assets. The asset 2510 may represent a precious metal, gem, or stone. In another embodiment, the asset 2510 may also represent artwork, paintings, collectibles (e.g., sports, non-sport activities, sports cards, used in game items, stamps, coins, vintage clothes, toys, comics, vehicles, collections etc.) and sporting memorabilia, or any physical items with actual or perceived value. In one example, the asset 2510 may represent one or more diamonds, platinum, gold, silver, and so forth. In another example, the precious asset may represent unmined diamonds, coal, lithium, or precious metals that are still in the ground. For example, a specified location, parcel, claim, vein, acreage, or geographic space may be designated.

The system 2500 may also determine information regarding the asset 2510. The information may describe the year of creation/discovery, location associated with the asset, manufacturer/discovering party, previous owners, value (e.g., appraised, intrinsic, expected, sold, etc.), description, and other applicable information. For example, where the asset 2510 is a precious metal or stone, the information may indicate the material type, number of karats, weight/troy ounces/pounds, stone quality, clarity, country of origin, mine/discovery location, processing information, previous owners, chain of title, modifications, maintenance, and so forth. The quantity and quality of the asset 2510 are very important to determine.

The system 2500 may utilize the information and asset to generate the token 2502. All or portions of the information associated with the asset 2502 may be stored in the token 2502 for utilization, transactions, monetization, tracking, management, and so forth.

The illustrative embodiments provide a path to utilized blockchain tokens to extract value from any number of physical or digital assets or content. As a result, a platform and market for creating, distributing, monetizing, and advertising assets and the associated token(s) may be created. The illustrative embodiments may utilize any of the system, processes, description, and Figures of application Ser. Nos. 17/291,411, 17/441,847, 16/125,236, 17/039,591, and 17/119,479 which are hereby incorporated by reference in their entirety.

The features, steps, and components of the illustrative embodiments may be combined in any number of ways and are not limited specifically to those described. In particular, the illustrative embodiments contemplate numerous variations in the smart devices and communications described. The foregoing description has been presented for purposes of illustration and description. It is not intended to be an exhaustive list or limit any of the disclosure to the precise forms disclosed. It is contemplated that other alternatives or exemplary aspects are considered included in the disclosure. The description is merely examples of embodiments, processes, or methods of the invention. It is understood that any other modifications, substitutions, and/or additions may be made, which are within the intended spirit and scope of the disclosure. For the foregoing, it can be seen that the disclosure accomplishes at least all of the intended objectives.

The previous detailed description is of a small number of embodiments for implementing the invention and is not intended to be limiting in scope. The following claims set forth a number of the embodiments of the invention disclosed with greater particularity.

What is claimed is:

1. A method for managing content utilizing tokens from a data platform, comprising:

providing an incentive for a user to generate content according to a smart contract, wherein the smart contract governs how tokenized content is utilized and monetized;

presenting a user interface configured to allow the user to select one or more monetization strategies for the tokenized content according to the smart contract and permissions;

automatically receiving the content generated by the user, the content is saved in one or more storages of the data platform;

determining whether the content includes user information including personally identifiable information;

deidentifying the user information from the content generated by the user according to the smart contract to generate deidentified content to protect the privacy of the user;

tokenizing the deidentified content into one or more tokens utilizing a data refinery of the data platform;

determining a monetization level for the tokenized content based on one or more characteristics of the data;

distributing the tokenized content for monetization, wherein the tokenized content is selectively accessible to one or more authorized parties based on the permissions defined in the smart contract;

monetizing the tokenized content based on the smart contract; and compensating the user utilizing the smart contract based on the incentive for the monetization of the tokenized content.

2. The method of claim 1, wherein the one or more tokens are blockchain tokens, and wherein the one or more tokens and associated content are saved in a digital ledger.

3. The method of claim 1, wherein the content is received from a plurality of electronic sources associated with the data platform, and wherein the content includes at least video or images.

4. The method of claim 1, further comprising:

valuing the content based on the characteristics of the data including at least source reliability, content type, or deidentification level;

determining potential monetization strategies for the tokenized content;

presenting the monetization strategies to the user through a user interface; and presenting the user interface for communicating the tokenized content to one or more authorized parties.

5. The method of claim 4, wherein the monetization strategies include at least selling the tokenized content and leasing the tokenized content to the one or more authorized parties.

6. The method of claim 1, wherein the incentive is cryptocurrency.

7. The method of claim 1, wherein the user uploads the content from one of a plurality of electronic devices executing an application that interfaces with the data platform.

8. The method of claim 1, further comprising:

compensating the user based on terms negotiated between the user and a service provider operating the data platform in response to the creating the smart contract controlling utilization of the content.

9. The method of claim 1, further comprising:

generating each of the one or more tokens associated with the tokenized content.

10. The method of claim 1, further comprising:

advertising the content to the one or more authorized parties; and performing transactions for the one or more tokens associated with the tokenized content.

11. A system for managing content, comprising:

a plurality of electronic devices executing a data application, the data application is configured to capture the user data associated with a user; and a data platform accessible by the plurality of electronic devices executing the data application through one or more networks, wherein the data platform provides an incentive for a user to generate content according to a smart contract, wherein a user interface is configured to allow the user to select how the smart contract governs how tokenized content is utilized and monetized including permissions, automatically receives the content generated by the user, determines whether the content includes user information including personally identifiable information, deidentifies the user information from the content generated by the user according to the smart contract to generate deidentified content to protect the privacy of the user, tokenizes the deidentified content into one or more tokens utilizing a data refinery, determines a monetization level for the tokenized content based on one or more characteristics of the data, distributes the tokenized content for monetization, monetizes the tokenized content based on the smart contract, wherein the tokenized content is selectively accessible to one or more authorized parties based on the permission defined in the smart contract, and compensates the user based on the incentive for the monetization of the tokenized content.

12. The system of claim 11, wherein the data platform values the tokenized content, determines potential monetization strategies for the tokenized content, presents the monetization strategies to the user, and performs transactions for the tokenized content.

13. The system of claim 11, wherein the one or more tokens are blockchain tokens, and wherein the one or more tokens and associated tokenized content are saved in a digital ledger.

14. The system of claim 11, wherein the incentive is cryptocurrency, and wherein the user is compensated for the tokenized content utilizing the cryptocurrency.

15. The system of claim 11, wherein the data platform further:

communicates information for a user interface to present the tokenized content to one or more authorized parties; and processes payment for purchase of the tokenized content from at least one of the one or more authorized parties.

16. A data platform, comprising:

a processor for executing a set of instructions;

a memory for storing the set of instructions, wherein the set of instructions are executed to:

provide an incentive for a user to generate content according to a smart contract, wherein the smart contract governs how tokenized content is utilized and monetized;

present a user interface configured to allow the user to select one or more monetization strategies for the tokenized content according to the smart contract and permissions;

automatically receive the content generated by the user, the content is saved in one or more storages of the data platform, the content includes at least one or more images or videos;

tokenize the content generated by the user into one or more tokens utilizing a data refinery;

determine a monetization level for the tokenized content based on one or more characteristics of the data;

presenting a user interface for presenting the tokenized content to one or more authorized parties;

distribute the tokenized content for monetization, wherein the tokenized content is selectively accessible to one or more authorized parties based on the permissions defined in the smart contract;

monetize the tokenized content in the one or more tokens based on the smart contract; and compensates the user based on the incentive for the monetization of the tokenized content in the one or more tokens.

17. The data platform of claim 16, wherein the set of instructions are further executed to:

value the tokenized content based on the characteristics of the data including at least source reliability, content type, or deidentification level, determine potential monetization strategies for the tokenized content, present the monetization strategies to the user, and perform transactions for the tokenized content with the one or more authorized parties.

18. The data platform of claim 16, wherein private user information is removed from the tokenized content to protect the privacy of the user, wherein the one or more tokens are blockchain tokens, and wherein the one or more tokens and associated tokenized content are saved in a digital ledger.

19. The data platform of claim 16, wherein the set of instructions generate each of the one or more tokens associated with the content, advertise the tokenized content to the one or more authorized parties, and perform transactions for the one or more tokens associated with the tokenized content with the one or more authorized parties.

20. The data platform of claim 16, wherein the set of instructions are further executed to:

advertise the tokenized content to the one or more authorized parties; and perform transactions for the one or more tokens associated with the tokenized content.

* * * * *